United States Patent
Nishimae et al.

(10) Patent No.: US 11,706,981 B2
(45) Date of Patent: Jul. 18, 2023

(54) ORGANIC LIGHT EMITTING DEVICE AND COMPOUNDS FOR USE IN SAME

(71) Applicant: Idemitsu Kosan Co., Ltd., Chiyoda-ku (JP)

(72) Inventors: Yuichi Nishimae, Basel (CH); Natalia Chebotareva, Hagenthal le Bas (FR)

(73) Assignee: Idemitsu Kosan Co., Ltd., Chiyoda-ku (JP)

( * ) Notice: Subject to any disclaimer, the term of this patent is extended or adjusted under 35 U.S.C. 154(b) by 599 days.

(21) Appl. No.: 16/738,007

(22) Filed: Jan. 9, 2020

(65) Prior Publication Data
US 2020/0227652 A1 Jul. 16, 2020

(30) Foreign Application Priority Data

Jan. 10, 2019 (EP) .................... 19151210

(51) Int. Cl.
| | |
|---|---|
| C09K 11/06 | (2006.01) |
| C07D 209/80 | (2006.01) |
| C07D 209/82 | (2006.01) |
| C07D 401/04 | (2006.01) |
| C07D 491/06 | (2006.01) |
| C07D 491/052 | (2006.01) |
| H05B 33/20 | (2006.01) |
| H10K 85/60 | (2023.01) |
| C09K 11/02 | (2006.01) |
| H10K 50/11 | (2023.01) |
| H10K 71/00 | (2023.01) |
| H10K 71/16 | (2023.01) |
| H10K 101/10 | (2023.01) |
| H10K 102/00 | (2023.01) |

(52) U.S. Cl.
CPC ....... H10K 85/6572 (2023.02); C07D 209/80 (2013.01); C07D 401/04 (2013.01); C07D 491/06 (2013.01); C09K 11/025 (2013.01); H10K 50/11 (2023.02); H10K 71/00 (2023.02); H10K 71/164 (2023.02); H10K 2101/10 (2023.02); H10K 2102/351 (2023.02)

(58) Field of Classification Search
CPC ............. H10K 85/622; H10K 85/6572; H10K 85/342; H10K 50/11; H10K 71/00; H10K 71/164; H10K 2101/10; H10K 2102/351; C07D 209/80; C07D 209/82; C07D 401/04; C07D 491/06; C07D 491/052; H05B 33/20; C09K 11/025; C09K 11/06
See application file for complete search history.

(56) References Cited

U.S. PATENT DOCUMENTS

2015/0255726 A1    9/2015   Kawamura et al.

FOREIGN PATENT DOCUMENTS

| CN | 104513660 A | 4/2015 |
|---|---|---|
| KR | 10-2018-0010409 A | 1/2018 |
| WO | WO 2010/114264 A2 | 10/2010 |
| WO | WO 2016/099037 A2 | 6/2016 |
| WO | WO 2017/109722 A1 | 6/2017 |
| WO | WO 2017/109727 A1 | 6/2017 |

OTHER PUBLICATIONS

Kimio Hirano, et al. "Gold(I)-Catalyzed Polycyclizations of Polyenyne-Type Anilines Based on Hydroamination and Consecutive Hydroarylation Cascade" The Journal of Organic Chemistry, vol. 76, 2011, pp. 9068-9080.

*Primary Examiner* — Sun Jae Yoo
(74) *Attorney, Agent, or Firm* — Oblon, McClelland, Maier & Neustadt, L.L.P.

(57) ABSTRACT

Specific polycyclic compounds of the general formula (I) and a process for its preparation, an electronic device comprising at least one of these compounds, an emitting layer, preferably present in an electronic device, comprising at least one compound of general formula (I) and the use of compounds according to general formula (I) in an electronic device as a host material, a charge transporting material, charge and/or exciton blocking material, preferably as a host material or an electron transporting material.

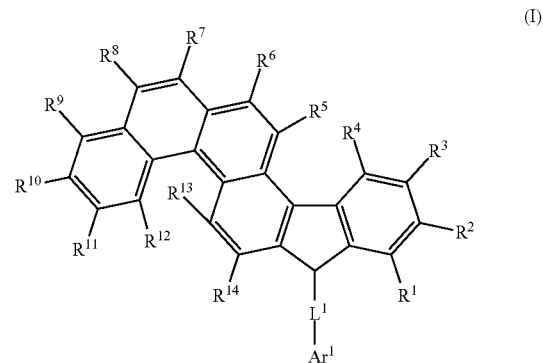

12 Claims, 1 Drawing Sheet

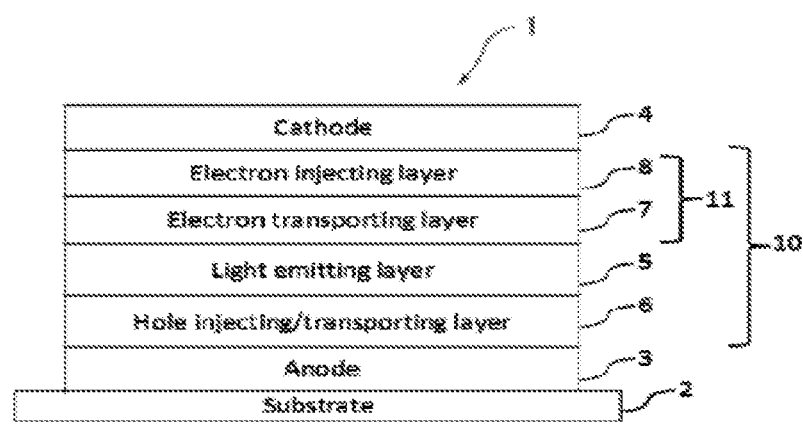

ORGANIC LIGHT EMITTING DEVICE AND COMPOUNDS FOR USE IN SAME

The present invention relates to a polycyclic compound of the general formula (I) and to a process for its preparation, to an electronic device comprising at least one of these compounds, to an emitting layer, preferably present in an electronic device, comprising at least one compound of general formula (I) and to the use of compounds according to general formula (I) in an electronic device as a host material, a charge transporting material, charge and/or exciton blocking material, preferably as a host material or an electron transporting material.

Polycyclic compounds and their use in electronic devices are generally known from the related art.

WO 2010/114264 relates to organic electroluminescent compounds of the following formula 1 and organic electroluminescent devices including the same

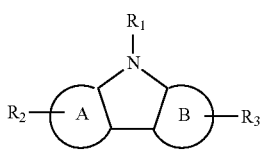
(1)

wherein ring A and ring B independently represents a monocyclic or polycyclic aromatic ring, a monocyclic or polycyclic heteroaromatic ring, a 5- or 6-membered heteroaromatic ring fused with an aromatic ring, a monocyclic or polycyclic aromatic ring fused with a 5- or 6-membered heteroaromatic ring; excluding the case that both the ring A and the ring B are monocyclic aromatic rings.

One compound exemplified in WO 2010/114264 is the following compound

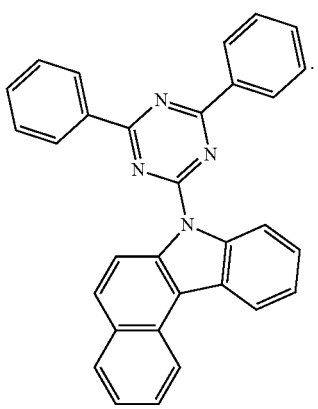

Kimio Hirano, et al., J. Org. Chem. 2011, 76, 9068-9080 disclose compounds according to the following formulae:

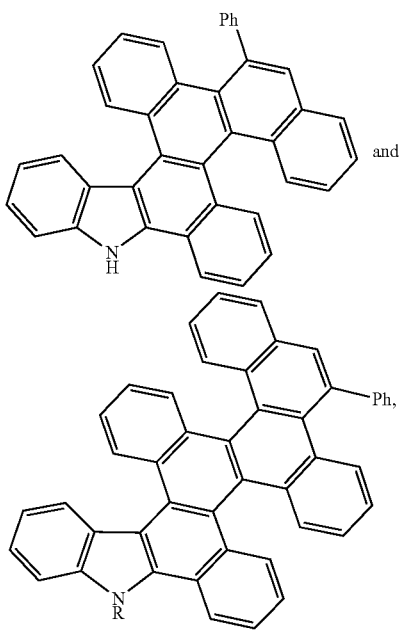

wherein R is hydrogen or tosyl. This document teaches nothing about their use.

US 2015/0255726 A1 discloses compounds according to the following formulae:

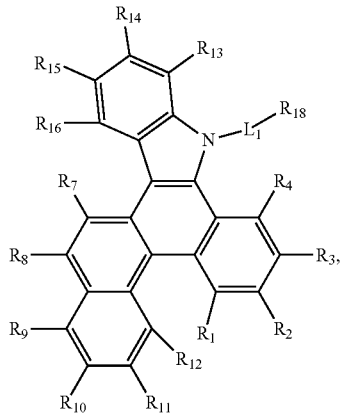

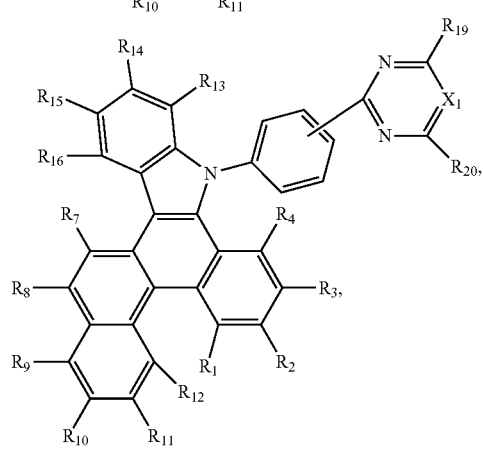

-continued

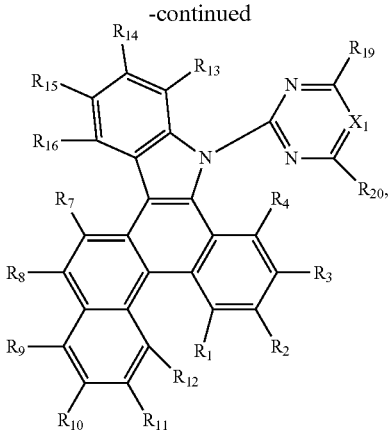

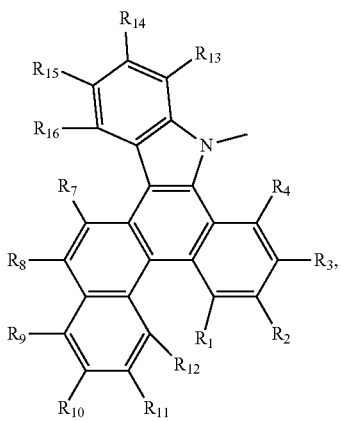

wherein $R_1$ to $R_4$ and $R_7$ to $R_{16}$ are all hydrogen, are actually described as exemplified compounds. This document further discloses their use as electroluminescent device materials.

WO 2017/109727 A1 relates to compounds of general formula (I)

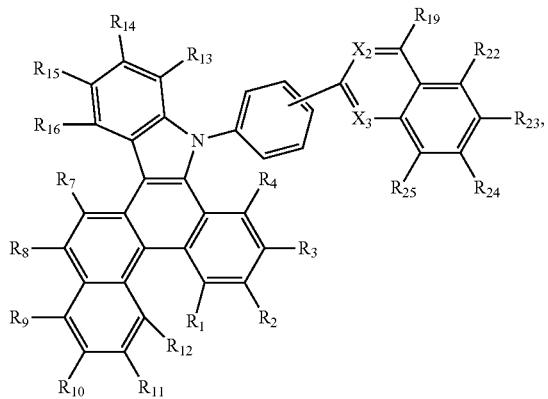

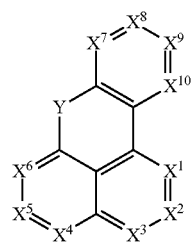
(I)

and their use in electronic devices, for example compounds of the following formulae:

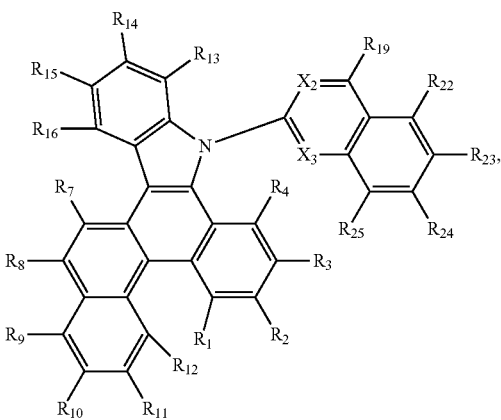

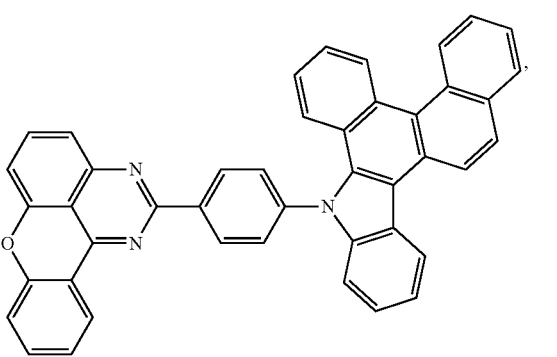
Compound 5 etc., wherein $X_2$ and $X_3$ may be nitrogen, each of $R_1$ to $R_4$, $R_7$ to $R_{16}$, $R_{18}$ to $R_{20}$, $R_{22}$ to $R_{25}$ may be alkyl, aryl, or heteroaryl, and $L_1$ may be direct bond or arylene. Only the compounds having the following structure:

-continued

Compound 16

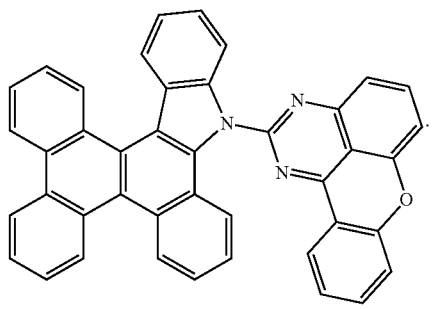

Compound 4

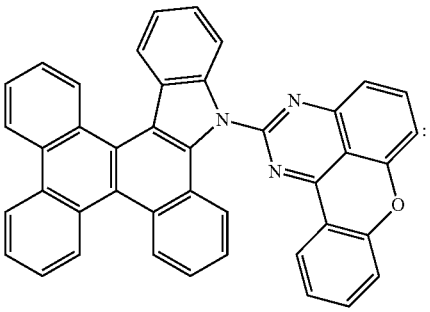

WO 2017/109722 A1 relates to nitrogen-containing heterocyclic compounds and organic electronic devices comprising them. Compounds having the following structures Compound 1

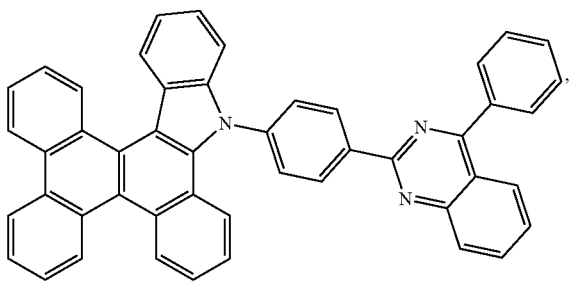

Compound 2

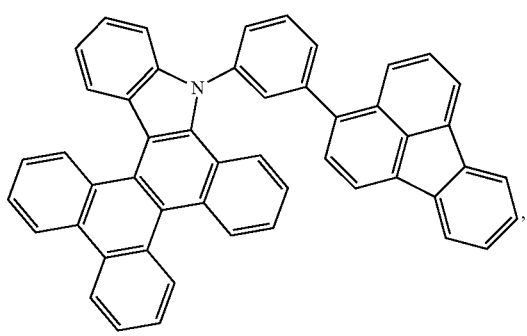

Compound 3

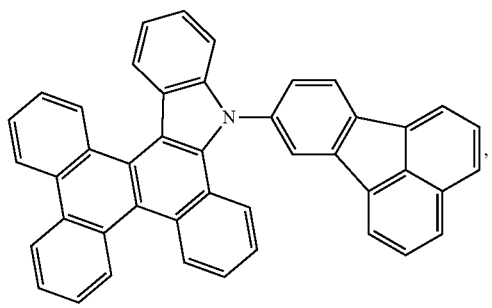

are actually described as exemplified compounds.

It is an object of the present invention to provide electronic devices, preferably OLEDs, comprising new compounds, especially as a host material, a charge transporting material, charge and/or exciton blocking material, preferably as a host material, having a good overall performance, i.e. good balance of properties, for example low driving voltages, improved lifetimes and/or improved efficiency.

This object is solved by a polycyclic compound represented by formula (I):

(I)

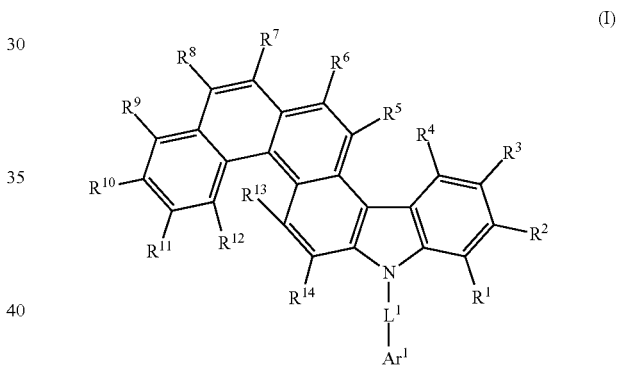

wherein, $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ are independently of each other hydrogen, an unsubstituted or substituted $C_6$-$C_{24}$aryl group, an unsubstituted or substituted $C_1$-$C_{30}$ heteroaryl group, an unsubstituted or substituted $C_1$-$C_{25}$alkyl group, an unsubstituted or substituted $C_7$-$C_{25}$aralkyl group, an unsubstituted or substituted $C_5$-$C_{12}$cycloalkyl group, —$NR^{15}R^{16}$, —$OR^{17}$, —$SR^{18}$, —$SiR^{19}R^{20}R^{21}$, —CN or halogen, wherein two of $R^1$, $R^2$, $R^3$, $R^4$, $R^5$, $R^6$, $R^7$, $R^8$, $R^9$, $R^{10}$, $R^{11}$ and $R^{12}$, if present at adjacent carbon atoms, together may form an unsubstituted or substituted $C_6$-$C_{18}$aryl ring;

$L_1$ is a direct bond, an unsubstituted or substituted $C_6$-$C_{24}$arylene group, or an unsubstituted or substituted $C_1$-$C_{30}$heteroarylene group; and $Ar^1$ is an unsubstituted or substituted $C_6$-$C_{24}$aryl group, or an unsubstituted or substituted $C_1$-$C_{30}$heteroaryl group;

$R^{15}$ and $R^{16}$ are independently of each other H, a $C_6$-$C_{18}$aryl group which is unsubstituted or substituted by at least one $C_1$-$C_{18}$alkyl group or at least one $C_1$-$C_{18}$alkoxy group, a $C_1$-$C_{18}$alkyl group or a $C_1$-$C_{18}$alkyl group, which is interrupted by at least one O, or $R^{15}$ and $R^{16}$ together form a five or six membered aliphatic, aromatic or heteroaromatic ring;

$R^{17}$ and $R^{18}$ are independently of each other H, a $C_6$-$C_{18}$aryl group which is unsubstituted or substituted by at least one $C_1$-$C_{18}$alkyl group or at least one $C_1$-$C_{18}$alkoxy group, a $C_1$-$C_{18}$alkyl group or a $C_1$-$C_{18}$alkyl group, which is interrupted by at least one O;

$R^{19}$, $R^{29}$ and $R^{21}$ are independently of each other a $C_1$-$C_{18}$alkyl group, a $C_6$-$C_{18}$aryl group which is unsubstituted or substituted by at least one $C_1$-$C_{18}$alkyl group.

The compounds of formula (I) are suitable as material for electronic devices, preferably OLEDs, especially as a host material, a charge transporting material, charge and/or exciton blocking material, preferably as a host material, having a good overall performance, i.e. good balance of properties, for example low driving voltages, improved lifetimes and/or an improved efficiency. It has been found by the inventors that the presence of a benzannulation at the positions $R^{13}$ and $R^{14}$ of the compounds of formula (I) of the present invention is disadvantageous for the OLED's performance, especially for the lifetime of OLEDs.

The residues and indices mentioned in the specification of the present application generally have the following preferred meanings, if said residues and indices are not further specified in specific embodiments mentioned below:

Halogen is fluorine, chlorine, bromine or iodine.

$C_1$-$C_{25}$alkyl, preferably $C_1$-$C_{18}$alkyl, is typically linear or, where possible, branched alkyl. Examples are methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, or octadecyl. $C_1$-$C_8$alkyl is typically methyl, ethyl, n-propyl, isopropyl, n-butyl, sec-butyl, isobutyl, tert-butyl, n-pentyl, 2-pentyl, 3-pentyl, 2,2-dimethyl-propyl, n-hexyl, n-heptyl, n-octyl, 1,1,3,3-tetramethylbutyl and 2-ethylhexyl. $C_1$-$C_4$alkyl is typically methyl, ethyl, n-propyl, isopropyl, n-butyl, sec-butyl, isobutyl, tert-butyl.

$C_1$-$C_{18}$alkoxy groups are straight-chain or branched alkoxy groups, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy. Examples of $C_1$-$C_8$alkoxy are methoxy, ethoxy, n-propoxy, isopropoxy, n-butoxy, sec-butoxy, isobutoxy, tert-butoxy, n-pentyloxy, 2-pentyloxy, 3-pentyloxy, 2,2-dimethylpropoxy, n-hexyloxy, n-heptyloxy, n-octyloxy, 1,1,3,3-tetramethylbutoxy and 2-ethylhexyloxy, preferably $C_1$-$C_4$alkoxy such as typically methoxy, ethoxy, n-propoxy, isopropoxy, n-butoxy, sec-butoxy, isobutoxy, tert-butoxy.

$C_6$-$C_{24}$aryl, preferably $C_6$-$C_{18}$aryl, particularly preferably $C_6$-$C_{16}$aryl, which optionally can be substituted, are typically phenyl, 4-methyl phenyl, 4-methoxyphenyl, naphthyl, especially 1-naphthyl, or 2-naphthyl, biphenylyl, terphenylyl, pyrenyl, 2- or 9-fluorenyl, phenanthryl, triphenylene-yl, fluoranthene-yl, especially fluoranthene-1-yl, fluoranthene-2-yl, fluoranthene-3-yl, fluoranthene-7-yl or fluoranthene-8-yl, benzofluoranthenyl, especially benzo[a]fluoranthenyl, benzo[j]fluoranthenyl, benzo[k]fluoranthenyl or benzo[b]fluoranthenyl, or anthryl, which may be unsubstituted or substituted. Preferred aryl groups are phenyl, naphthyl, especially 1-naphthyl, or 2-naphthyl, phenanthryl, triphenylene-yl, or fluoranthene-yl, especially fluoranthene-1-yl, fluoranthene-2-yl, fluoranthene-3-yl, fluoranthene-7-yl or fluoranthene-8-yl, which may be unsubstituted or substituted.

$C_1$-$C_{30}$heteroaryl, preferably $C_1$-$C_{24}$heteroaryl, preferably $C_1$-$C_{18}$heteroaryl, more preferably $C_3$-$C_{18}$heteroaryl, and particularly preferably $C_3$-$C_{15}$heteroaryl, which optionally can be substituted, represents a ring with five to seven ring atoms or a condensed/fused ring system, wherein nitrogen, oxygen or sulfur are the possible hetero atoms, such as thiophenyl, benzothiophenyl, dibenzothiophenyl, azadibenzothiophenyl, diazadibenzothiophenyl, thianthrenyl, furanyl, furfuryl, 2H-pyranyl, benzofuranyl, isobenzofuranyl, dibenzofuranyl, especially dibenzofuran-2-yl group, dibenzofuran-4-yl group, dibenzofuran-1-yl group or dibenzofuran-3-yl group, azadibenzofuranyl, diazadibenzofuranyl, phenoxythiophenyl, pyrrolyl, imidazolyl, pyrazolyl, pyridyl, bipyridyl, triazyl, pyrimidyl, pyrazinyl, pyridazinyl, indolizinyl, isoindolyl, indolyl, indazolyl, purinyl, quinolizinyl, quinolyl, isoquinolyl, phthalazinyl, naphthyridinyl, quinoxalinyl, quinazolinyl, benzoquinazolinyl, cinnolinyl, pteridinyl, carbazolyl, especially 9-phenylcarbazole-3-yl, 9-phenylcarbazole-2-yl or 9-phenylcarbazole-4-yl group, carbolinyl, benzotriazolyl, benzoxazolyl, phenanthridinyl, acridinyl, pyrimidinyl, phenanthrolinyl, phenazinyl, isothiazolyl, phenothiazinyl, isoxazolyl, furazanyl, 4-imidazo[1,2-a]benzimidazolyl, 5-benzimidazo[1,2-a]benzimidazolyl, benzimidazolo[2,1-b][1,3]benzothiazolyl, or phenoxazinyl, which can be unsubstituted or substituted, or a group of formula (A)

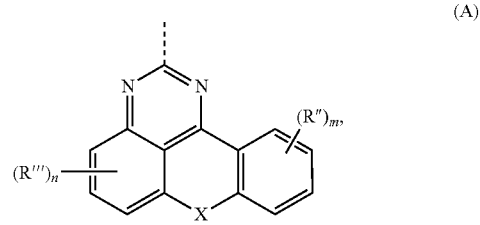

(A)

wherein X is O, NR, CR'$_2$ or S, R is an unsubstituted or substituted $C_6$-$C_{10}$ aryl group, preferably unsubstituted or substituted phenyl, more preferably unsubstituted phenyl; R' is $C_1$-$C_4$-alkyl, preferably methyl, ethyl, n-propyl, iso-propyl, n-butyl, iso-butyl or tert.-butyl, more preferably methyl; m is 0, 1, 2, 3 or 4, preferably 0, 1 or 2, more preferably 0; n is 0, 1, 2 or 3, preferably 0, 1 or 2, more preferably 0; R" and R'" are independently of each other an unsubstituted or substituted $C_6$-$C_{24}$aryl group, an unsubstituted or substituted $C_1$-$C_{30}$heteroaryl group, an unsubstituted or substituted $C_1$-$C_{25}$alkyl group, an unsubstituted or substituted $C_7$-$C_{25}$aralkyl group, an unsubstituted or substituted $C_5$-$C_{12}$cycloalkyl group, —NR$^{15}$R$^{16}$, —OR$^{17}$, —SR$^{18}$, —SiR$^{19}$R$^{20}$R$^{21}$, —CN or halogen, preferably an unsubstituted or substituted $C_6$-$C_{24}$aryl group, an unsubstituted or substituted $C_1$-$C_{30}$heteroaryl group, an unsubstituted or substituted $C_1$-$C_{25}$alkyl group, an unsubstituted or substituted $C_7$-$C_{25}$aralkyl group, or an unsubstituted or substituted $C_5$-$C_{12}$cycloalkyl group, and the dotted line is a bonding site. Preferred heteroaryl groups are dibenzothiophenyl, diazadibenzothiophenyl, dibenzofuranyl, diazadibenzofuranyl, pyridyl, triazyl, pyrimidyl, quinoxalinyl, quinazolinyl, benzoquinazolinyl, which can be unsubstituted or substituted, or a group of formula (A).

$C_7$-$C_{25}$aralkyl, which optionally can be substituted, is for example benzyl, 2-benzyl-2-propyl, β-phenyl-ethyl, α,α- dimethylbenzyl, ω-phenyl-butyl, ω,ω-dimethyl-ω-phenyl-butyl, ω-phenyl-dodecyl, ω-phenyl-octadecyl, ω-phenyl-eicosyl or ω-phenyl-docosyl, preferably $C_7$-$C_{18}$aralkyl such as benzyl, 2-benzyl-2-propyl, β-phenyl-ethyl, α,α-dimethyl-benzyl, ω,ω-dimethyl-ω-phenyl-butyl, ω-phenyl-dodecyl or ω-phenyl-octadecyl, and particularly preferred $C_7$-$C_{12}$aralkyl such as benzyl, 2-benzyl-2-propyl, β-phenyl-ethyl, α,α-dimethylbenzyl, ω-phenyl-butyl, or ω,ω-dimethyl-ω-phenyl-butyl, in which both the aliphatic hydrocarbon group and aromatic hydrocarbon group may be unsubstituted or substituted. Preferred examples are benzyl, 2-phenylethyl, 3-phenyl propyl, naphthylethyl, naphthyl methyl, and cumyl.

$C_5$-$C_{12}$cycloalkyl, which optionally can be substituted, is for example cyclopentyl, cyclohexyl, cycloheptyl, cyclooctyl, cyclononyl, cyclodecyl, cycloundecyl, cyclododecyl, adamantyl, preferably cyclopentyl, cyclohexyl, cycloheptyl, or cyclooctyl, which may be unsubstituted or substituted.

The $C_6$-$C_{24}$arylene group is a divalent aromatic hydrocarbon group having 6 to 24 ring carbon atoms may be a non-condensed divalent aromatic hydrocarbon group or a condensed divalent aromatic hydrocarbon group. Specific examples thereof include phenylene group, naphthylene group, phenanthrylene group, biphenyl-diyl group, terphenyl-diyl group, quaterphenyl-diyl group, fluoranthen-diyl group, triphenylenylene-diyl group, phenanthrene-diyl group, fluorene-diyl group, spirofluorene-diyl group, 9,9-diphenylfluorene-diyl group, 9,9'-spirobi[9H-fluorene]-2-diyl group, 9,9-dimethylfluorene-diyl group, benzo[c]phenanthrene-diyl group, benzo[a]triphenylene-diyl group, naphtho[1,2-c]phenanthrene-diyl group, naphtho[1,2-a]triphenylenylene-diyl group, dibenzo[a,c]triphenylenylene-diyl group, and benzo[b]fluoranthene-diyl group, with phenylene group, naphthylene group, biphenyl-diyl group, terphenyl-diyl group, phenanthryl-diyl group, triphenyle-nylen-diyl group, fluorene-diyl group, spirobifluorene-diyl group, and fluoranthene-diyl group being preferred, and 1,2-phenylene group, 1,3-phenylene group, 1,4-phenylene group, 1,4-naphthylene group, 1,8-naphthylene group, 2,6-naphthylene group, 2,7-naphthylene group, biphenyl-2,2'-diyl group, biphenyl-2,3'-diyl group, biphenyl-2,4'-diyl group, biphenyl-2,5'-diyl group, biphenyl-2,6'-diyl group, biphenyl-3,3'-diyl group, biphenyl-3,4'-diyl group, biphenyl-3,5'-diyl group, biphenyl-3,6'-diyl group, biphenyl-4,4'-diyl group, biphenyl-4,5'-diyl group, biphenyl-4,6'-diyl group, biphenyl-5,5'-diyl group, biphenyl-5,6'-diyl group, biphenyl-6,6'-diyl group, phenanthrene-9,10-diyl group, phenanthrene-2,3-diyl group, phenanthrene-2,7-diyl group, phenanthrene-2,8-diyl group, phenanthrene-2,6-diyl group, phenanthrene-2,9-diyl group, phenanthrene-2,10-diyl group, phenanthrene-3,9-diyl group, phenanthrene-3,10-diyl group, triphenylene-2,3-diyl group, triphenylene-2,5-diyl group, triphenylene-2,6-diyl group, triphenylene-2,7-diyl group, triphenylene-2,8-diyl group, 9,9-dimethylfluorene-2,7-diyl group, 9,9-dimethylfluorene-3,7-diyl group, 9,9-dimethyl-fluorene-1,4-diyl group, fluoranthene-3,9-diyl group, fluoranthene-3,8-diyl group, fluoranthene-3,4-diyl group, fluoranthene-3,5-diyl group, fluoranthene-3,6-diyl group, fluoranthene-2,9-diyl group, fluoranthene-2,8-diyl group, fluoranthene-2,4-diyl group, fluoranthene-2,5-diyl group, fluoranthene-2,6-diyl group, fluoranthene-1,9-diyl group, fluoranthene-1,8-diyl group, fluoranthene-1,4-diyl group, fluoranthene-1,5-diyl group, fluoranthene-1,6-diyl group being more preferred. The arylene group is substituted or unsubstituted.

The $C_1$-$C_{30}$heteroarylene group is a divalent heterocyclic group having 1 to 30 ring carbon atoms may be a non-condensed heterocyclic group or a condensed heterocyclic group. Specific examples thereof include the divalent residues of pyrrole ring, isoindole ring, benzofuran ring, isobenzofuran ring, dibenzothiophene ring, isoquinoline ring, quinoxaline ring, phenanthridine ring, phenanthroline ring, pyridine ring, pyrazine ring, pyrimidine ring, pyridazine ring, triazine ring, indole ring, quinoline ring, acridine ring, pyrrolidine ring, dioxane ring, piperidine ring, morpholine ring, piperazine ring, carbazole ring, furan ring, thiophene ring, oxazole ring, oxadiazole ring, benzoxazole ring, thiazole ring, thiadiazole ring, benzothiazole ring, triazole ring, tetrazole ring, imidazole ring, benzimidazole ring, pyran ring, dibenzofuran ring, and benzo[c]dibenzofuran ring, and the divalent residues of derivatives of these rings, with the divalent residues of dibenzofuran ring, carbazole ring, dibenzothiophene ring, and derivatives of these divalent rings being preferred, and the dibenzofuran-diyl group, 9-phenylcarbazole-diyl group and dibenzothiophene-diyl group being more preferred. The heteroarylene group is substituted or unsubstituted.

The five or six membered aliphatic, aromatic or heteroaromatic ring is a $C_5$-$C_6$cycloalkyl ring, which optionally can be substituted, i.e. cyclopentyl, or cyclohexyl, which may be unsubstituted or substituted; a $C_6$aryl, which optionally can be substituted, i.e. phenyl which may be unsubstituted or substituted or a $C_3$-$C_6$heteroaryl, which optionally can be substituted, wherein nitrogen, oxygen or sulfur are the possible hetero atoms, e.g. furanyl, pyrrolyl, thiophenyl, imidazolyl, pyrazolyl, oxazolyl, isoxazolyl, thiazolyl, pyridinyl, pyrazinyl, pyrimidinyl, triazinyl or pyridazinyl, which may be unsubstituted or substituted.

In the case of the expression "unsubstituted or substituted" used within the description of the present application, preferred substituents and a preferred number of substituents are mentioned below. An unsubstituted group exclusively comprises hydrogen at its substitutable position(s).

Possible preferred optional substituents of the above-mentioned groups are $C_1$-$C_{18}$alkyl, a hydroxyl group, a mercapto group, $C_1$-$C_{18}$alkoxy, $C_1$-$C_8$alkylthio, halogen, halo-$C_1$-$C_8$alkyl, $C_6$-$C_{24}$aryl, $C_2$-$C_{30}$heteroaryl, or a cyano group. Preferred groups are mentioned above. Particularly preferred are methyl, ethyl, n-propyl, isopropyl, n-butyl, sec-butyl, isobutyl, tert-butyl, methoxy, ethoxy, n-propoxy, isopropoxy, n-butoxy, sec-butoxy, isobutoxy, tert-butoxy, phenyl, naphthyl, especially 1-naphthyl, or 2-naphthyl, phenanthryl, or fluoranthene-yl, Preferred heteroaryl groups are dibenzothiophenyl, azadibenzothiophenyl, diazadibenzothiophenyl, dibenzofuranyl, azadibenzofuranyl, diazadibenzofuranyl, pyridyl, triazyl, pyrimidyl, quinoxalinyl, quinazolinyl, benzoquinazolinyl, CN, or a group of formula (A) as defined above.

The optional substituents mentioned above may be further substituted by one or more of the optional substituents mentioned above.

The number of the optional substituents depends on the group which is substituted by said substituent(s). Preferred are 1, 2, 3 or 4 substituents, more preferred are 1, 2 or 3 substituents, most preferred are 1 or 2 substituents. In a further preferred embodiment, the groups mentioned above are unsubstituted.

The "carbon number of a to b" in the expression of "X group having a to b carbon atoms" is the carbon number of the unsubstituted X group and does not include the carbon atom(s) of an optional substituent.

The hydrogen atom referred to herein includes isotopes different from neutron numbers, i.e., light hydrogen (protium), heavy hydrogen (deuterium) and tritium. Therefore, one or more or all of the hydrogen atoms in the residues mentioned above and below may be replaced by protium, deuterium or tritium, preferably by deuterium.

In the specification, the term "ring carbon atoms" refers to the number of carbon atoms among atoms forming a ring of a compound in which atoms are bonded to form a ring (e.g. monocyclic compound, fused cyclic compound, cross-linked compound, carbocyclic compound, and heterocyclic compound). When the ring is substituted by a substituent, the carbon atoms included in the substituent are not counted as the ring carbon atoms. The same applies to the "ring carbon atoms" described later, except as otherwise mentioned. For example, a benzene ring has six ring carbon atoms, a naphthalene ring has ten ring carbon atoms, pyridine ring has five ring carbon atoms. Further, when a benzene ring and naphthalene ring are, for example, substituted by an alkyl group, the number of carbon atoms of the alkyl group is not included in the ring carbon atoms. Further, when, for example, a substituent in a form of a fluorene ring (including spiro fluorene ring) is bonded to a fluorene ring, the number of carbon atoms of the substituent in the form of fluorene ring are not counted as the number of ring carbon atoms.

In the specification, the term "ring atoms" refers to the number of atoms among atoms forming a ring of a compound in which atoms are bonded to form the ring (e.g. monocyclic compound, fused cyclic compound, cross-linked compound, carbocyclic compound, and heterocyclic compound). Atom(s) not forming a ring and the atoms included in a substituent when the ring is substituted by a substituent are not counted as ring atoms. The same applies to the "ring atoms" described later, except as otherwise mentioned. For example, a pyridine ring has six ring atoms, a quinazoline ring has ten ring atoms, a furan ring has five ring atoms. The number of hydrogen atoms and atoms of a substituent bonded to the carbon atoms of the pyridine ring and quinazoline ring are not counted as the ring atoms.

The Compounds of Formula (I)

The present invention relates to polycyclic compounds of the general formula (I)

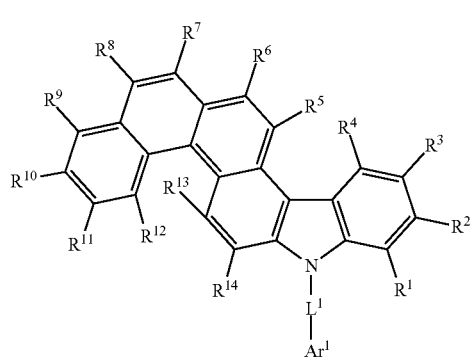

(I)

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $L^1$ and $Ar^1$ have the meanings as mentioned above.

$Ar^1$ is preferably an unsubstituted or substituted $C_6$-$C_{16}$aryl group, more preferably selected from the group consisting of an unsubstituted or substituted phenyl group, an unsubstituted or substituted naphthyl group, an unsubstituted or substituted phenanthrene group, an unsubstituted or substituted fluoranthene group, or an unsubstituted or substituted $C_3$-$C_{15}$heteroaryl group, more preferably selected from the group consisting of an unsubstituted or substituted quinoxaline group, an unsubstituted or substituted quinazoline group, an unsubstituted or substituted benzoquinazoline group, an unsubstituted or substituted diazadibenzofuran group, an unsubstituted or substituted diazadibenzothiophene group, an unsubstituted or substituted pyridine group, an unsubstituted or substituted pyrimidine group, an unsubstituted or substituted triazine group, an unsubstituted or substituted dibenzofuran group, an unsubstituted or substituted dibenzothiophene group, an unsubstituted or substituted carbazole group, and a group of formula (A)

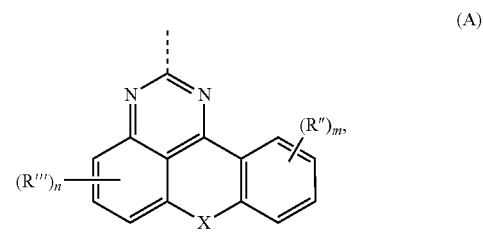

(A)

wherein X is O, NR, $CR'_2$ or S, R is an unsubstituted or substituted $C_6$-$C_{10}$ aryl group, preferably unsubstituted or substituted phenyl, more preferably unsubstituted phenyl; R' is $C_1$-$C_4$-alkyl, preferably methyl, ethyl, n-propyl, iso-propyl, n-butyl, iso-butyl or tert.-butyl, more preferably methyl; m is 0, 1, 2, 3 or 4, preferably 0, 1 or 2, more preferably 0; n is 0, 1, 2 or 3, preferably 0, 1 or 2, more preferably 0; R" and R'" are independently of each other an unsubstituted or substituted $C_6$-$C_{24}$aryl group, an unsubstituted or substituted $C_1$-$C_{30}$heteroaryl group, an unsubstituted or substituted $C_1$-$C_{25}$alkyl group, an unsubstituted or substituted $C_7$-$C_{25}$aralkyl group, an unsubstituted or substituted $C_5$-$C_{12}$cycloalkyl group, —$NR^{15}R^{16}$, —$OR^{17}$, —$SR^{18}$, —$SiR^{19}R^{20}R^{21}$, —CN or halogen, preferably an unsubstituted or substituted $C_6$-$C_{24}$aryl group, an unsubstituted or substituted $C_1$-$C_{30}$heteroaryl group, an unsubstituted or substituted $C_1$-$C_{25}$alkyl group, an unsubstituted or substituted $C_7$-$C_{25}$aralkyl group, or an unsubstituted or substituted $C_5$-$C_{12}$cycloalkyl group, and the dotted line is a bonding site.

More preferably $Ar^1$ is selected from the group consisting of an unsubstituted or substituted fluoranthene group, an unsubstituted or substituted quinoxaline group, an unsubstituted or substituted quinazoline group, an unsubstituted or substituted benzoquinazoline group, an unsubstituted or substituted triazine group, an unsubstituted or substituted pyrimidine group, an unsubstituted or substituted diazadibenzofuran group, an unsubstituted or substituted diazadibenzothiophene group, and a group of formula (A)

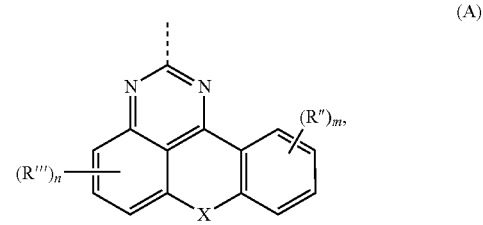

(A)

wherein X is O, NR, $CR'_2$ or S, R is an unsubstituted or substituted $C_6$-$C_{10}$ aryl group, preferably unsubstituted or substituted phenyl, more preferably unsubstituted phenyl; R'
is $C_1$-$C_4$-alkyl, preferably methyl, ethyl, n-propyl, iso-propyl, n-butyl, iso-butyl or tert.-butyl, more preferably methyl;
m is 0, 1, 2, 3 or 4, preferably 0, 1 or 2, more preferably 0;
n is 0, 1, 2 or 3, preferably 0, 1 or 2, more preferably 0; R"
and R''' are independently of each other an unsubstituted or
substituted $C_6$-$C_{24}$aryl group, an unsubstituted or substituted
$C_1$-$C_{30}$heteroaryl group, an unsubstituted or substituted
$C_1$-$C_{25}$alkyl group, an unsubstituted or substituted
$C_7$-$C_{25}$aralkyl group, an unsubstituted or substituted
$C_5$-$C_{12}$cycloalkyl group, —$NR^{15}R^{16}$, —$OR^{17}$,
—$SR^{18}R^{19}R^{20}R^{21}$, —CN or halogen, preferably an unsubstituted or substituted $C_6$-$C_{24}$aryl group, an unsubstituted or
substituted $C_1$-$C_{30}$heteroaryl group, an unsubstituted or substituted $C_1$-$C_{25}$alkyl group, an unsubstituted or substituted
$C_7$-$C_{25}$aralkyl group, or an unsubstituted or substituted
$C_5$-$C_{12}$cycloalkyl group, and the dotted line is a bonding
site.

Most preferably $Ar^1$ is an unsubstituted or substituted
fluoranthene group, an unsubstituted or substituted quinazoline group, an unsubstituted or substituted benzoquinazoline
group, or a group of formula (A)

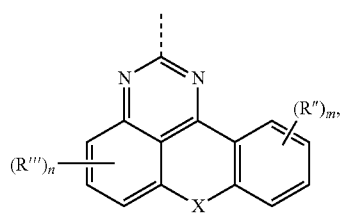

(A)

wherein X is O, NR, $CR'_2$ or S, R is an unsubstituted or
substituted $C_6$-$C_{10}$ aryl group, preferably unsubstituted or
substituted phenyl, more preferably unsubstituted phenyl; R'
is $C_1$-$C_4$-alkyl, preferably methyl, ethyl, n-propyl, iso-propyl, n-butyl, iso-butyl or tert.-butyl, more preferably methyl;
m is 0, 1, 2, 3 or 4, preferably 0, 1 or 2, more preferably 0;
n is 0, 1, 2 or 3, preferably 0, 1 or 2, more preferably 0; R"
and R''' are are independently of each other an unsubstituted
or substituted $C_6$-$C_{24}$aryl group, an unsubstituted or substituted $C_1$-$C_{30}$heteroaryl group, an unsubstituted or substituted $C_1$-$C_{25}$alkyl group, an unsubstituted or substituted
$C_7$-$C_{25}$aralkyl group, an unsubstituted or substituted
$C_5$-$C_{12}$cycloalkyl group, —$NR^{15}R^{16}$, —$OR^{17}$, —$SR^{18}$,
—$SiR^{19}R^{20}R^{21}$, —CN or halogen, preferably an unsubstituted or substituted $C_6$-$C_{24}$aryl group, an unsubstituted or
substituted $C_1$-$C_{30}$heteroaryl group, an unsubstituted or substituted $C_1$-$C_{25}$alkyl group, an unsubstituted or substituted
$C_7$-$C_{25}$aralkyl group, or an unsubstituted or substituted
$C_5$-$C_{12}$cycloalkyl group, and the dotted line is a bonding
site.

Further most preferably, $Ar^1$ is an unsubstituted fluoranthene group, an unsubstituted or substituted quinazoline
group, for example a phenyl substituted quinazoline group
or a carbazolyl substituted quinazoline, an unsubstituted or
substituted benzoquinazoline group, for example a phenyl
substituted benzoquinazoline group or a carbazolyl substituted benzoquinazoline, or a group of formula (A')

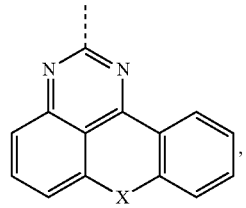

(A')

wherein X is O, N-phenyl, C(methyl)$_2$ or S, preferably O,
and the dotted line is a bonding site.

$L_1$ is preferably a direct bond, an unsubstituted or substituted $C_6$-$C_{13}$arylene group, preferably selected from the
group consisting of a divalent unsubstituted or substituted
phenyl group, a divalent unsubstituted or substituted naphthyl group, a divalent unsubstituted or substituted biphenyl
group, and a divalent unsubstituted or substituted fluorene
group, or an unsubstituted or substituted
$C_3$-$C_{12}$heteroarylene group, preferably selected from the
group consisting of a divalent unsubstituted or substituted
dibenzofuran group and a divalent unsubstituted or substituted dibenzothiophene group, more preferably $L_1$ is a
divalent unsubstituted phenyl group, for example a 1,2-, 1,3
or 1,4-phenylene group, or a direct bond, most preferably $L_1$
is a direct bond.

In a preferred embodiment of the present invention,
$L^1$ is a direct bond, an unsubstituted or substituted
$C_6$-$C_{13}$arylene group, preferably selected from the group
consisting of a divalent unsubstituted or substituted phenyl
group, a divalent unsubstituted or substituted naphthyl
group, a divalent unsubstituted or substituted biphenyl
group, and a divalent unsubstituted or substituted fluorene
group, a divalent unsubstituted or substituted dibenzofuran
group and a divalent unsubstituted or substituted dibenzothiophene group, more preferably $L_1$ is a divalent unsubstituted phenyl group, for example a 1,2-, 1,3 or 1,4-phenylene
group, or a direct bond, most preferably $L_1$ is a direct bond;
and $Ar^1$ is an unsubstituted or substituted fluoranthene group,
or an unsubstituted or substituted quinazoline group, an
unsubstituted or substituted benzoquinazoline group, or a
group of formula (A)

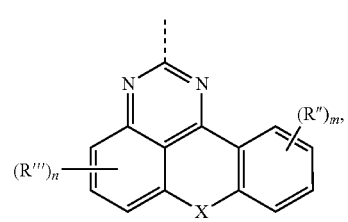

(A)

wherein X is O, NR, $CR'_2$ or S, R is an unsubstituted or
substituted $C_6$-$C_{10}$ aryl group, preferably unsubstituted or
substituted phenyl, more preferably unsubstituted phenyl; R'
is $C_1$-$C_4$-alkyl, preferably methyl, ethyl, n-propyl, iso-propyl, n-butyl, iso-butyl or tert.-butyl, more preferably methyl;
m is 0, 1, 2, 3 or 4, preferably 0, 1 or 2, more preferably 0;
n is 0, 1, 2 or 3, preferably 0, 1 or 2, more preferably 0; R"
and R''' are independently of each other an unsubstituted or
substituted $C_6$-$C_{24}$aryl group, an unsubstituted or substituted $C_1$-$C_{30}$heteroaryl group, an unsubstituted or substituted $C_1$-$C_{25}$alkyl group, an unsubstituted or substituted $C_7$-$C_{25}$aralkyl group, an unsubstituted or substituted $C_5$-$C_{12}$cycloalkyl group, —$NR^{15}R^{16}$, —$OR^{17}$, —$SR^{18}$, —$SiR^{19}R^{20}R^{21}$, —CN or halogen, preferably an unsubstituted or substituted $C_6$-$C_{24}$aryl group, an unsubstituted or substituted $C_1$-$C_{30}$heteroaryl group, an unsubstituted or substituted $C_1$-$C_{25}$alkyl group, an unsubstituted or substituted $C_7$-$C_{25}$aralkyl group, or an unsubstituted or substituted $C_5$-$C_{12}$cycloalkyl group, and the dotted line is a bonding site; preferably, $Ar^1$ is an unsubstituted fluoranthene group, an unsubstituted or substituted quinazoline group, for example a 4-phenyl-quinazoline group, or a group of formula (A')

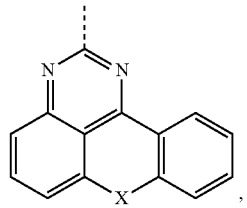

(A')

wherein X is O, N-phenyl, C(methyl)$_2$ or S, preferably O, and the dotted line is a bonding site.

$R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ are preferably independently of each other hydrogen, an unsubstituted or substituted $C_6$-$C_{10}$aryl group, an unsubstituted or substituted $C_3$-$C_{13}$heteroaryl group, an unsubstituted or substituted $C_1$-$C_8$alkyl group, —CN or halogen;

wherein two of $R^1$, $R^2$, $R^3$, $R^4$, $R^5$, $R^6$, $R^7$, $R^8$, $R^9$, $R^{10}$, $R^{11}$ and $R^{12}$, if present at adjacent carbon atoms, preferably $R^7$ and $R^8$, together may form an unsubstituted or substituted $C_6$-$C_{18}$aryl ring, preferably an unsubstituted or substituted phenyl ring.

More preferably, $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ are independently of each other hydrogen, an unsubstituted or substituted phenyl group, or an unsubstituted or substituted naphthyl group, wherein two of $R^1$, $R^2$, $R^3$, $R^4$, $R^5$, $R^6$, $R^7$, $R^8$, $R^9$, $R^{10}$, $R^{11}$ and $R^{12}$, if present at adjacent carbon atoms, preferably $R^7$ and $R^8$, together may form an unsubstituted or substituted $C_6$-$C_{18}$aryl ring, preferably an unsubstituted or substituted phenyl ring.

Most preferably, 0, 1 or 2 of the residues $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ are an unsubstituted or substituted $C_6$-$C_{10}$aryl group, an unsubstituted or substituted $C_3$-$C_{13}$heteroaryl group, an unsubstituted or substituted $C_1$-$C_8$alkyl group, —CN or halogen, preferably an unsubstituted or substituted phenyl group, or an unsubstituted or substituted naphthyl group, and the remaining residues $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ are hydrogen, wherein two of $R^1$, $R^2$, $R^3$, $R^4$, $R^5$, $R^6$, $R^7$, $R^8$, $R^9$, $R^{10}$, $R^{11}$ and $R^{12}$, if present at adjacent carbon atoms, preferably $R^7$ and $R^8$, together may form an unsubstituted or substituted $C_6$-$C_{18}$aryl ring, preferably an unsubstituted or substituted phenyl ring.

Further most preferably, $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ are hydrogen, wherein two of $R^1$, $R^2$, $R^3$, $R^4$, $R^5$, $R^6$, $R^7$, $R^8$, $R^9$, $R^{10}$, $R^{11}$ and $R^{12}$, if present at adjacent carbon atoms, preferably $R^7$ and $R^8$, together may form an unsubstituted phenyl ring.

The polycyclic compound of the present invention is therefore most preferably represented by one of the following formula (Ia) or (Ib):

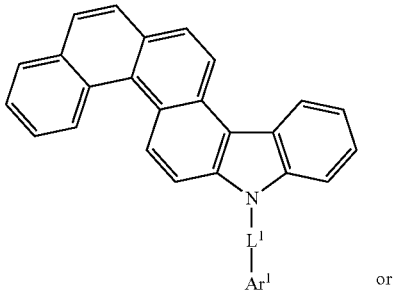

(Ia)

or

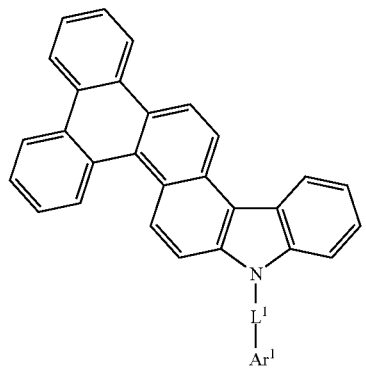

(Ib)

wherein $L^1$ and $Ar^1$ are defined above.

Most preferably, in the compounds of formulae (Ia) and (Ib), $L^1$ and $Ar^1$ are:

$L^1$ is a direct bond, an unsubstituted or substituted $C_6$-$C_{13}$arylene group, preferably selected from the group consisting of a divalent unsubstituted or substituted phenyl group, a divalent unsubstituted or substituted naphthyl group, a divalent unsubstituted or substituted biphenyl group, and a divalent unsubstituted or substituted fluorene group, a divalent unsubstituted or substituted dibenzofuran group and a divalent unsubstituted or substituted dibenzothiophene group, more preferably $L_1$ is a divalent unsubstituted phenyl group, for example a 1,2-, 1,3- or 1,4-phenylene group, or a direct bond, most preferably $L_1$ is a direct bond; and Ar¹ is an unsubstituted or substituted fluoranthene group, or an unsubstituted or substituted quinazoline group, an unsubstituted or substituted benzoquinazoline group, or a group of formula (A)

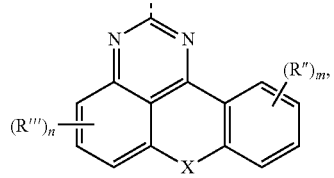
(A)

wherein X is O, NR, CR'$_2$ or S, R is an unsubstituted or substituted $C_6$-$C_{10}$ aryl group, preferably unsubstituted or substituted phenyl, more preferably unsubstituted phenyl; R' is $C_1$-$C_4$-alkyl, preferably methyl, ethyl, n-propyl, iso-propyl, n-butyl, iso-butyl or tert.-butyl, more preferably methyl; m is 0, 1, 2, 3 or 4, preferably 0, 1 or 2, more preferably 0; n is 0, 1, 2 or 3, preferably 0, 1 or 2, more preferably 0; R" and R''' are independently of each other an unsubstituted or substituted $C_6$-$C_{24}$aryl group, an unsubstituted or substituted $C_1$-$C_{30}$heteroaryl group, an unsubstituted or substituted $C_1$-$C_{25}$alkyl group, an unsubstituted or substituted $C_7$-$C_{25}$aralkyl group, an unsubstituted or substituted $C_5$-$C_{12}$cycloalkyl group, —NR$^{15}$R$^{16}$, —OR$^{17}$, —SR$^{18}$, —SiR$^{19}$R$^{20}$R$^{21}$, —CN or halogen, preferably an unsubstituted or substituted $C_6$-$C_{24}$aryl group, an unsubstituted or substituted $C_1$-$C_{30}$heteroaryl group, an unsubstituted or substituted $C_1$-$C_{25}$alkyl group, an unsubstituted or substituted $C_7$-$C_{25}$aralkyl group, or an unsubstituted or substituted $C_5$-$C_{12}$cycloalkyl group, and the dotted line is a bonding site; preferably, Ar¹ is an unsubstituted fluoranthene group, an unsubstituted or substituted quinazoline group, for example a 4-phenyl-quinazoline group, or a group of formula (A')

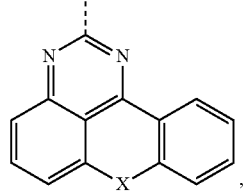
(A')

wherein X is O, N-phenyl, C(methyl)$_2$ or S, preferably O, and the dotted line is a bonding site.

Especially most preferably, R¹, R², R³, R⁴, R⁵, R⁶, R⁷, R⁸, R⁹, R¹⁰, R¹¹, R¹², R¹³ and R¹⁴ are hydrogen.

Particularly preferred are the following compounds:
Compounds of formulae (II), (III), (IV) or (V):

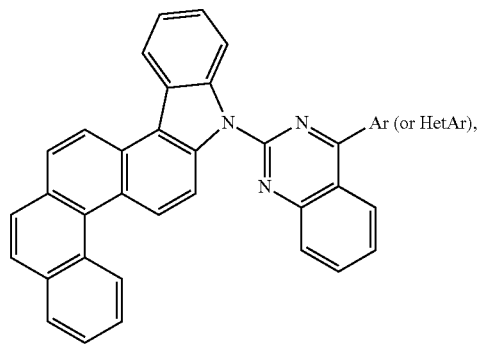
(II)

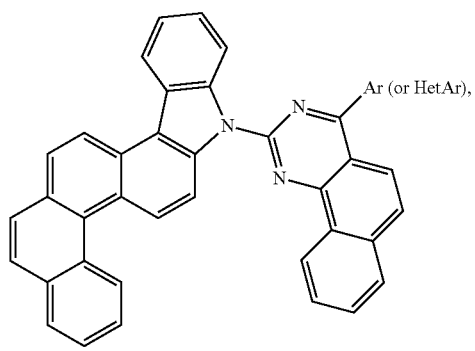
(III)

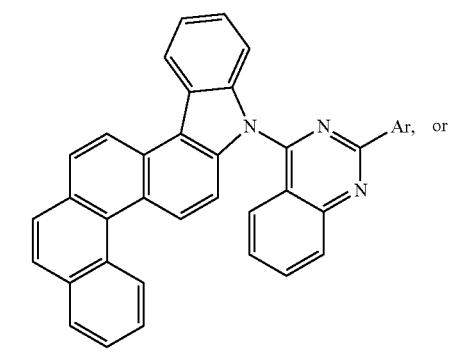
(IV)

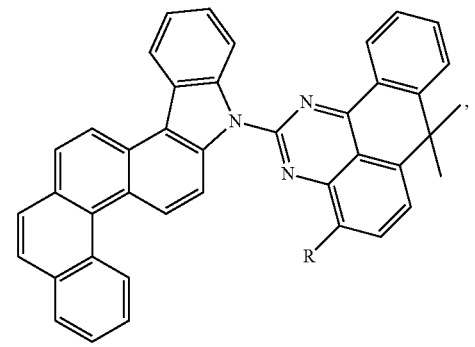
(V)

wherein

Ar is unsubstituted or substituted phenyl, unsubstituted or substituted biphenyl, unsubstituted or substituted naphthyl, unsubstituted or substituted phenanthryl, preferably unsubstituted phenyl, unsubstituted biphenyl, unsubstituted naphthyl, unsubstituted phenanthryl;

HetAr is unsubstituted or substituted carbazolyl, unsubstituted or substituted dibenzofuranyl, unsubstituted or substituted dibenzothiophenyl, preferably unsubstituted carbazolyl, unsubstituted dibenzofuranyl, unsubstituted dibenzothiophenyl;

X is O, N-phenyl, C(methyl)$_2$ or S, preferably O;

R is hydrogen or phenyl, preferably hydrogen.

Examples for preferred compounds of formulae (II), (III), (IV) and (V) are shown below:

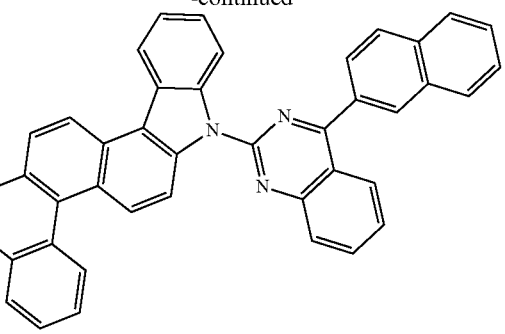

-continued

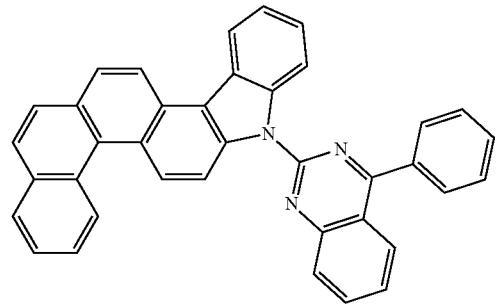

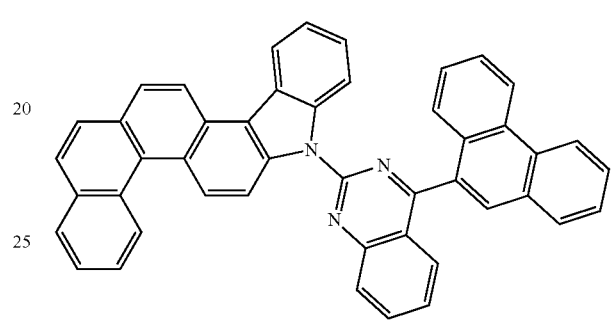

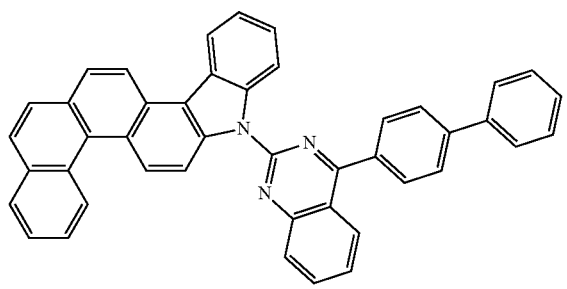

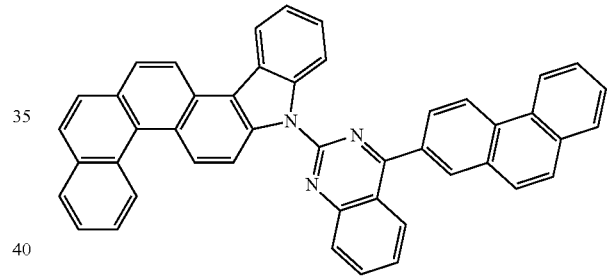

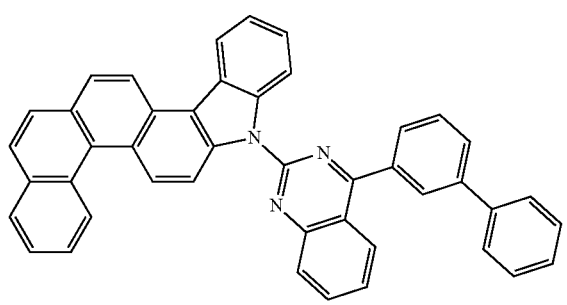

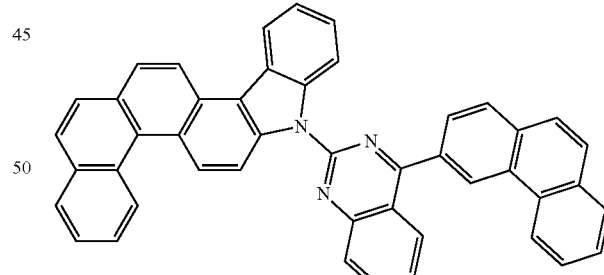

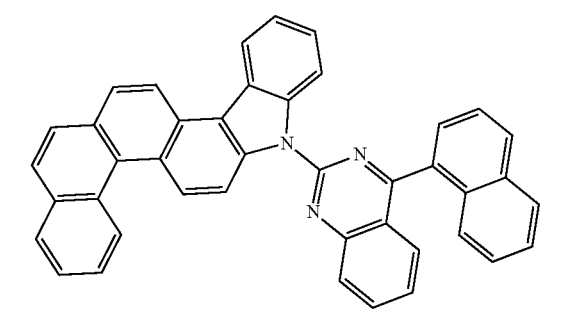

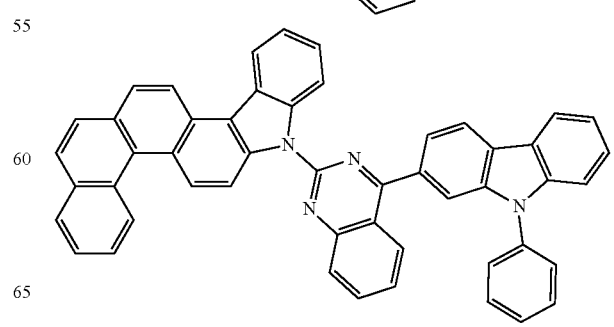

21
-continued
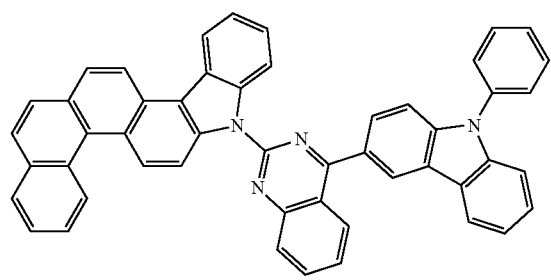
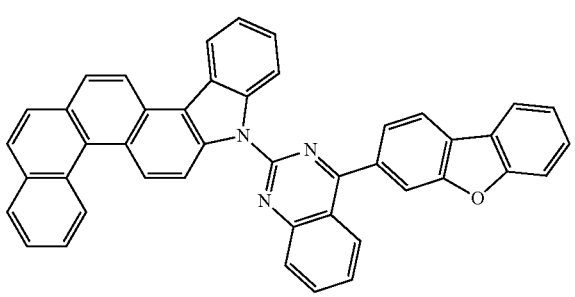
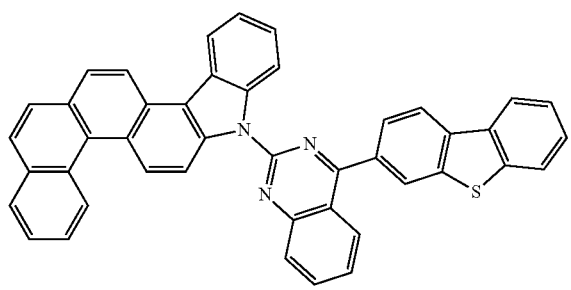
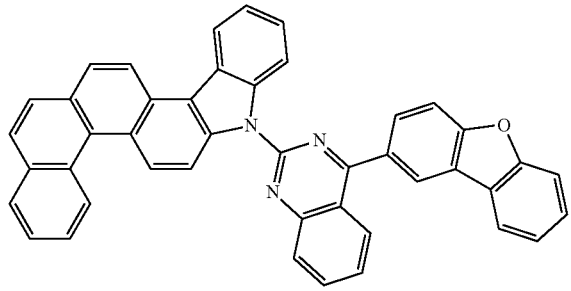
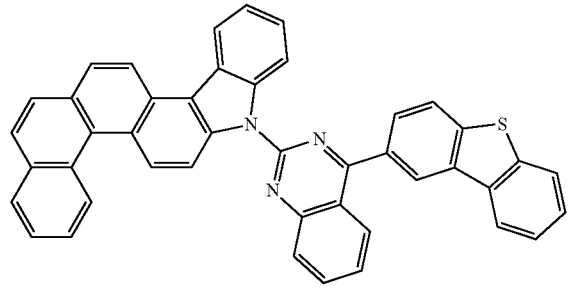
22
-continued
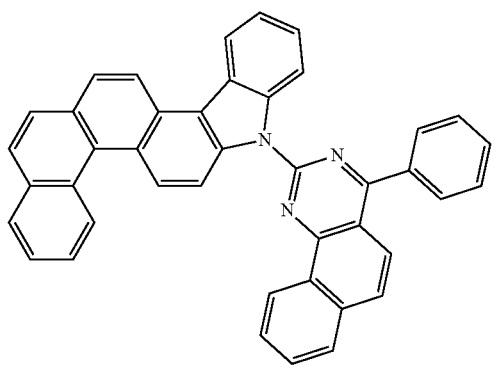
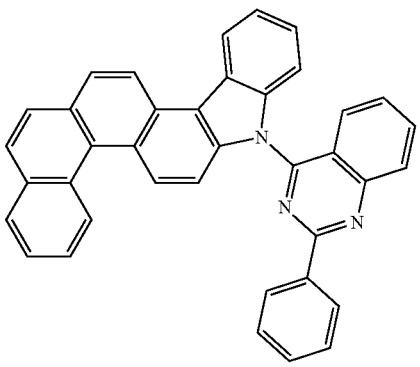
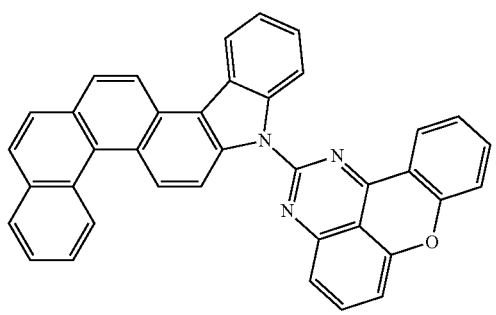
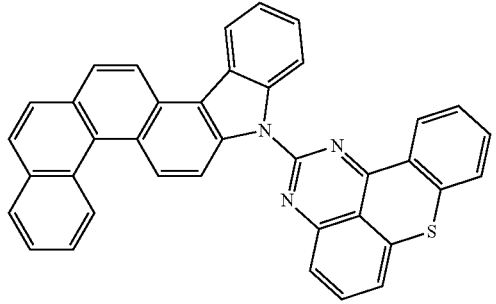
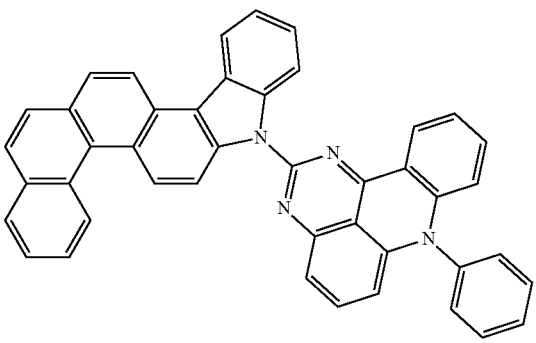

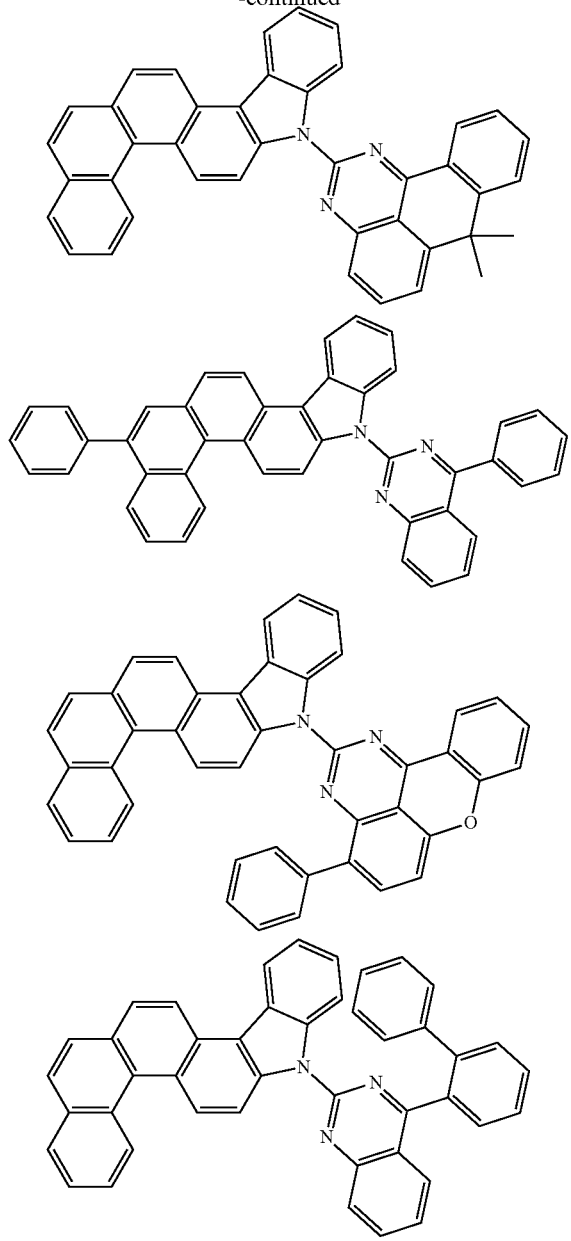

Compounds of formulae (VI), (VII), (VIII) or (IX):

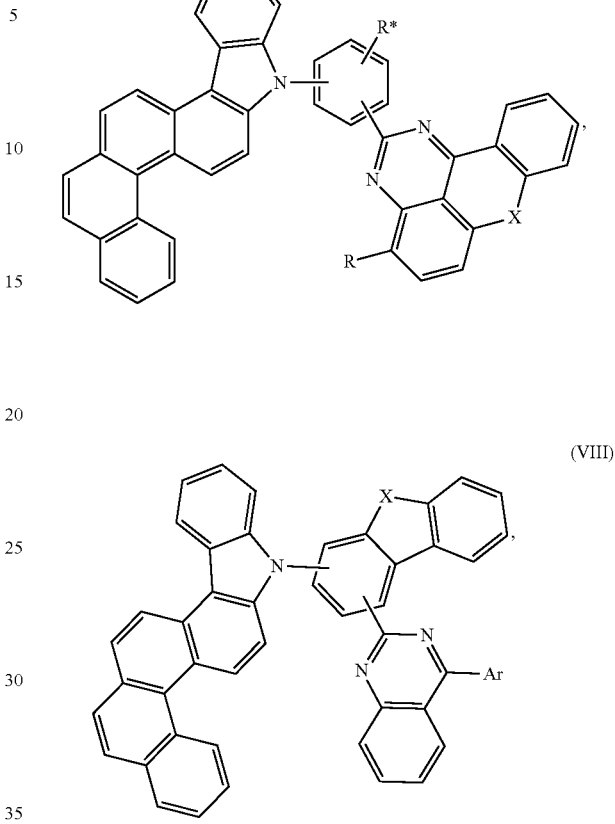

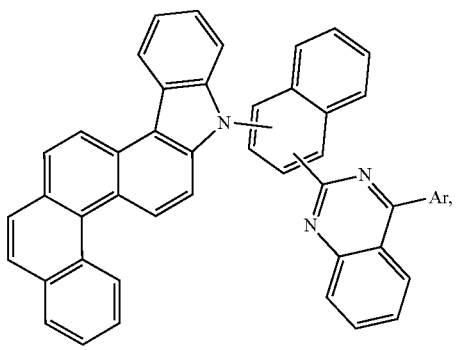

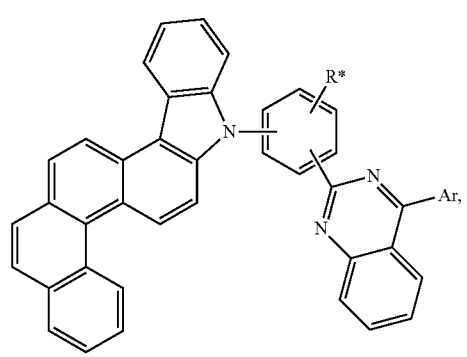

wherein

Ar is unsubstituted or substituted phenyl or unsubstituted or substituted biphenyl, preferably unsubstituted phenyl or unsubstituted biphenyl;

X is O, N-phenyl, C(methyl)$_2$ or S, preferably O;

R is hydrogen or unsubstituted or substituted phenyl, preferably hydrogen or unsubstituted phenyl, more preferably hydrogen;

R* is hydrogen or unsubstituted or substituted phenyl, preferably hydrogen or unsubstituted phenyl.

Examples for preferred compounds of formulae (VI), (VII), (VIII) and (IX) are shown below:
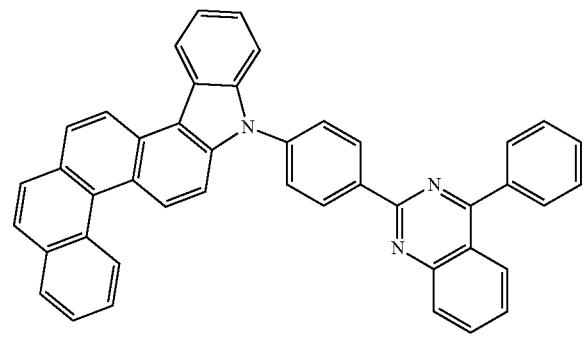
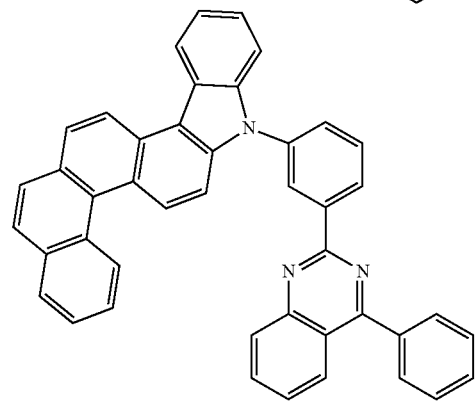
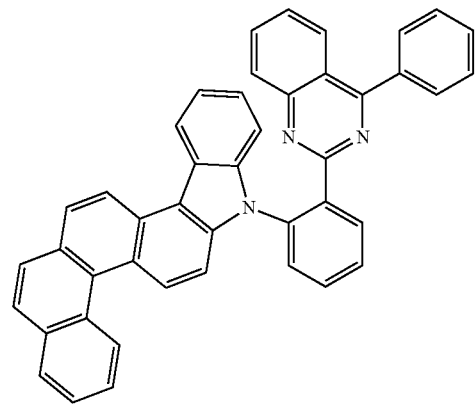
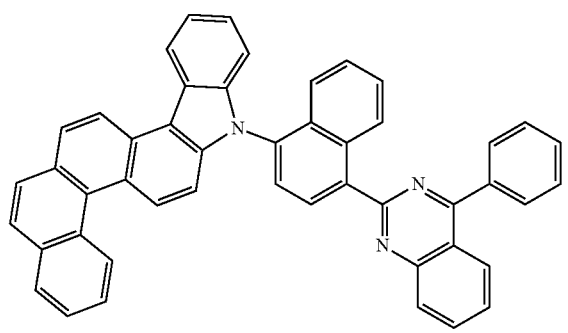
-continued
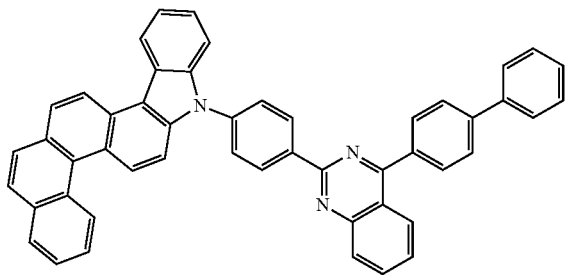
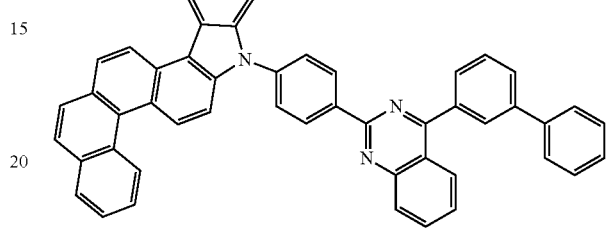
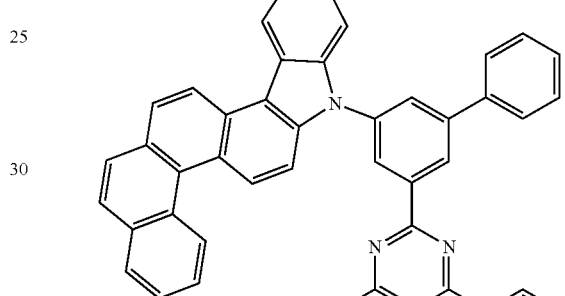
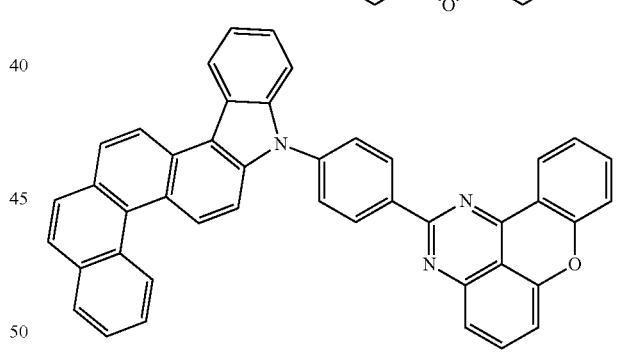
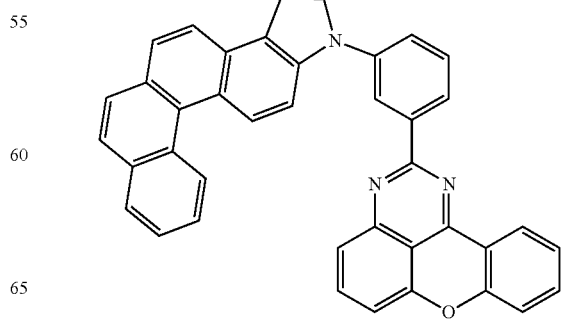

-continued
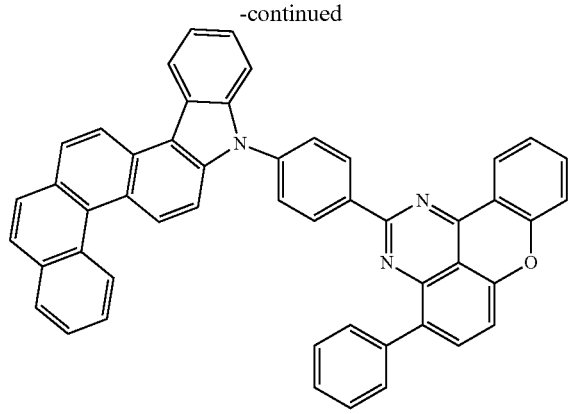
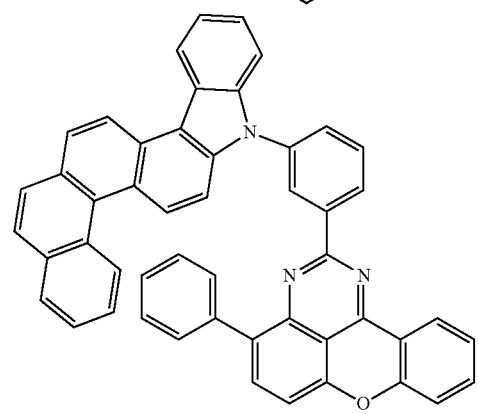
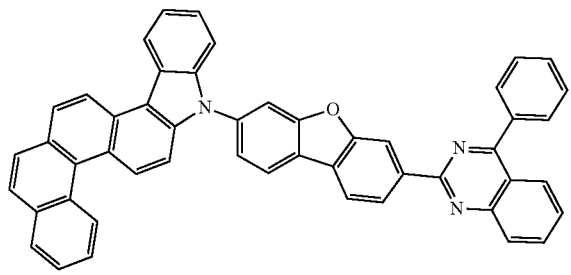
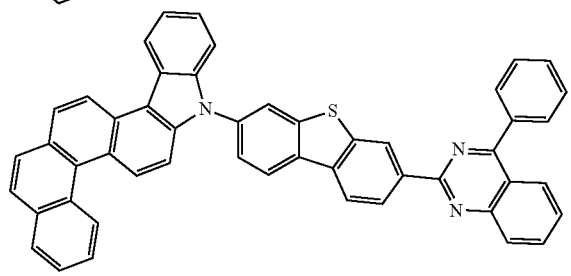
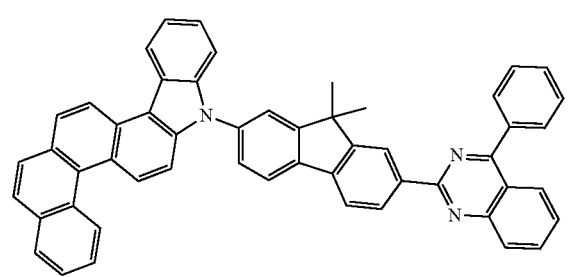
Compounds of formulae (X) and (XI):
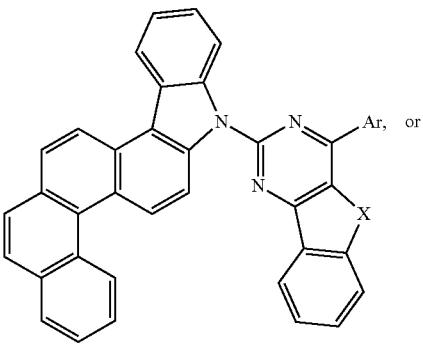
(X)
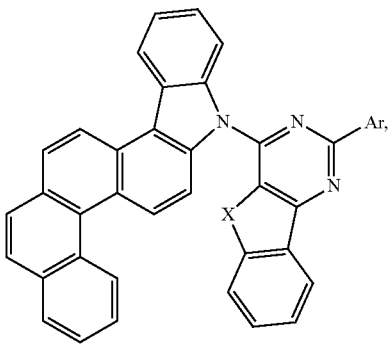
(XI)
wherein
Ar is unsubstituted or substituted phenyl or unsubstituted or substituted naphthyl, preferably unsubstituted phenyl or unsubstituted naphthyl; and X is O or S, preferably O.
Examples for preferred compounds of formulae (X) and (XI) are shown below:
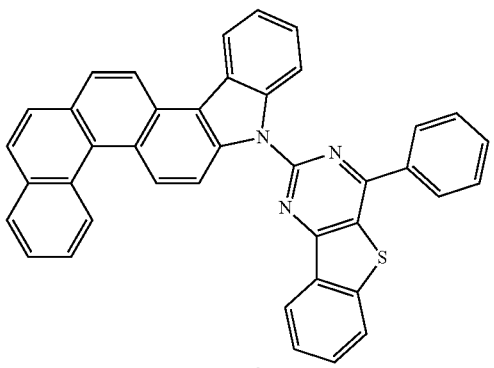
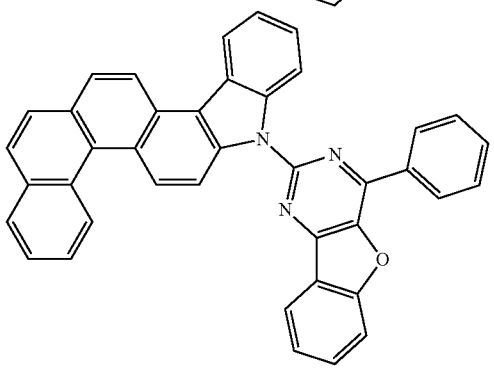

-continued
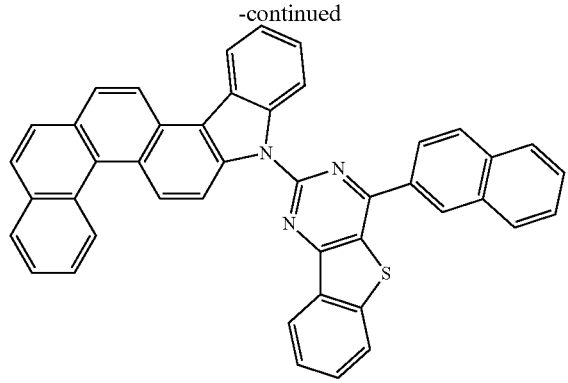
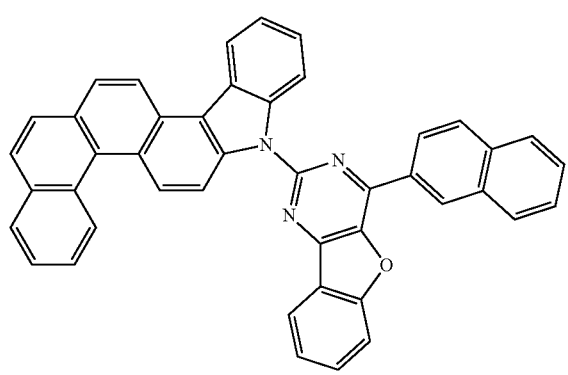
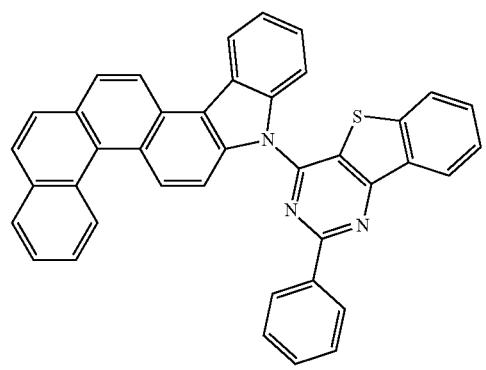
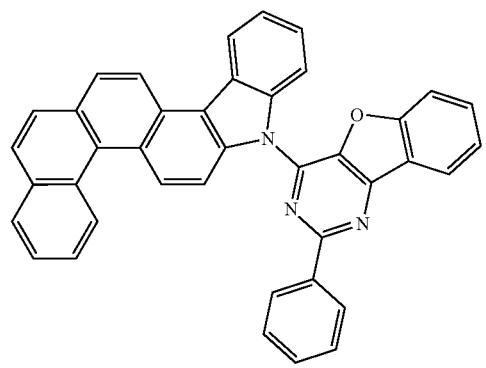
A compound of formula (XII):
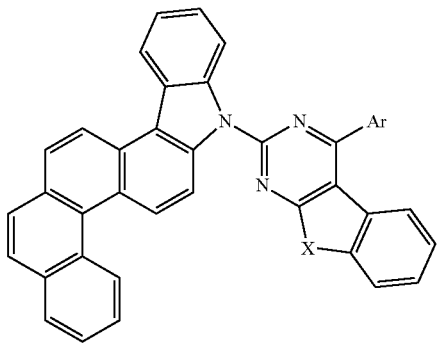
(XII)
wherein
X is O, N-phenyl, C(methyl)₂ or S, preferably O,
Ar is unsubstituted or substituted phenyl or unsubstituted or substituted naphthyl, preferably unsubstituted phenyl.
Examples for preferred compounds of formula (XII) are shown below:
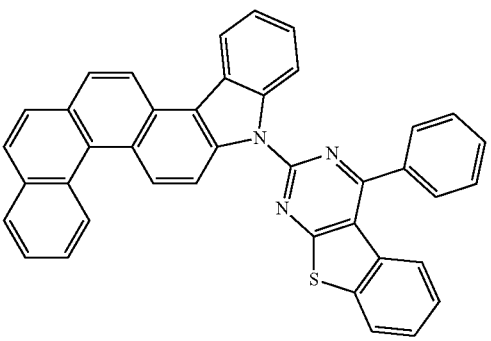
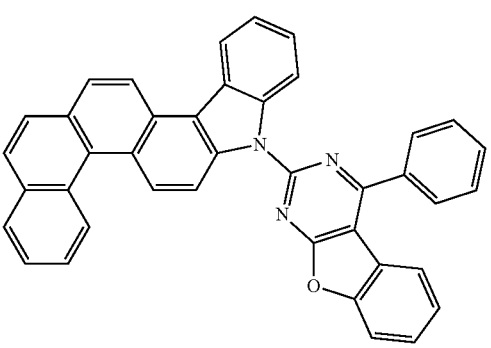

A compound of formula (XIII):

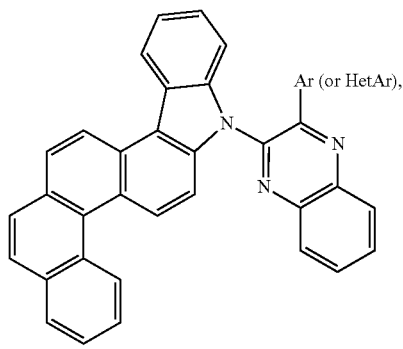

(XIII)

wherein

Ar is unsubstituted or substituted phenyl, unsubstituted or substituted biphenyl or unsubstituted or substituted naphthyl, preferably unsubstituted phenyl, unsubstituted biphenyl or unsubstituted naphthyl;

HetAr is unsubstituted or substituted dibenzofuranyl or unsubstituted or substituted dibenzothiophenyl, preferably unsubstituted dibenzofuranyl or unsubstituted dibenzothiophenyl.

Examples for preferred compounds of formula (XIII) are shown below:

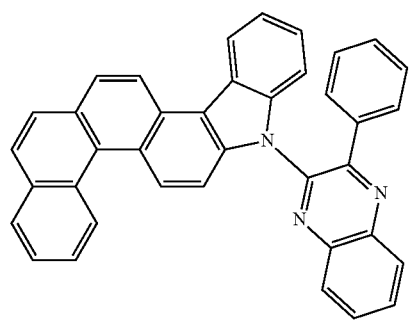

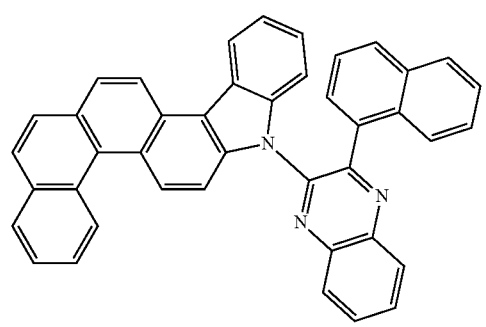

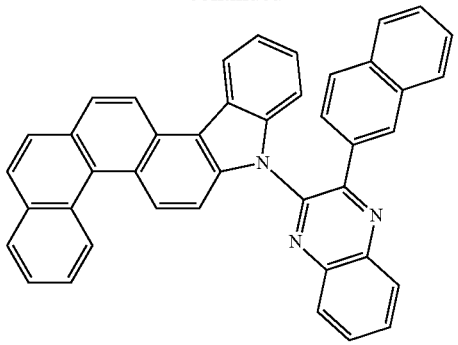

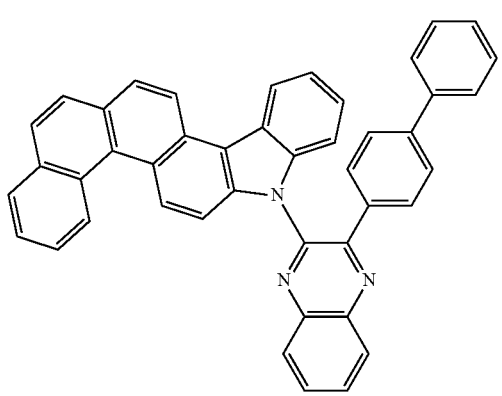

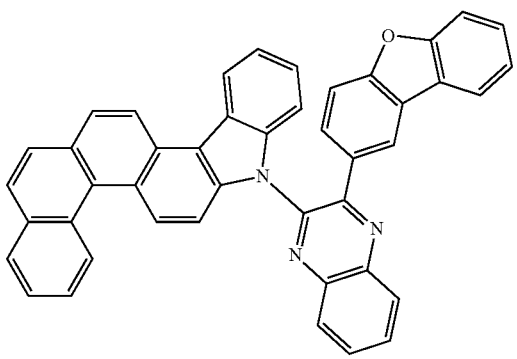

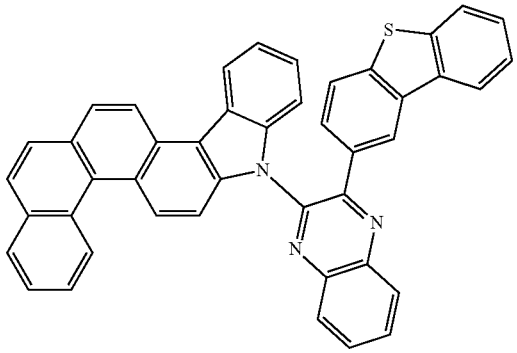

A compound of formula (XIV):

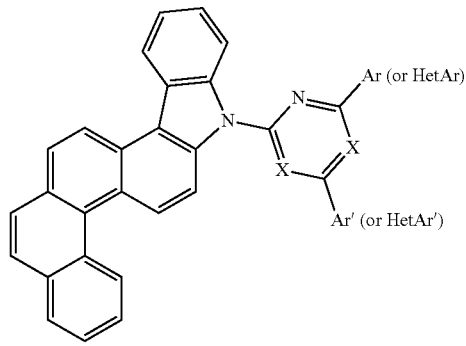

(XIV)

wherein

Ar and Ar' are each independently unsubstituted or substituted phenyl, unsubstituted or substituted biphenyl or unsubstituted or substituted naphthyl, preferably unsubstituted phenyl, unsubstituted biphenyl or unsubstituted naphthyl;

HetAr and HetAr' are each independently unsubstituted or substituted carbazolyl, unsubstituted or substituted dibenzofuranyl or unsubstituted or substituted dibenzothiophenyl, preferably unsubstituted carbazolyl, unsubstituted dibenzofuranyl or unsubstituted dibenzothiophenyl;

X is N or CH, preferably at least one X is N, more preferably both X are N.

Examples for preferred compounds of formula (XIV) are shown below:

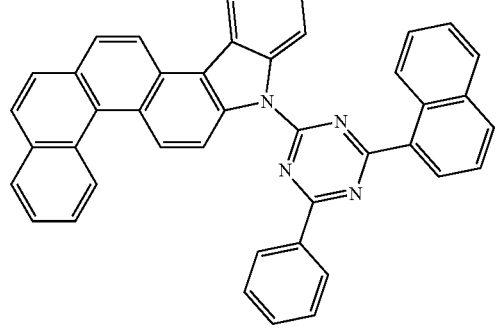

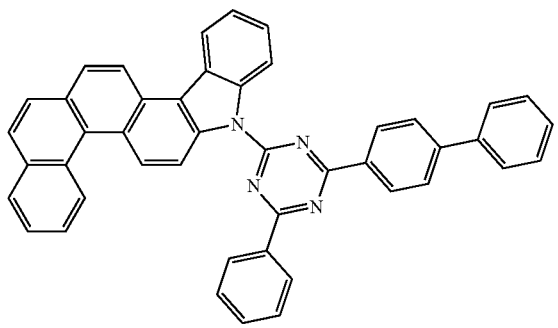

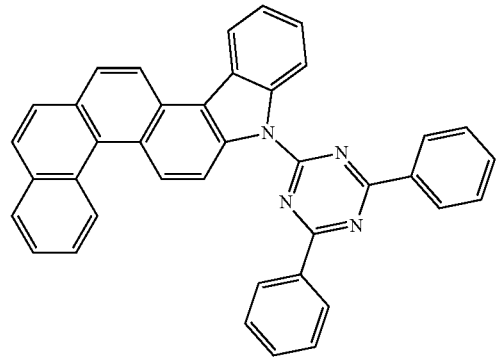

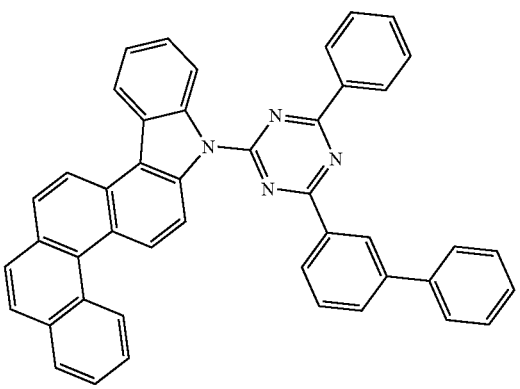

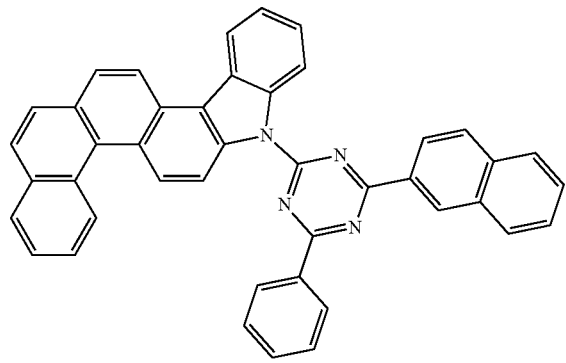

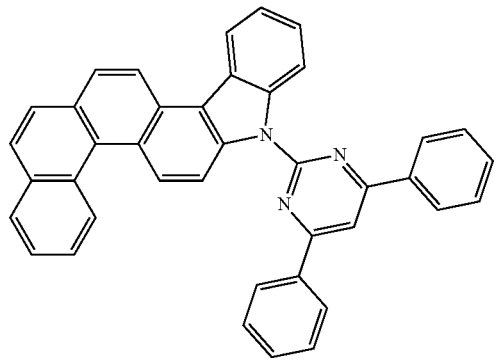

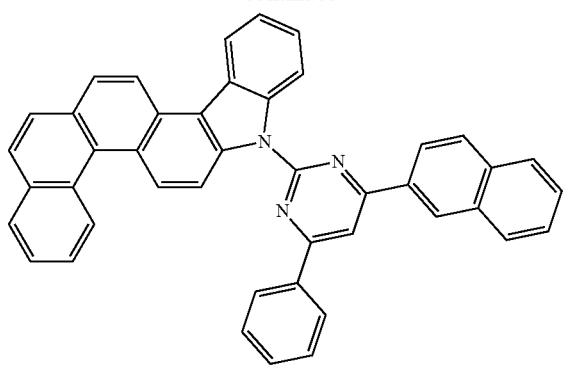
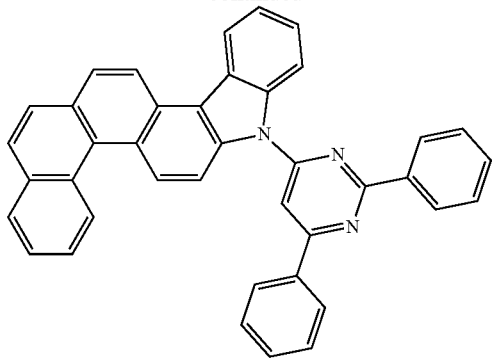
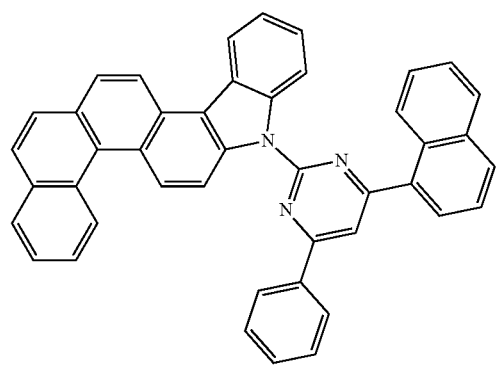
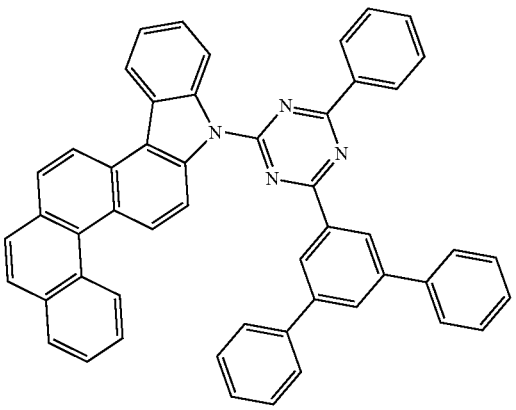
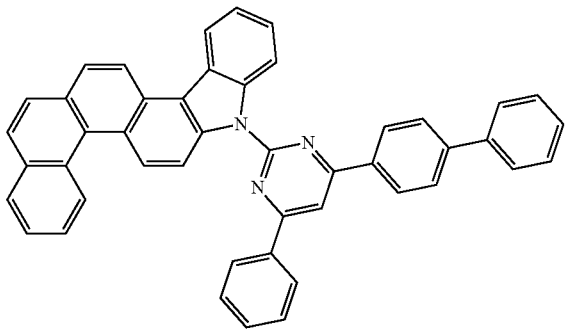
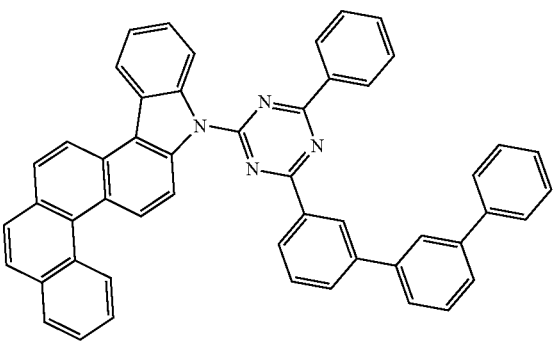
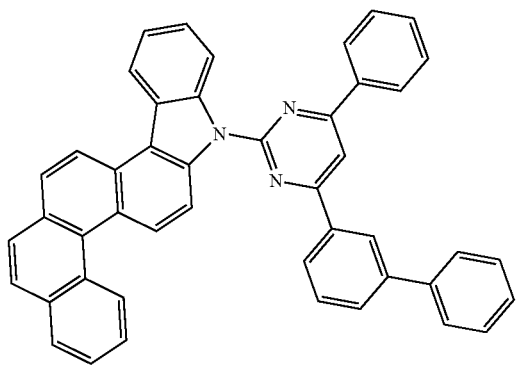
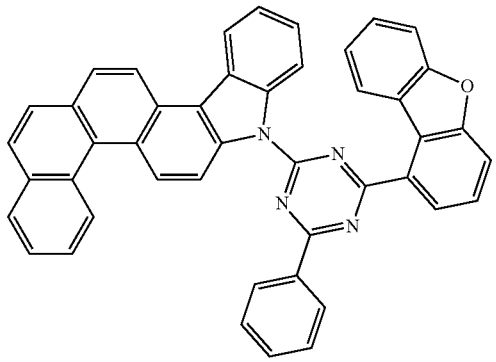

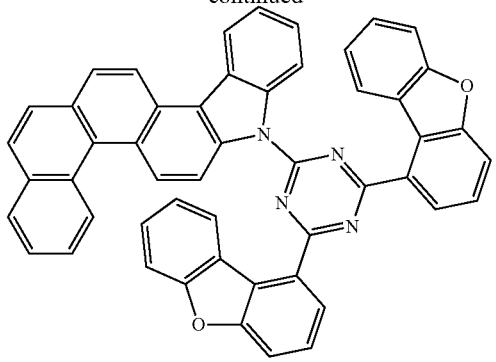
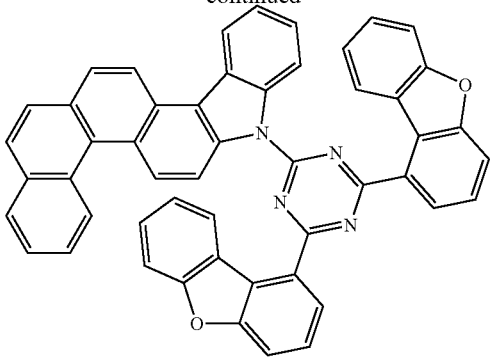

A compound of formula (XV):

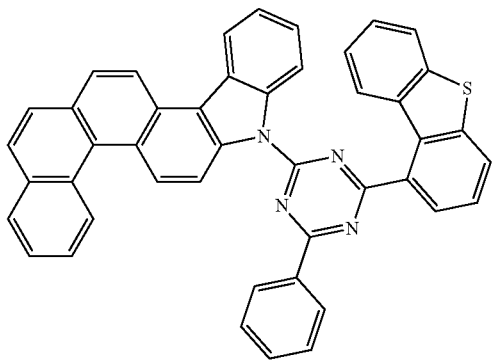

(XV)

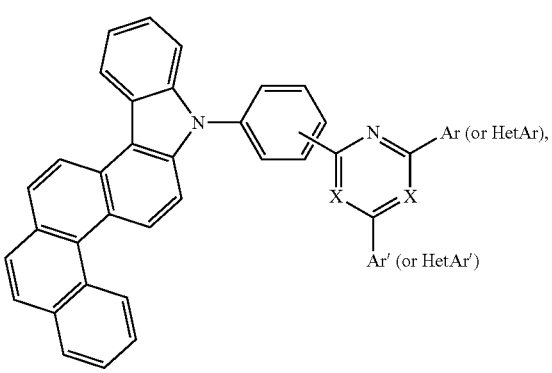

wherein

Ar and Ar' are each independently unsubstituted or substituted phenyl, unsubstituted or substituted biphenyl or unsubstituted or substituted naphthyl, preferably unsubstituted phenyl, unsubstituted biphenyl, a phenyl substituted biphenyl or unsubstituted naphthyl;

HetAr and HetAr' are each independently unsubstituted or substituted carbazolyl, unsubstituted or substituted dibenzofuranyl or unsubstituted or substituted dibenzothiophenyl, preferably unsubstituted carbazolyl, unsubstituted dibenzofuranyl or unsubstituted di benzothiophenyl, X is N or CH, preferably at least one X is N, more preferably both X are N.

Examples for preferred compounds of formula (XV) are shown below:

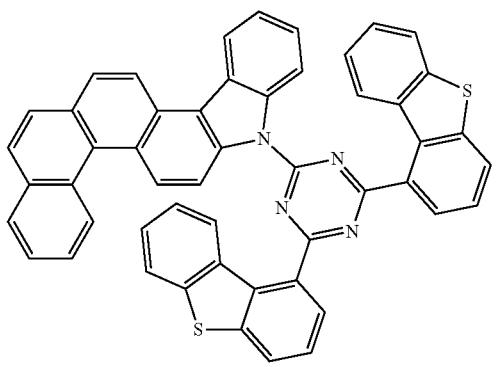
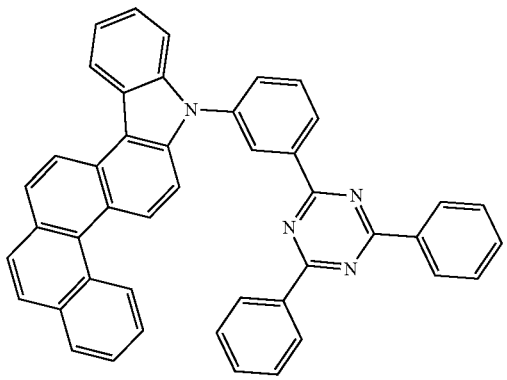

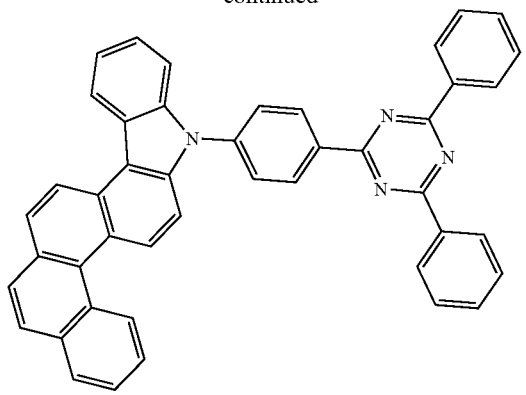
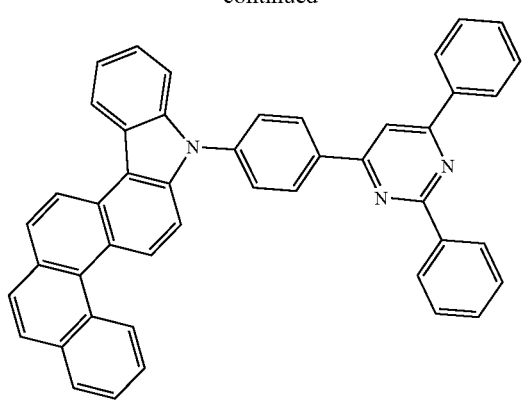
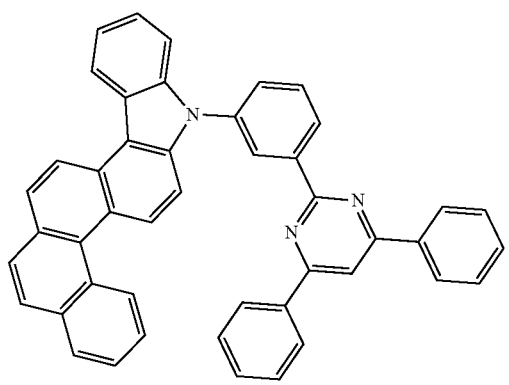
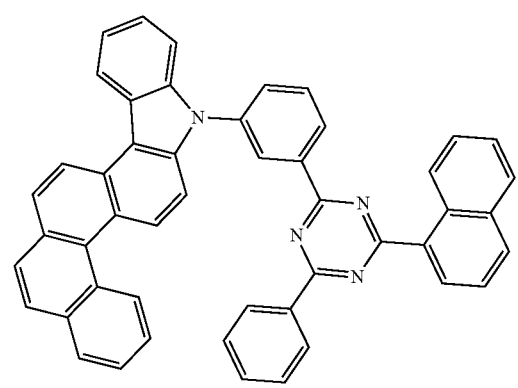
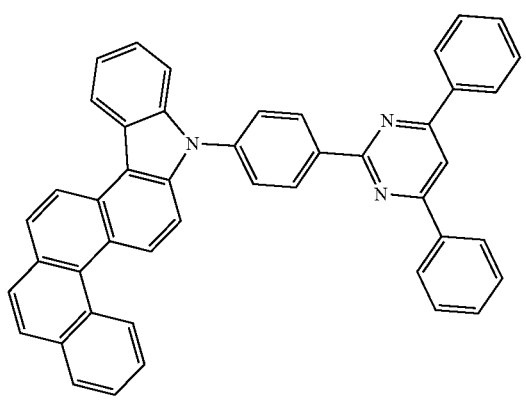
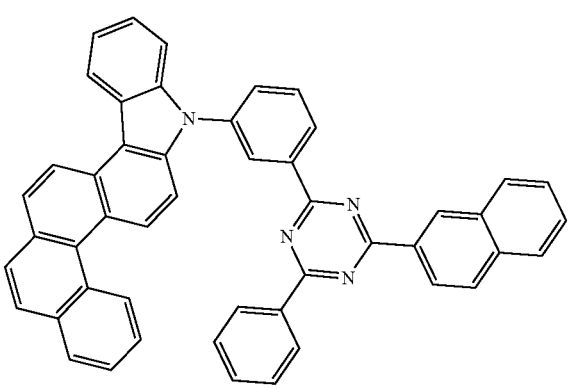
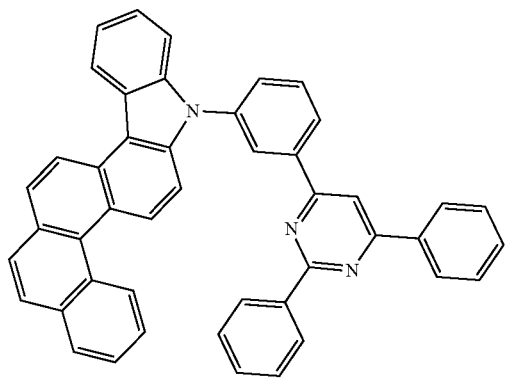
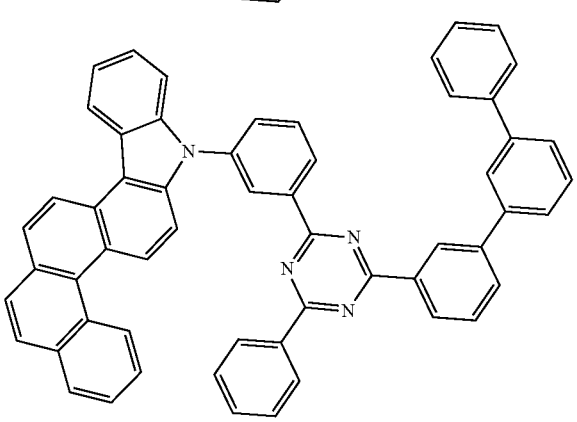

-continued

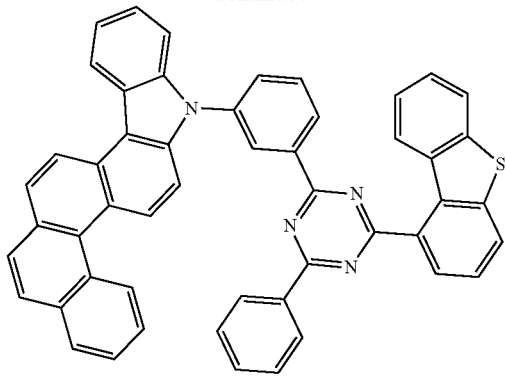

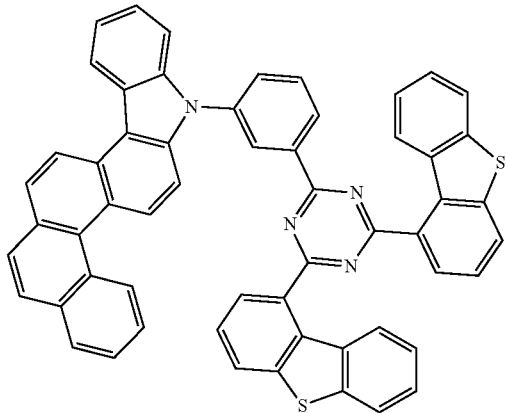

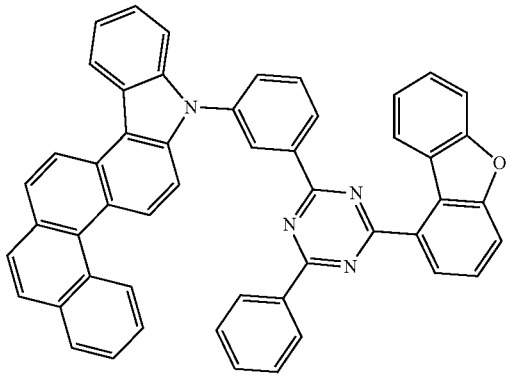

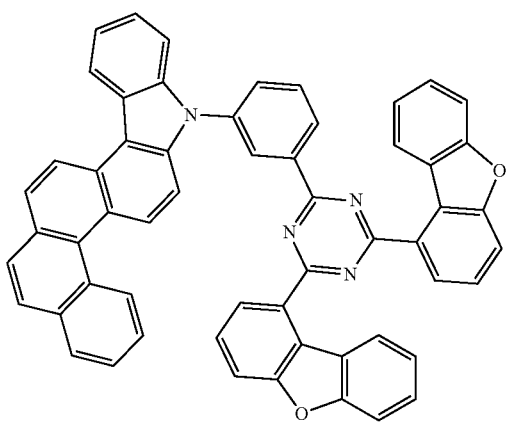 [SMILES: c1cc(-c2nc(-c3cccc4oc5ccccc5c34)nc(-c3cccc4oc5ccccc5c34)n2)cc(-n2c3ccccc3c3c4ccc5ccc6ccccc6c5c4ccc32)c1]

A compound of formula (XVI):

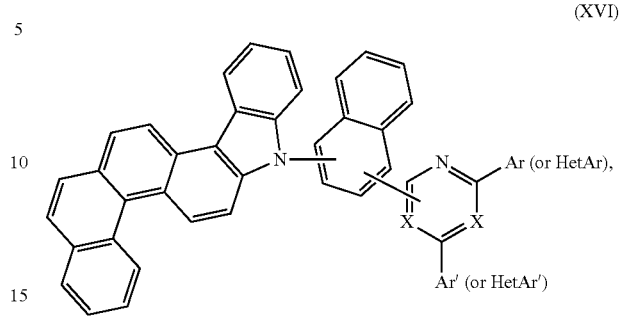

(XVI)

wherein

Ar and Ar' are each independently unsubstituted or substituted phenyl, unsubstituted or substituted biphenyl or unsubstituted or substituted naphthyl, preferably unsubstituted phenyl or a phenyl substituted biphenyl;

HetAr and HetAr' are each independently unsubstituted or substituted carbazolyl, unsubstituted or substituted dibenzofuranyl or unsubstituted or substituted dibenzothiophenyl, preferably unsubstituted dibenzofuranyl or unsubstituted dibenzothiophenyl;

X is N or CH, preferably at least one X is N, more preferably both X are N.

Examples for preferred compounds of formula (XVI) are shown below:

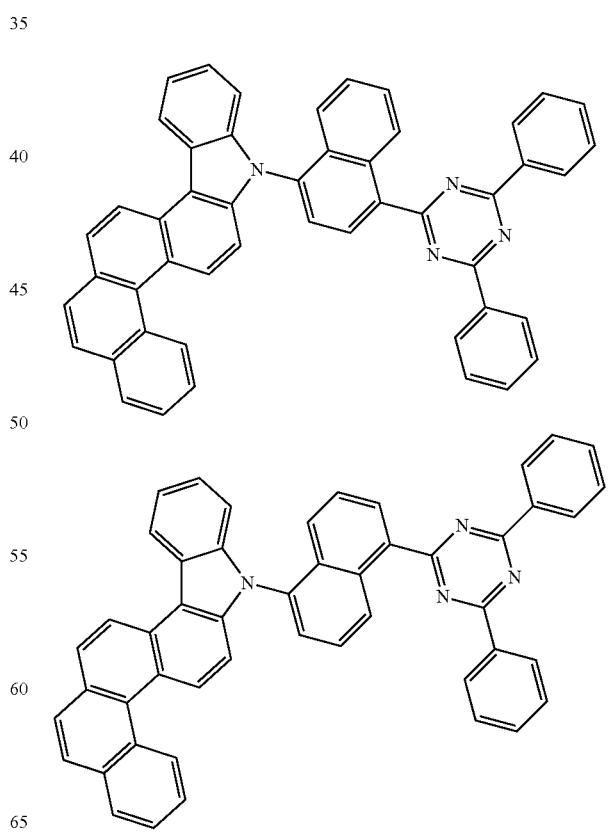

43
-continued
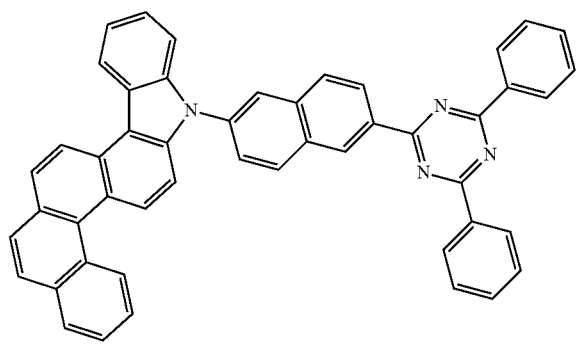
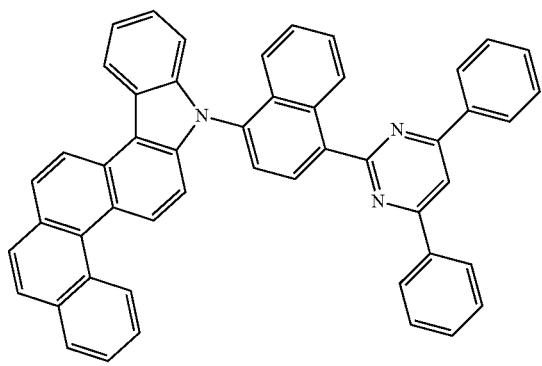
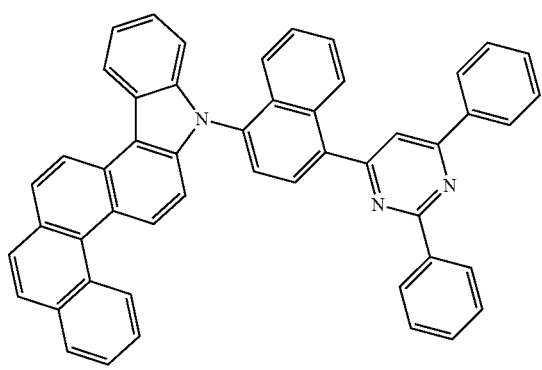
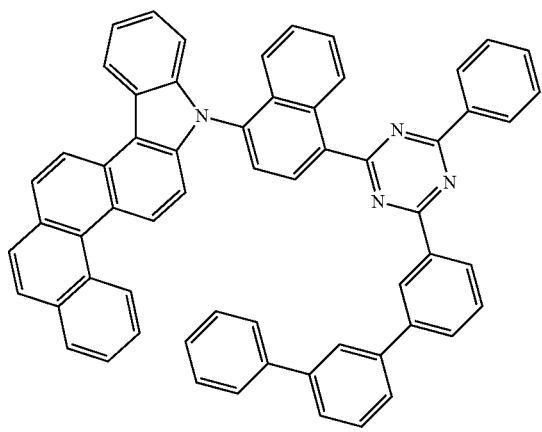
44
-continued
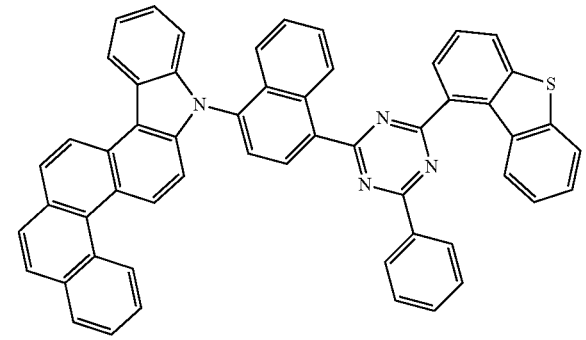
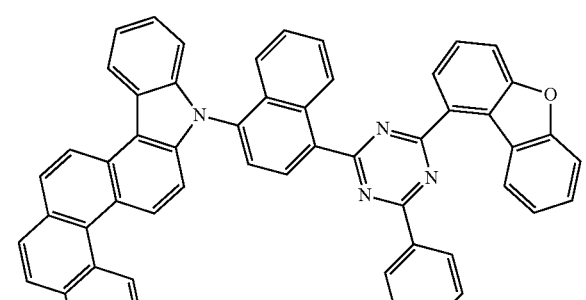
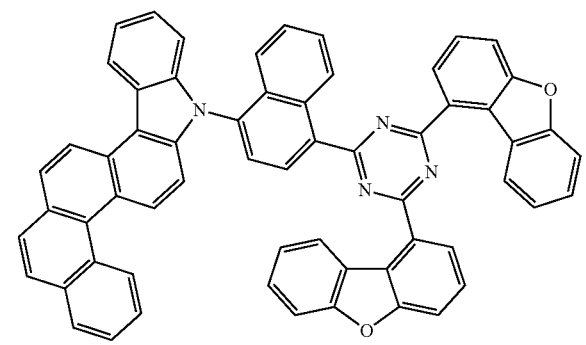

Compounds of formulae (XVII) and (XVIII):

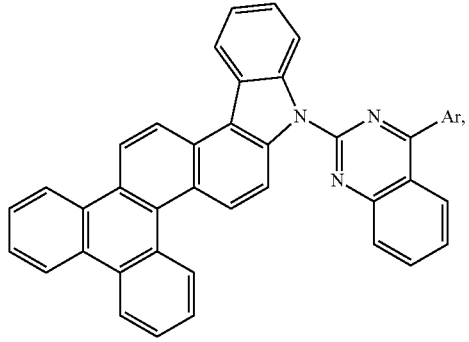
(XVII)

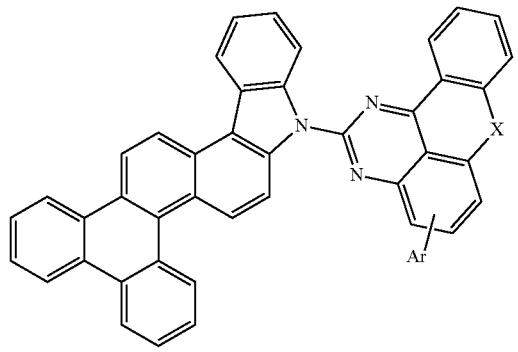
(XVIII)

wherein

Ar is unsubstituted or substituted phenyl, unsubstituted or substituted biphenyl or unsubstituted or substituted naphthyl, preferably unsubstituted phenyl;

X is O, N-phenyl, C(methyl)$_2$ or S, preferably O.

Examples for preferred compounds of formulae (XVII) and (XVIII) are shown below:

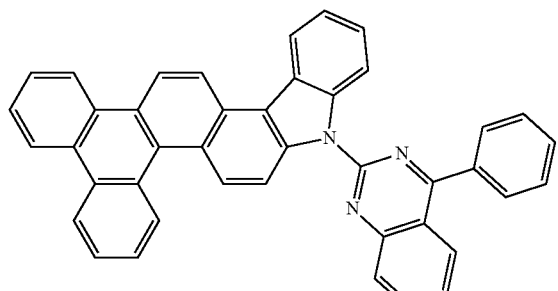

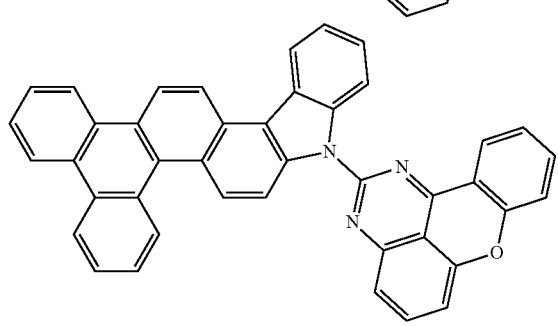

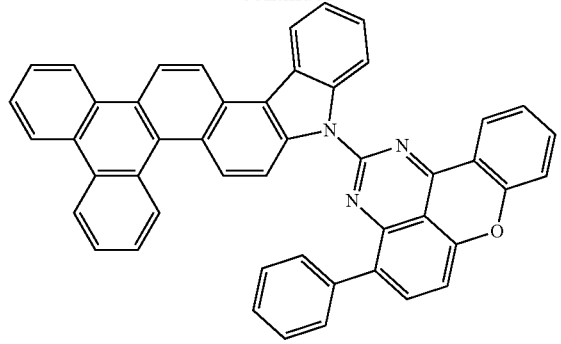

A compound of formula (XIX):

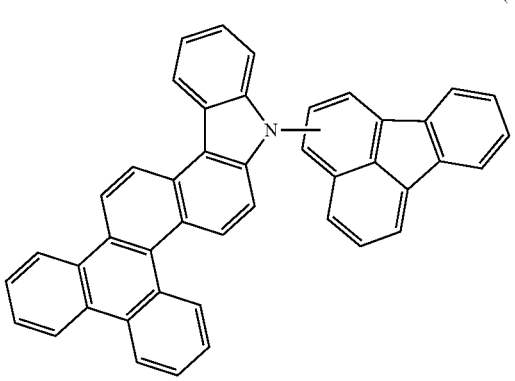
(XIX)

Examples for preferred compounds of formula (XIX) are shown below:

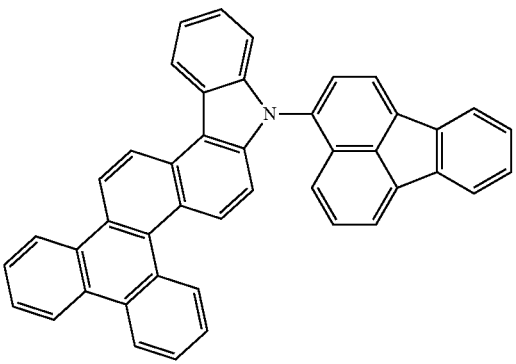

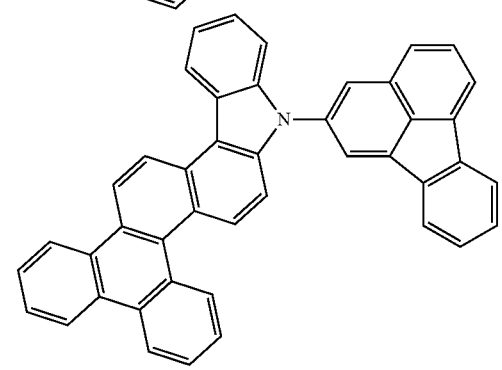

-continued

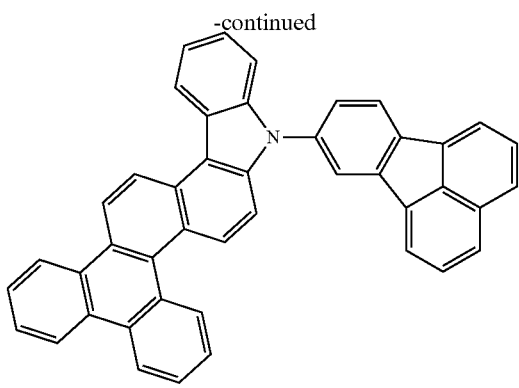

Preparation of the Compounds of Formula (I)

The present invention also relates to a process for the preparation of a compound according to general formula (I) as defined above, at least comprising step (A) or step (A*):

(A) Coupling a compound of formula (IIa)

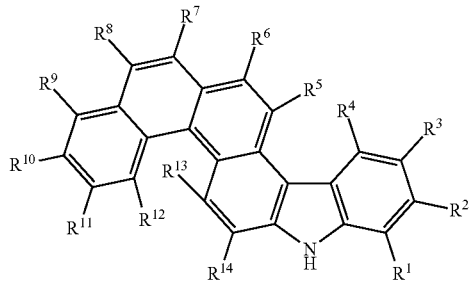

with a compound of formula

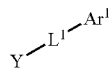

wherein

Y is a halide selected from the group consisting of I, F, Cl and Br, or a pseudohalide selected from the group consisting of mesylate, triflate, tosylate and nonaflate, or (A*) In the case that $L^1$ is not a single bond—coupling a compound of formula (IIb)

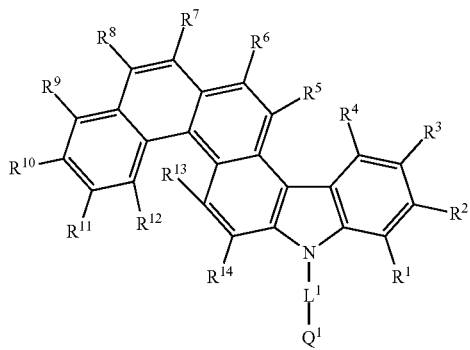

with a compound of formula (IIIb)

$$Q^2{-}Ar^1$$

wherein

One of $Q^1$ and $Q^2$ is a halide selected from the group consisting of I, F, Cl and Br, or a pseudohalide selected from the group consisting of mesylate, triflate, tosylate and nonaflate; and the other of $Q^1$ and $Q^2$ is $BZ_2$, and Z is $C_1$-$C_8$alkyl, OH, or O—$C_1$-$C_8$alkyl, wherein the two alkyl groups in the group $BZ_2$ may form together with the B and the two oxygen atoms a cyclic group which may be unsubstituted or substituted and/or fused, for example with an aryl group;

wherein the definitions of the groups and residues $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $L^1$ and $Ar^1$ are defined above.

Step (A) and step (A*) of the process according to the present invention can in general be conducted by any method and under any conditions that are known to provide the desired product by a person having ordinary skill in the art.

For example, the coupling reactions involving a N atom and a C atom, so called aminations reactions in step (A) of the process according to the present invention can be carried either catalyzed or not catalyzed. For example in the presence of copper in an Ullmann type coupling such as described in *Org. Lett.*, 2002, 4, 581-584 or *Org. Lett.*, 2002, 4, 581-584. The amination reaction in step (A) can for example also be carried out in the presence of palladium in so-called Buchwald-Hartwig coupling such as described in *Org. Lett.*, 2008, 10, 4109-4112, and *Org. Lett.*, 2003, 5, 2413-2415, or between amines and aryl halides by nucleophilic aromatic substitution such as described in *Synthesis*, 48(5), 737-750; 2016 or *Angewandte Chemie, International Edition*, 51(32), 8012-8016.

Step (A*) of the process according to the present invention can be coupling reactions that are known to a person having ordinary skill in the art, for example reactions using a halide and a boronic acid or ester and a palladium catalyst (Suzuki coupling as for example described in *Chem. Soc. Rev.*, 2014, 3525, *Angew. Chem. Int. Ed.*, 2009, 6954).

The present invention therefore preferably relates to the process according to the present invention, wherein step (A) is a coupling reaction that is conducted in the presence of a base and/or in the presence of a palladium and/or copper catalyst.

In particular the coupling according to step (A) and step (A*) of the process according to the present invention is conducted in the presence of at least one basic compound, for example selected from the group consisting of alkali metal salts of alcohols having 1 to 6 carbon atoms, in particular sodium tert-butoxide, potassium tert-butoxide, potassium carbonate, cesium carbonate, rubidium carbonate or potassium phosphate.

The reaction according to step (A) and step (A*) of the process according to the present invention is preferably conducted in at least one aprotic, organic solvent. Preferred are aromatic solvents, for example selected from the group consisting of toluene, benzene, xylene, mesitylene, dimethylformamide (DMF), dimethylacetamide (DMA), tetrahydrofuran (THF) and mixtures thereof.

As a catalyst in step (A)—if present—particularly preferably a combination of at least one Lewis acid and of at least one palladium compound is used. Particularly preferably, a combination of at least one boron comprising complex and at least one palladium salt is used, for example a combination of tert-Bu$_3$P—HBF$_4$ and Pd$_2$(dba)$_3$, wherein dba means dibenzylideneacetone. Other suitable ligands and/or palladium comprising reagents are mentioned in the above mentioned scientific papers.

As a catalyst in step (A)* a nickel or palladium catalyst is usually employed, preferably a palladium catalyst like Pd(PPh$_3$)$_4$, PdCl$_2$(PPh$_3$)$_2$, PdCl$_2$(dppf) (dppf=1,1'-bis(diphenylphosphino)-ferrocene), PdCl$_2$(PCy$_3$)$_2$, or Pd$_2$(dba)$_3$ (dba=dibenzylideneacetone).

The reaction is conducted at a temperature that is high enough to obtain the desired compound in high yield and high selectivity, for example at 50 to 180° C., preferably at 70 to 160° C., particularly preferably at 80 to 150° C.

The reaction according to step (A) and step (A*) of the process according to the present invention is conducted for a time that is long enough to obtain the desired compound in high yield and high selectivity, for example for 1 to 60 h, preferably for 2 to 50 h, particularly preferably for 3 to 40 h.

After the reaction according to step (A) and step (A*) of the process according to the present invention is completed, the reaction mixture can be worked up according to methods that are known to the skilled artisan, for example extraction, filtration, recrystallization, chromatography etc.

The reaction product can be analyzed, for example, by proton- or carbon-NMR, mass spectrometry etc.

The substrates that are used in step (A) and step (A*) of the process according to the present invention, i.e. compounds according to general formulae (IIa) and (IIb) and compounds according to general formulae (IIIa) or (IIIb) can be made by methods that are known to a person having ordinary skill in the art or are commercially available.

Suitable reaction sequences for obtaining the compounds of formula (I) according to the present invention as well as for obtaining the compounds of formulae (IIa) and (IIIa) are shown in the examples.

Compounds of Formula (I) in Organic Electronics Applications

It has been found that the compounds of the formula (I) are particularly suitable for use in applications in which charge carrier conductivity is required, especially for use in organic electronics applications, for example selected from switching elements such as organic transistors, e.g. organic FETs and organic TFTs, organic solar cells and organic light-emitting diodes (OLEDs). The term organic EL device is used interchangeably with the term organic light-emitting diode (OLED) in the following; i.e. both terms have the same meaning in the sense of the present application.

The organic transistor generally includes a semiconductor layer formed from an organic layer with charge transport capacity; a gate electrode formed from a conductive layer; and an insulating layer introduced between the semiconductor layer and the conductive layer. A source electrode and a drain electrode are mounted on this arrangement in order thus to produce the transistor element. In addition, further layers known to those skilled in the art may be present in the organic transistor. The layers with charge transport capacity may comprise the compounds of formula (I).

The organic solar cell (photoelectric conversion element) generally comprises an organic layer present between two plate-type electrodes arranged in parallel. The organic layer may be configured on a comb-type electrode. There is no particular restriction regarding the site of the organic layer and there is no particular restriction regarding the material of the electrodes. When, however, plate-type electrodes arranged in parallel are used, at least one electrode is preferably formed from a transparent electrode, for example an ITO electrode or a fluorine-doped tin oxide electrode. The organic layer is formed from two sublayers, i.e. a layer with p-type semiconductor properties or hole transport capacity, and a layer formed with n-type semiconductor properties or charge transport capacity. In addition, it is possible for further layers known to those skilled in the art to be present in the organic solar cell. The layers with charge transport capacity may comprise the compounds of formula (I).

The compounds of formula (I) being particularly suitable in OLEDs for use as matrix material in a light-emitting layer and/or as charge and/or exciton blocker material, i.e. as electron/exciton blocker material or as hole/exciton blocker material, and/or charge transport material, i.e. hole transport material or electron transport material, especially in combination with a phosphorescence emitter.

In the case of use of the inventive compounds of formula (I) in OLEDs, OLEDs which have good efficiencies and a long lifetime and which can be operated especially at a low use and operating voltage are obtained. The inventive compounds of formula (I) are suitable especially for use as matrix and/or charge transport, i.e. hole or electron transport, and/or charge blocker material, i.e. hole or electron blocker material. Furthermore, the compounds of the formula (I) can be used as conductor/complementary materials in organic electronics applications selected from switching elements and organic solar cells. (In the sense of the present application, the terms matrix and host are used interchangeably).

The present invention therefore relates to an electronic device, preferably an organic electroluminescent device, more preferably an organic light emitting diode (OLED), comprising at least one compound of formula (I) according to the present invention.

The present invention preferably further relates to the electronic device according to the present invention, preferably an organic electroluminescence device, more preferably an organic light emitting diode (OLED), comprising a cathode, an anode, and a plurality of organic thin film layers provided between the cathode and the anode, the plurality of organic thin film layers comprising at least one compound of formula (I) according to the present invention.

The present invention preferably further relates to the electronic device according to the present invention, preferably an organic electroluminescence device, more preferably an organic light emitting diode (OLED), comprising a cathode, an anode, and a plurality of organic thin film layers provided between the cathode and the anode, the plurality of organic thin film layers comprising at least one emitting layer comprising at least one compound of formula (I) according to the present invention.

The present invention further relates to an electronic equipment comprising the organic electroluminescence device according to the present invention.

The present invention also relates to an emitting layer, preferably present in an electronic device, more preferably in an electroluminescence device, particularly preferably in an organic light emitting diode (OLED), comprising at least one compound of formula (I) according to the present invention.

The present invention preferably further relates to the use of at least one compound of formula (I) according to the present invention in an electronic device, preferably in an electroluminescence device, particularly preferably in an organic light emitting diode (OLED), preferably in an emitting layer.

According to the present application, the terms matrix and host are used interchangeably.

Suitable structures of organic electronic devices, especially organic light-emitting diodes (OLEDs), are known to those skilled in the art and are specified below.

Preferably, the present invention provides an organic light-emitting diode (OLED) comprising an anode and a cathode and a light-emitting layer arranged between the anode and the cathode, and if appropriate at least one further layer selected from the group consisting of at least one blocking layer for holes/excitons, at least one blocking layer for electrons/excitons, at least one hole injection layer, at least one hole transport layer, at least one electron injection layer and at least one electron transport layer, wherein the OLED comprises at least one compound of formula (I) according to the present invention.

The present application further relates to a light-emitting layer, preferably present in an electronic device, more preferably in an electroluminescence device, particularly preferably in an organic light emitting diode (OLED), comprising at least one compound of formula (I) according to the present invention. Examples of preferred compounds according to general formula (I) are shown above.

Organic EL Device (OLED)

The organic EL device as one embodiment of the invention comprises one or more organic thin film layers including an emitting layer between a cathode and an anode, and at least one layer of the organic thin film layers comprises the compound of formula (I).

As examples of the organic thin film layers that comprise the compound of formula (I), an anode-side organic thin film layer (hole-transporting layer, hole-injecting layer, or the like), an emitting layer, a cathode-side organic thin film layer (electron-transporting layer, electron-injecting layer, or the like) provided between a cathode and an emitting layer, a spacing layer, a barrier layer or the like can be given. The examples are not limited thereto.

The compound of formula (I) may be contained in any of the abovementioned layers, and can be used as a host material or a dopant material in the emitting layer of a fluorescent emitting unit, a host material in the emitting layer of a phosphorescent emitting unit, a hole-transporting layer, an electron-transporting layer or the like of an emitting unit.

Preferably, the compounds of the formula (I) are used as matrix materials (host materials), preferably in an emission layer of an OLED, more preferably in an emission layer of an OLED comprising at least one compound of the formula (I) and at least one emitter material, wherein the emitter material is preferably a fluorescent or phosphorescent emitter material, more preferably a red fluorescent or phosphorescent emitter material.

The organic EL device of the invention may be a fluorescent or phosphorescent monochromatic emitting device or may be a fluorescent/phosphorescent hybrid white emitting device. It may be a simple emitting device having a single emitting unit or a tandem emitting device having plural emitting units. Among them, the organic EL device may preferably be a phosphorescent emitting device.

As the representative device structure of a simple type organic EL device, the following device configuration can be given.

(1) Anode/Emitting Unit/Cathode

The emitting unit mentioned above may be a stacked type emitting unit comprising plural phosphorescent emitting layers or plural fluorescent emitting layers. In this case, in order to prevent diffusion of excitons generated in the phosphorescent emitting layer to the fluorescent emitting layer, a spacing layer may be provided between the emitting layers. The representative layer configuration of the emitting unit is given below.

(a) Hole-transporting layer/Emitting layer (/Electron-transporting layer)
(b) Hole-transporting layer/First phosphorescent emitting layer/Second phosphorescent emitting layer (/Electron-transporting layer)
(c) Hole-transporting layer/Phosphorescent emitting layer/Spacing layer/Fluorescent emitting layer (/Electron-transporting layer)
(d) Hole-transporting layer/First phosphorescent emitting layer/Second phosphorescent emitting layer/Spacing layer/Fluorescent emitting layer (/Electron-transporting layer)
(e) Hole-transporting layer/First phosphorescent emitting layer/Spacing layer/Second phosphorescent emitting layer/Spacing layer/Fluorescent emitting layer (/Electron-transporting layer)
(f) Hole-transporting layer/Phosphorescent emitting layer/Spacing layer/First fluorescent emitting layer/Second fluorescent emitting layer (/Electron-transporting layer)
(g) Hole-transporting layer/Electron barrier layer/Emitting layer (/Electron-transporting layer)
(h) Hole-transporting layer/Emitting layer/Hole barrier layer (/Electron-transporting layer)
(i) Hole-transporting layer/Fluorescent emitting layer/Triplet barrier layer (/Electron-transporting layer)

The phosphorescent or fluorescent emitting layer as mentioned above can emit different colors of light. Specifically, in the stacked emitting layer (d), a layer configuration of the hole transporting layer/first phosphorescent emitting layer (red emission)/second phosphorescent emitting layer (green emission)/spacing layer/fluorescent emitting layer (blue emission)/electron transporting layer or the like can be given.

Between each emitting layer and the hole-transporting layer or the spacing layer, an electron barrier layer may be provided appropriately. Between each emitting layer and the electron transporting layer, a hole-barrier layer may be provided appropriately. Due to provision of an electron-barrier layer or a hole-barrier layer, electrons or holes can be confined within the emitting layer, whereby possibility of recombination of carriers in the emitting layer can be increased, and the life can be improved.

As the represented device configuration of a tandem organic EL device, the following device configuration can be given.

(2) Anode/First Emitting Unit/Intermediate Layer/Second Emitting Unit/Cathode

Here, as the first emitting unit and the second emitting unit, the same emitting units as those mentioned above can independently be given, for example.

In general, the intermediate layer is called an intermediate electrode, an intermediate conductive layer, a carrier-generating layer, an electron-withdrawing layer, and a known material configuration that supplies electrons to the first emitting unit and supplies holes to the second emitting unit can be used.

FIG. 1 shows a schematic configuration of one example of the organic EL device of the invention. The organic EL device 1 comprises a substrate 2, an anode 3, a cathode 4 and an emitting unit 10 provided between the anode 3 and the cathode 4. The emitting unit 10 comprises an emitting layer 5 preferably comprising a host material and a dopant. A hole injecting and transporting layer 6 or the like may be provided between the emitting layer 5 and the anode 3 and an electron-injecting layer 8 and an electron transporting layer 7 or the like (electron injecting and transporting unit 11) may be provided between the emitting layer 5 and the cathode 4. An electron-barrier layer may be provided on the anode 3 side of the emitting layer 5 and a hole-barrier layer may be provided on the cathode 4 side of the emitting layer 5.

Due to such configuration, electrons or holes can be confined in the emitting layer 5, whereby possibility of generation of excitons in the emitting layer 5 can be improved.

Herein, a host that is combined with a fluorescent dopant is referred to as a fluorescent host and a host that is combined with a phosphorescent dopant is referred to as a phosphorescent host. The fluorescent host and the phosphorescent host are not distinguished only by the molecular structure thereof. That is, the phosphorescent host means a material constituting a phosphorescent emitting layer that contains a phosphorescent dopant and does not mean a material that cannot be used as a material constituting a fluorescent dopant. The same can be applied to a fluorescent host.

Substrate

The organic EL device is usually formed on a transparent substrate. The transparent substrate is a substrate for supporting the organic EL device, and is preferably a flat and smooth substrate having a 400-to-700-nm-visible-light transmittance of 50% or more. Specific examples thereof include glass plates and polymer plates. Examples of the glass plate include those obtained by using as raw materials soda-lime glass, barium/strontium-containing glass, lead glass, aluminosilicate glass, borosilicate glass, barium borosilicate glass, quartz, or the like. Examples of the polymer plate include those obtained by using as raw materials polycarbonate, acrylic polymer, polyethylene terephthalate, polyethersulfide, polysulfone, or the like.

Anode

The anode of the organic EL device plays a role for injecting holes into its hole-transporting layer or emitting layer. It is effective to use one having a work function of 4.5 eV or more. As specific examples of the anode material, indium tin oxide alloy (ITO), tin oxide (NESA), indium zinc oxide, gold, silver, platinum, copper, and the like can be given. The anode can be formed by forming these electrode materials into a thin film by vapor deposition, sputtering or the like. In the case where emission from the emitting layer is taken out through the anode, the transmittance of the anode to the emission is preferably more than 10%. The sheet resistance of the anode is preferably several hundred Ω/□ or less. The film thickness of the anode, which varies depending upon the material thereof, is usually from 10 nm to 1 μm, preferably from 10 to 200 nm.

Cathode

The cathode plays a role for injecting electrons into its electron-injecting layer, electron-transporting layer or emitting layer. The cathode is preferably formed of a material having a small work function. The cathode material is not particularly restricted. As specific examples of the cathode material, indium, aluminum, magnesium, a magnesium-indium alloy, a magnesium-aluminum alloy, an aluminum-lithium alloy, an aluminum-scandium-lithium alloy, a magnesium-silver alloy or the like can be given. As in the case of the anode, the cathode can be formed by forming the materials into a thin film by a deposition method, a sputtering method or the like. If necessary, emission can be outcoupled from the cathode side.

Emitting Layer

The emitting layer is an organic layer having an emitting function, and where a doping system is used, it comprises a host material and a dopant material. The host material has a function of accelerating recombination of electrons and holes and confining excitons within the emitting layer. The dopant material has a function of emitting efficiently excitons obtained by recombination.

In the case of a phosphorescent device, the host material has a function of confining excitons mainly generated by a dopant within the emitting layer.

Here, in the emitting layer, a double host (also referred to as a host/cohost) that adjusts the carrier balance in the emitting layer may be used by combining an electron-transporting host and a hole-transporting host or by other methods. It is preferred that the emitting layer comprise a first host material and a second host material and that at least one component of the first host material and the second host material is the compounds of the formula (I) according to the invention. Double dopant may be used in which two or more types of dopant materials having a high quantum yield are incorporated, and each dopant emits light. Specifically, by allowing a host, a red dopant and a green dopant to be co-deposited, yellow emission from the common emitting layer, whereby yellow emission is realized.

As for the emitting layer, by allowing plural emitting layers to be a stacked body, electrons and holes are accumulated in the interface of the emitting layers, whereby the recombination region is concentrated in the interface of the emitting layers. As a result, the quantum efficiency is improved.

Easiness in injection of holes to the emitting layer and easiness in injection of electrons to the emitting layer may differ. Further, the hole-transporting performance and the electron transporting performance indicated by the mobility of holes and electrons in the emitting layer may differ from each other.

The emitting layer can be formed by a known method such as a deposition method, a spin coating method, a LB method (Langmuir Blodgett method) or the like, for example. The emitting layer can also be formed by forming a solution obtained by dissolving a binder such as a resin and material compounds in a solvent into a thin film by a spin coating method and the like.

The emitting layer is preferably a molecular deposited film. The "molecular deposited film" means a thin film formed by deposition of a raw material compound in a vapor phase or a film formed by solidification of a raw material compound in a solution state or a liquid phase state. Normally, this molecular deposited film differs from a thin film (molecular accumulated film) formed by a LB method in aggregation structure or high-order structure, or differ in function derived from such difference in structure.

In a more preferred embodiment, the light-emitting layer is formed from 0.1 to 70% by weight, preferably 1 to 30% by weight, of at least one of the aforementioned emitter materials and 30 to 99.9% by weight, preferably 70 to 99% by weight, of at least one of the matrix materials mentioned in the specification—in one embodiment at least one compound of the formula (I) where the sum total of the emitter material and of the matrix material adds up to 100% by weight.

(1) Phosphorescent Emitting Layer

The phosphorescent emitting layer usually comprises at least one emitter material and at least one host material. The phosphorescent host is a compound which confines the triplet energy of the phosphorescent dopant efficiently in the light emitting layer to cause the phosphorescent dopant to emit light efficiently.

A host material for phosphorescent emitting layer is usually selected from known phosphorescent host materials. Specific examples of the preferable phosphorescent host are, nitrogen containing heteroaromatics, such as, indole derivatives, carbazole derivatives, pyridine derivatives, pyrimidine derivatives, triazine derivatives, quinoline derivatives, isoquinoline derivatives, quinazoline derivatives, nitrogenated-dibenzothiophene derivatives, nitrogenated-dibenzofuran derivatives, imidazole derivatives, such as benzimidazole derivatives, imidazopyridine derivatives, benzimidazophenanthridine derivatives, benzimidzobenzimidazole derivatives; oxygen or sulfur containing heteroaromatics, such as thiophene derivatives, furan derivatives, benzothiophene derivatives, benzofuran derivatives, dibenzothiophene derivatives, dibenzofuran derivatives; aryl or heteroaryl substituted amine derivatives; metal complexes; aromatic hydrocarbon derivatives, such as benzene derivatives naphthalene derivatives, phenanthrene derivatives, triphenylene derivatives, fluorene derivatives, and so on, preferably, nitrogen containing heteroaromatics, the most preferably, the compounds of the formula (I).

According to one embodiment, the light-emitting layer comprises at least one emitter material and at least two matrix materials, wherein one of the matrix materials is a compound of the formula (I) and the other matrix material(s) is/are used as co-host(s). Suitable other host materials than the compounds of formula (I) (co-hosts) are mentioned below.

However, it is also possible to use two or more different compounds of formula (I) as host material in the light-emitting layer in an OLED of the present application.

Said second host material is selected from general phosphorescent host materials. Specific examples are selected from above mentioned derivatives, preferably, nitrogen containing heteroaromatics, more preferably, following general formula (N-1).

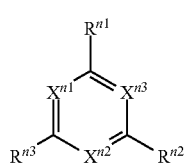

(N-1)

$X^{n1}$ to $X^{n3}$ each independently represents $CR^{n4}$ or N, $R^{n1}$ to $R^{n4}$ each independently represents hydrogen, halogen atom, a substituted or unsubstituted alkyl group having 1 to 25 carbon atoms, a substituted or unsubstituted alkenyl group having 2 to 25 carbon atoms, a substituted or unsubstituted alkynyl group having 2 to 25 carbon atoms, a substituted or unsubstituted cycloalkyl group having 3 to 25 carbon atoms, a substituted or unsubstituted alkoxy group having 1 to 25 carbon atoms, a substituted or unsubstituted aryl group having 6 to 24 carbon atoms, a substituted or unsubstituted heterocyclic group having 5 to 30 cyclic atoms, a substituted or unsubstituted aryloxy group having 6 to 24 carbon atoms, a substituted or unsubstituted alkylthio group having 1 to 25 carbon atoms, a substituted or unsubstituted arylthio group having 6 to 24 carbon atoms, alkyl or aryl substituted silyl group, alkyl or aryl substituted carbonyl group, or a substituted phosphoryl group, in the case of at least one of $X^{n1}$ to $X^{n3}$ represent $CR^{n4}$, two or more substituents selected among $R^{n1} \sim R^{n4}$ may be bonded to each other to form a ring structure.

In one further embodiment of the present invention, preferred heteroaromatics for the second host are specific nitrogen containing heteroaromatics with electron donating nitrogen atom(s), such as pyrrole compounds, indole compounds, carbazole compounds, acridine compounds, phenoxadrine compounds, phenothiazine compounds, imidazole compounds, benzimidazole compounds, and benzimidazobenzimidazole compounds, which may have additional substituents and additional fused ring structures, preferably carbazole compounds, more preferably following general formula (P-1).

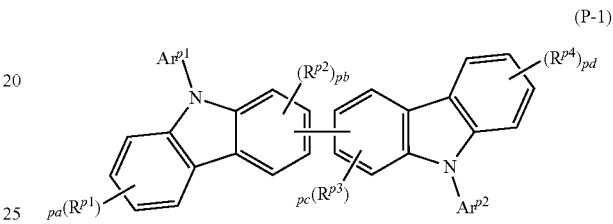

(P-1)

$Ar^{p1}$ and $Ar^{p2}$ each independently represents a substituted or unsubstituted aryl group having 6 to 24 carbon atoms, preferably, phenyl group, biphenyl group, terphenyl group, quarterphenyl group, naphthyl group, phenanthryl group or triphenylenyl group, or a substituted or unsubstituted heterocyclic group having 5 to 30 cyclic atoms, preferably, carbazoryl group, dibenzofuranyl group or dibenzothiophenyl group, or a substituent which consists of substituted or un substituted aryl group and substituted or unsubstituted heteroaryl group, preferably, aryl group and dibenzofuran group, aryl group and dibenzothiophene group or aryl group and carbazole group. $R^{p1}$ to $R^{p4}$ each independently represents halogen atom, a substituted or unsubstituted alkyl group having 1 to 25 carbon atoms, a substituted or unsubstituted alkenyl group having 2 to 25 carbon atoms, a substituted or unsubstituted alkynyl group having 2 to 25 carbon atoms, a substituted or unsubstituted cycloalkyl group having 3 to 25 carbon atoms, a substituted or unsubstituted alkoxy group having 1 to 25 carbon atoms, a substituted or unsubstituted aryl group having 6 to 24 carbon atoms, a substituted or unsubstituted heterocyclic group having 5 to 30 cyclic atoms, a substituted or unsubstituted aryloxy group having 6 to 24 carbon atoms, a substituted or unsubstituted alkylthio group having 1 to 25 carbon atoms, a substituted or unsubstituted arylthio group having 6 to 24 carbon atoms, alkyl or aryl substituted silyl group, alkyl or aryl substituted carbonyl group, a substituted phosphoryl group or a cyano group, or $R^{50}$ and $R^{51}$ may be bonded to each other to form a substituted or unsubstituted aryl group having 6 to 24 carbon atoms.

pa and pd each independently represents 0 to 4.

pb and pc each independently represents 0 to 3.

In one further embodiment of the present invention, aryl or heteroaryl substituted amine compounds can be preferably used for the second host material. Latter mentioned materials for hole transporting layer can be preferably used as a second host material.

In one further embodiment of the present invention, fused aryl compounds or fused heteroaryl compounds are preferably for the second host material.

In the case that the light-emitting layer comprises at least one emitter material and at least two matrix materials, wherein one of the matrix materials is preferably a compound of the formula (I) and the other matrix material(s) is/are used as co-host(s), whereby suitable host materials other than the compounds of formula (I) (co-hosts) are mentioned above, the light-emitting layer is formed from 0.1 to 70% by weight, preferably 1 to 30% by weight, of the at least one emitter material and 30 to 99.9% by weight, preferably 70 to 99% by weight, of a first host and the further matrix material, where the sum total of the at least one emitter material, the further matrix materials adds up to 100% by weight.

The content ratio of the compound of the first host material and the second matrix material as co-host in the light emitting layer is not particularly limited and may be selected accordingly, and the ratio of first host material: second host material is preferably 1:99 to 99:1, more preferably 10:90 to 90:10, each based on mass.

A phosphorescent dopant (phosphorescent emitting material) that forms the emitting layer is a compound that can emit light from triplet excited state. The phosphorescent dopant is not limited as long as it can emit from triplet excited state. The phosphorescent dopant is preferably an organic metal complex containing at least one metal selected from Ir, Pt, Os, Au, Cu, Re and Ru and a ligand. It is preferred that the ligand have an ortho-metalated bond. In respect of a high phosphorescent quantum yield and capability of improving external quantum yield of an emitting device, the phosphorescent dopant is preferably a compound having a metal atom selected from Ir, Os and Pt. Further preferable are a metal complex such as an iridium complex, an osmium complex and a platinum complex, with an ortho-metalated complex being more preferable. Among them, an iridium complex and a platinum complex are more preferable, and an ortho-metalated iridium complex is particularly preferable.

The phosphorescent host is a compound having a function of allowing a phosphorescent dopant to emit light efficiently by efficiently confining the triplet energy of the phosphorescent dopant in the emitting layer. The material for an organic EL device according to the invention is preferable as the phosphorescent host. The emitting layer may comprise one kind of the material for an organic EL device according to the invention or may comprise two or more kinds of the material for an organic EL device according to the invention.

When the material for an organic EL device according to the invention is used as a host material of the emitting layer, the emission wavelength of the phosphorescent dopant contained in the emitting layer is not particularly restricted. It is preferred that at least one kind of the phosphorescent dopant materials contained in the emitting layer have a peak of an emission wavelength of 490 nm or more and 700 nm or less, more preferably 490 nm or more and 650 nm or less. As for the emission color of the emitting layer, red, yellow and green are preferable, for example. By using the compound according to the invention as the host material and by forming an emitting layer by doping the phosphorescent dopant having such an emission wavelength, it is possible to obtain a long-lived organic EL device.

In the organic EL device according to the invention, other compounds than the material for an organic EL device according to the invention can appropriately be selected as the phosphorescent host according to the above-mentioned purpose.

The material for an organic EL device according to the invention and other compounds may be used in combination as the phosphorescent host material in the same emitting layer. When plural emitting layers are present, as the phosphorescent host material for one of these emitting layers, the material for an organic EL device according to the invention is used, and as the phosphorescent host material for one of other emitting layers, other compounds than the material for an organic EL device according to the invention may be used. The material for an organic EL device according to the invention can be used in an organic layer other than the emitting layer. In that case, as the phosphorescent host of the emitting layer, other compounds than the material for an organic EL device according to the invention may be used.

The content of the emitter materials (dopants), preferably the phosphorescent emitter materials, in the light emitting layer is not particularly limited and selected according to the use of the device, and preferably 0.1 to 70% by mass, and more preferably 1 to 30% by mass. If being 0.1% by mass or more, the amount of light emission is sufficient. If being 70% by mass or less, the concentration quenching can be avoided. The further component in the emitting layer is usually one or more host material, which is preferably present in an amount of 30 to 99.9% by mass, more preferably 70 to 99% by mass, wherein the sum of the emitter material(s) and the host material(s) is 100% by mass.

Suitable metal complexes (dopants, especially phosphorescent dopants) for use in the inventive OLEDs, preferably as emitter material, are described as following general formula (E-1).

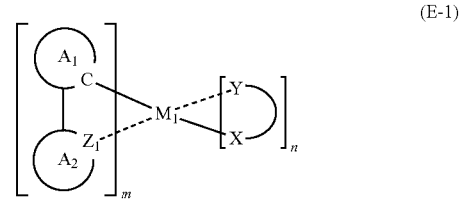

(E-1)

Wherein $M_1$ is a metal having an atomic weight greater than 40, preferably, Ir, Pt, Pd, Rh, Re, Ru, Os, Tl, Pb, Bi, In, Sn, Sb, Te, Au, or Ag, more preferably Ir, Pt, or Os, most preferably Ir, $A_1$ represents aryl group having 6 to 24 carbon atoms or heterocyclic group having 3 to 24 cyclic atoms, preferably above mentioned substituents which may have additional substituents, $A_2$ represents nitrogen containing heterocyclic group having 3 to 24 cyclic atoms, preferably above mentioned substituents which may have additional substituents, $Z_1$ represents C or N, preferably N, (X-Y) is an ancillary ligand, preferably acetylacetonate derivatives, picolinate derivatives, more preferably acetylacetonate derivatives, m is a value from 1 to the maximum number of ligands that may be attached to the metal; and m+n is the maximum number of ligands that may be attached to the metal.

If m or n is more than 2, two or more ligands may be the same or different in each occurrence.

According to one embodiment, a metal complex represented by the following general formula (E-2) is more preferable,

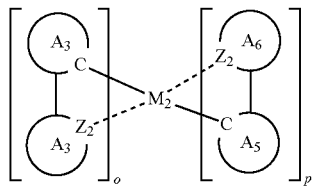

(E-2)

Wherein $M_2$ is a metal having an atomic weight greater than 40, preferably, Ir, Pt, Pd, Rh, Re, Ru, Os, Tl, Pb, Bi, In, Sn, Sb, Te, Au, or Ag, more preferably Ir, Pt, or Os, most preferably Ir, $A_3$, $A_5$ each independently represents aryl group having 6 to 24 carbon atoms or heterocyclic group having 3 to 24 cyclic atoms, preferably above mentioned substituents which may have additional substituents, $A_4$, $A_6$ each independently represents nitrogen containing heterocyclic group having 3 to 24 cyclic atoms, preferably above mentioned substituents which may have additional substituents, $Z_2$, $Z_3$ each independently represents C or N, preferably N, o is a value from 1 to the maximum number of ligands that may be attached to the metal; and o+p is the maximum number of ligands that may be attached to the metal.

If o or p is more than 2, two or more ligands may be the same or different in each occurrence.

A metal complex represented by the following general formula (T) or (β) is more preferable.

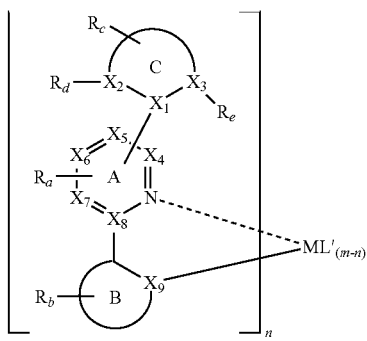

(T)

M represents the above mentioned metal atom,

B, C each independently represents aryl group having 6 to 24 carbon atoms or heteroaryl group having 3 to 24 cyclic atoms, preferably phenyl group, dibenzofuran group, dibenzothiophene group, aza-dibenzofuran group, aza-dibenzothiophene group, which may have additional substituents, A represents a nitrogen containing 6 membered ring structure which may have additional substituents, preferably pyridine, pyrimidine, more preferably pyridine, X4~X8 each represents C or N, preferably C, m represents oxidation state of the metal M, n is 1 or greater than 1, L' represents following chemical structure,

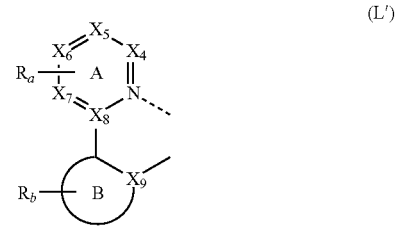

(L')

wherein A represents nitrogen containing 6 membered ring structure which may have additional substituents, preferably pyridine, pyrimidine, more preferably pyridine, B represents aryl group having 6 to 24 carbon atoms or heteroaryl group having 3 to 24 cyclic atoms, preferably phenyl group, dibenzofuran group, dibenzothiophene group, aza-dibenzofuran group, aza-dibenzothiophene group, which may have additional substituents, X9 represents C or N, preferably, N.

Ra, Rb, Rc or Rd each independently represents hydrogen, a substituted or unsubstituted alkyl group having 1 to 25 carbon atoms, a substituted or unsubstituted alkoxy group having 1 to 25 carbon atoms, a substituted or unsubstituted amino group, a substituted or unsubstituted alkenyl group having 2 to 25 carbon atoms, a substituted or unsubstituted alkynyl group having 2 to 25 carbon atoms, a substituted or unsubstituted aralkyl group having 7 to 24 carbon atoms, a substituted or unsubstituted aryl group having 6 to 24 carbon atoms or a substituted or unsubstituted heterocyclic group having 5 to 30 cyclic atoms,

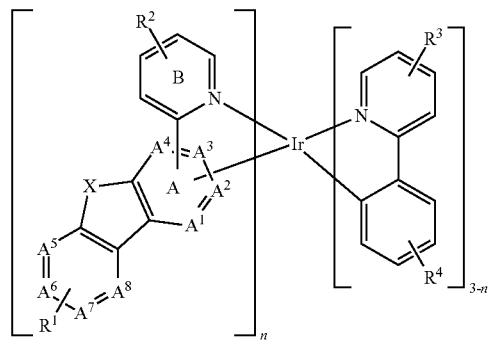

(β)

Wherein X represents NR, oxygen atom, sulfur atom, BR or Selenium atom,

R represents hydrogen atom, a substituted or unsubstituted alkyl group having 1 to 25 carbon atoms, $A^1$, to $A^8$ independently represents CH, $CR^5$ or N, preferably CH or $CR^5$, $R^1$ to $R^5$ each independently represents a substituted or unsubstituted alkyl group having 1 to 25 carbon atoms, a substituted or unsubstituted aryl group having 6 to 24 ring carbon atoms, n is 1, 2 or 3, preferably 1.

In another embodiment, a metal complex represented by any one of the following general formula (V), (X), (Y), (Z) can be used.

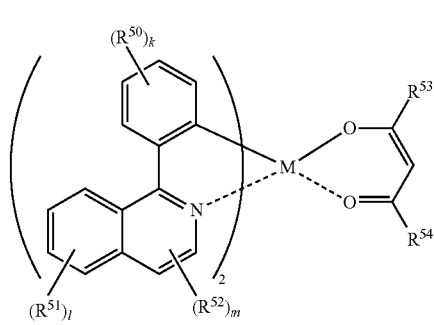 (V)

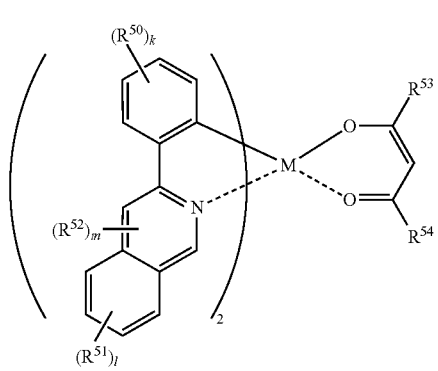 (X)

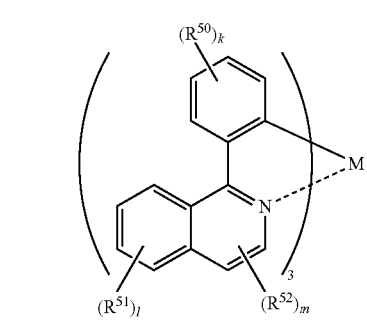 (Y)

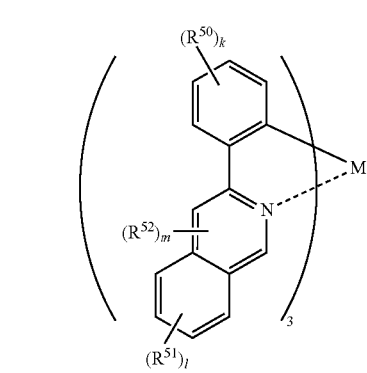 (Z)

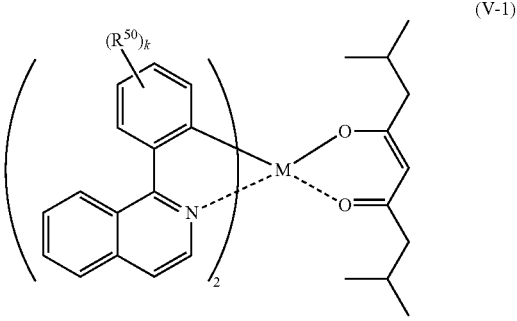 (V-1)

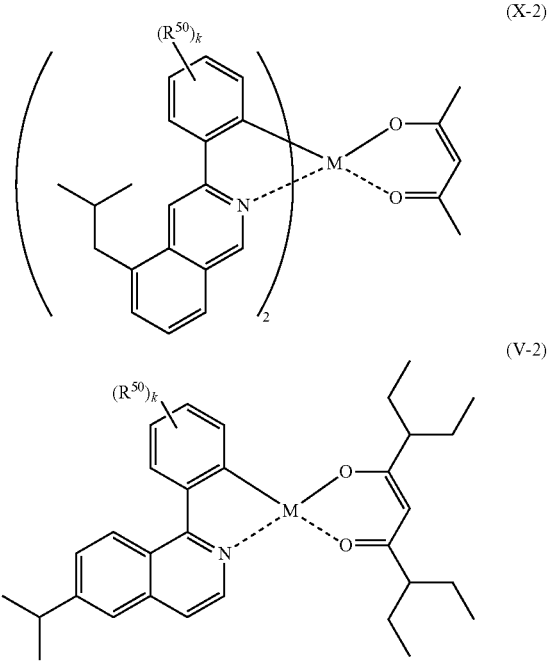

(X-1)

(X-2)

(V-2)

Wherein $R^{50}$ to $R^{54}$ each represents a substituted or unsubstituted alkyl group having 1 to 25 carbon atoms, a substituted or unsubstituted aryl group having 6 to 24 ring carbon atoms, k is 0, 1, 2, 3 or 4, m is 0, 1 or 2, l is 0, 1, 2, 3 or 4, M represents iridium atom (Ir), osmium atom (Os) or platinum atom (Pt).

Formula (V) is preferably represented by formula (V-1) or (V-2). Formula (X) is preferably represented by formula (X-1) or (X-2).

Wherein $R^{50}$, M and k are as defined in formula (V) and (X).

(2) Fluorescent Emitting Layer

The fluorescent emitting layer usually comprises at least one emitter material and at least one host material.

A host material for fluorescent emitting layer is usually selected from general host materials, which preferably have wider band-gap than the emitter material to get highly efficient light emission from the emitter through energy transfer mechanism from the excited host to the emitter. Specific examples of the preferable fluorescent host are, substituted or unsubstituted above mentioned heterocyclic compound; or substituted or unsubstituted aromatic hydrocarbon compound, such as oligo-phenylene derivatives, naphthalene derivatives, fluorene derivatives, fluoranthene derivatives, anthracene derivatives, phenanthrene derivatives, pyrene derivatives, triphenylene derivatives, benzanthracene derivatives, chrysene derivatives, benzphenanthrene derivatives, naphthacene derivatives, benzochrysene derivatives, and so on, preferably anthracene derivatives, pyrene derivatives and naphthacene derivatives, more preferably, anthracene derivatives represented by following general formula (X) especially for fluorescent blue or green device.

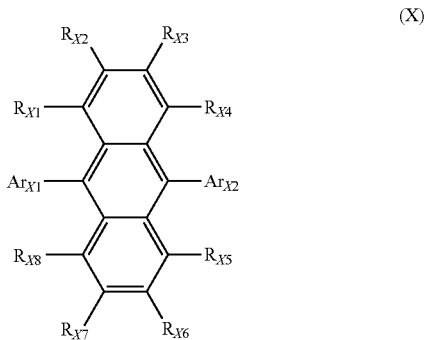

(X)

$Ar_{X1}$ and $Ar_{X2}$ are independently a substituted or unsubstituted aryl group including 6 to 50 ring carbon atoms, preferably phenyl group, biphenyl group, naphthyl group, phenanthryl group, fluorenyl group, fluoranthenyl group, anthryl group, pyrenyl group, benzophenanthryl group, triphenylenyl group, benzanthryl group, benzochrysenyl group, or a heterocyclic group including 5 to 50 ring atoms, preferably, benzofuranyl group, benzothiophenyl group, indolyl group, dibenzothiophenyl group, dibenzofuranyl group, carbazolyl group, benzocarbazoryl group, dibenzocarbazoryl group, indolophenanthryl group, naphthobenzofuranyl group, naphthobenzothiophenyl group, dinaphthofuranyl group, dinaphthothiophenyl group, benzophenanthlofuranyl group, benzophenanthlothiophenyl group, benzofurodibenzofuranyl group, benzothiodibenzothiophenyl group, benzofurodibenzothiophenyl group, benzothiodibenzofuranyl group, more preferably oxygen or sulfur containing heteroaromatics, such as furan or thiophene containing heteroaromatics in one of the part of the heteroaromatics.

$R_{X1}$ to $R_{X8}$ are independently a hydrogen atom, a substituted or unsubstituted aryl group including 6 to 50 ring carbon atoms, a substituted or unsubstituted heterocyclic group including 5 to 50 ring atoms, an alkyl group including 1 to 50 carbon atoms, a substituted or unsubstituted alkoxy group including 1 to 50 carbon atoms, a substituted or unsubstituted aralkyl group including 7 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted alkoxycarbonyl group including 2 to 50 carbon atoms, a substituted or unsubstituted silyl group, a carboxy group, a halogen atom, a cyano group, a nitro group or a hydroxyl group.

An emitter material for fluorescent emitting layer is usually selected from general emitter materials or fluorescent dyes, which preferably have high absorption co-efficiency and high quantum efficiency to get highly efficient light emission from the emitter. Specific examples of the preferable fluorescent emitter are, aromatic hydrocarbon derivatives, such as oligo-phenylene derivatives, naphthalene derivatives, fluorene derivatives, fluoranthenyl group, fused fluoranthenyl group, anthracene derivatives, phenanthrene derivatives, pyrene derivatives, triphenylene derivatives, benzanthracene derivatives, chrysene derivatives, benzphenanthrene derivatives, naphthacene derivatives, benzochrysene derivatives, and so on; aromatic or heterocyclic amine derivatives represented by following general formula (Y); organic boron derivatives represented by general formula (Z),

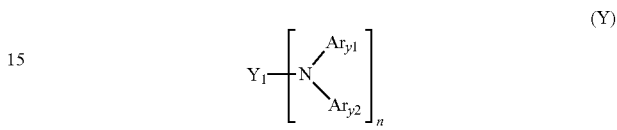

(Y)

Y is a substituted or unsubstituted aromatic hydrocarbon group including 6 to 50 ring carbon atoms, preferably fused aromatic hydrocarbon group, or substituted or unsubstituted heterocyclic group having 5 to 50 cyclic atoms.

$Ar_{y1}$, and $Ar_{y2}$ are independently a substituted or unsubstituted aryl group including 6 to 50 ring carbon atoms or a substituted or unsubstituted heterocyclic ring group including 5 to 50 ring atoms, preferably, oxygen or sulfur containing heterocyclic group.

Specific examples of Y include the above-mentioned fused aryl group. Y is preferably a substituted or unsubstituted anthryl group; a substituted or unsubstituted pyrenyl group; a substituted or unsubstituted chrysenyl group; substituted or unsubstituted fluorenyl group, especially substituted or unsubstituted mono-, di-, or tri-benzofuro-fused fluorene, or substituted or unsubstituted mono-, di-, or tri-benzothio-fused fluorene; substituted or unsubstituted dibenzofuran containing heterocyclic group; substituted or unsubstituted dibenzothiophene containing heterocyclic group.

n is an integer of 1 to 4. It is preferred that n be an integer of 1 to 2.

Electron-Injecting Layer, Electron-Transporting Layer

The electron-transporting layer is an organic layer that is formed between the emitting layer and the cathode and has a function of transporting electrons from the cathode to the emitting layer. When the electron-transporting layer is formed of plural layers, an organic layer that is nearer to the cathode is often defined as the electron-injecting layer. The electron-injecting layer has a function of injecting electrons from the cathode efficiently to the organic layer unit. The preferred electron-injection materials are alkali metal, alkali metal compounds and alkali metal complexes.

According to one embodiment, it is preferred that ET layer further comprising the other one or more layer(s) than electron injection layer to enhance efficiency and lifetime of the device, preferably between an electron injection layer and an emitting layer as a hole blocking layer, a exciton blocking layer or a triplet blocking layer.

A compound of the formula (I) is also preferable as all the use of the electron transporting layer, such as an electron transporting layer, an electron-injecting layer, a hole blocking layer, a exciton blocking layer or a triplet blocking layer.

According to one embodiment, it is preferred that an electron-donating dopant be contained in the interfacial region between the cathode and the emitting unit. Due to such a configuration, the organic EL device can have an increased luminance or a long life. Here, the electron-donating dopant means one having a metal with a work function of 3.8 eV or less. As specific examples thereof, at least one selected from an alkali metal, an alkali metal complex, an alkali metal compound, an alkaline earth metal, an alkaline earth metal complex, an alkaline earth metal compound, a rare earth metal, a rare earth metal complex and a rare earth metal compound or the like can be mentioned.

As the alkali metal, Na (work function: 2.36 eV), K (work function: 2.28 eV), Rb (work function: 2.16 eV), Cs (work function: 1.95 eV) and the like can be given. One having a work function of 2.9 eV or less is particularly preferable. Among them, K, Rb and Cs are preferable. Rb or Cs is further preferable. Cs is most preferable. As the alkaline earth metal, Ca (work function: 2.9 eV), Sr (work function: 2.0 eV to 2.5 eV), Ba (work function: 2.52 eV) and the like can be given. One having a work function of 2.9 eV or less is particularly preferable. As the rare-earth metal, Sc, Y, Ce, Tb, Yb and the like can be given. One having a work function of 2.9 eV or less is particularly preferable.

Examples of the alkali metal compound include an alkali oxide such as Li2O, Cs2O or K2O, and an alkali halide such as LiF, NaF, CsF and KF. Among them, LiF, Li2O and NaF are preferable. Examples of the alkaline earth metal compound include BaO, SrO, CaO, and mixtures thereof such as BaxSr1-xO (0<x<1) and BaxCa1-xO (0<x<1). Among them, BaO, SrO and CaO are preferable. Examples of the rare earth metal compound include YbF3, ScF3, ScO3, Y2O3, Ce2O3, GdF3 and TbF3. Among these, YbF3, ScF3 and TbF3 are preferable.

The alkali metal complexes, the alkaline earth metal complexes and the rare earth metal complexes are not particularly limited as long as they contain, as a metal ion, at least one of alkali metal ions, alkaline earth metal ions, and rare earth metal ions. Meanwhile, preferred examples of the ligand include, but are not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfluborane, bipyridyl, phenanthroline, phthalocyanine, porphyrin, cyclopentadiene, β-diketones, azomethines, and derivatives thereof.

Regarding the addition form of the electron-donating dopant, it is preferred that the electron-donating dopant be formed in a shape of a layer or an island in the interfacial region. A preferred method for the formation is a method in which an organic compound (a light emitting material or an electron-injecting material) for forming the interfacial region is deposited simultaneously with deposition of the electron-donating dopant by a resistant heating deposition method, thereby dispersing the electron-donating dopant in the organic compound. The dispersion concentration of the organic compound:the electron-donating dopant (molar ratio) is 100:1 to 1:100, preferably 5:1 to 1:5.

In a case where the electron-donating dopant is formed into the shape of a layer, the light-emitting material or electron-injecting material which serves as an organic layer in the interface is formed into the shape of a layer. After that, a reductive dopant is solely deposited by the resistant heating deposition method to form a layer preferably having a thickness of from 0.1 nm to 15 nm. In a case where the electron-donating dopant is formed into the shape of an island, the emitting material or the electron-injecting material which serves as an organic layer in the interface is formed into the shape of an island. After that, the electron-donating dopant is solely deposited by the resistant heating deposition method to form an island preferably having a thickness of from 0.05 nm to 1 nm.

The ratio of the main component and the electron-donating dopant in the organic EL device according to the invention is main component:electron-donating dopant=5:1 to 1:5 in terms of molar ratio, more preferably 2:1 to 1:2.

As the electron-transporting material used in the electron-transporting layer other than a compound of the formula (I), an aromatic heterocyclic compound having one or more hetero atoms in the molecule may preferably be used. In particular, a nitrogen containing heterocyclic derivative is preferable.

According to one embodiment, it is preferable that ET layer comprises a nitrogen containing heterocyclic metal chelate, such as 8-hydroxyquinolinolato aluminum, which is generally called as $Alq_3$.

According to the other embodiment, it is preferable that ET layer comprising substituted or unsubstituted nitrogen containing heterocyclic derivative.

Specific examples of the preferable heterocyclic derivative for ET layer are, 6-membered azine derivatives; such as pyridine derivatives, pyrimidine derivatives, triazine derivatives, pyrazine derivatives, preferably pyrimidine derivatives or triazine derivatives; 6-membered fused azine derivatives, such as quinolone derivatives, isoquinoline derivatives, quinoxaline derivatives, quinazoline derivatives, phenanthroline derivatives, benzoquinoline derivatives, benzoisoquinoline derivatives, dibenzoquinoxaline derivatives, preferably quinolone derivatives, isoquinoline derivatives, phenanthroline derivatives; 5-membered heterocyclic derivatives, such as imidazole derivatives, oxazole derivatives, oxadiazole derivatives, triazole derivatives, thiazole derivatives, thiadiazole derivatives; fused imidazole derivatives, such as benzimidazole derivatives, imidazopyridine derivatives, naphthoimidazole derivatives, benzimidazophenanthridine derivatives, benzimidzobenzimidazole derivatives, preferably benzimidazole derivatives, imidazopyridine derivatives or benzimidazophenanthridine derivatives.

According to the other embodiment, it is preferable ET layer comprises phosphine oxide derivative represented as $Ar_{p1}Ar_{p2}Ar_{P3}P=O$.

$Ar_{p1}$~$Ar_{p3}$ are the substituents of phosphor atom and each independently represent substituted or unsubstituted above mentioned aryl group or substituted or unsubstituted above mentioned heterocyclic group.

According to the other embodiment, it is preferable that ET layer comprises aromatic hydrocarbon derivatives.

Specific examples of the preferable aromatic hydrocarbon derivatives for ET layer are, oligo-phenylene derivatives, naphthalene derivatives, fluorene derivatives, fluoranthenyl group, anthracene derivatives, phenanthrene derivatives, pyrene derivatives, tri phenylene derivatives, benzanthracene derivatives, chrysene derivatives, benzphenanthrene derivatives, naphthacene derivatives, benzochrysene derivatives, and so on, preferably anthracene derivatives, pyrene derivatives and fluoranthene derivatives.

Hole-Injection Layer, Hole-Transporting Layer

The hole-transporting layer is an organic layer that is formed between the emitting layer and the anode, and has a function of transporting holes from the anode to the emitting layer. If the hole-transporting layer is composed of plural layers, an organic layer that is nearer to the anode may often be defined as the hole-injecting layer. The hole-injecting layer has a function of injecting holes efficiently to the organic layer unit from the anode.

Said hole injection layer is generally used for stabilizing hole injection from anode to hole transporting layer which is generally consist of organic materials.

Organic material having good contact with anode or organic material with p-type doping is preferably used for the hole injection layer.

Acceptor materials, or fused aromatic hydrocarbon materials or fused heterocycles which have high planarity, are preferably used, acceptor materials are more preferably used for the hole injection layer.

Specific examples for acceptor materials are, the quinone derivatives with one or more electron withdrawing groups, such as $F_4TCNQ$(2,3,5,6-tetrafluoro-7,7,8,8-tetracyanoquinodimethane), 1,2,3-Tris[cyano)(4-cyano-2,3,5,6-tetrafluorophenyl)methylene]cyclopropane, and so on; hexaazatriphenylene derivatives with one or more electron withdrawing groups, such as hexaazatriphenylene-hexanitrile; aromatic hydrocarbon derivatives with one or more electron withdrawing groups; aryl boron derivatives with one or more electron withdrawing groups, and so on.

p-doping is usually consist of one or more p-dopant materials and one or more matrix materials. Matrix materials preferably have shallower HOMO level and p-dopant preferably have deeper LUMO level to enhance the carrier density of the layer. Aryl or heteroaryl amine derivatives are preferably used as the matrix materials. Specific examples for the matrix material are the same as that for hole transporting layer which is explained at the later part. Specific examples for p-dopant are the above mentioned acceptor materials, preferably the quinone derivatives with one or more electron withdrawing groups, such as $F_4TCNQ$, 1,2,3-Tris[cyano)(4-cyano-2,3,5,6-tetrafluorophenyl)methylene]cyclopropane.

The ratio of the p-type dopant is preferably less than 20% of molar ratio, more preferably less than 10%, such as 1%, 3%, 5% and so on.

Hole transporting layer is generally used for injecting and transporting holes efficiently, and aromatic or heterocyclic amine derivatives are preferably used.

Specific examples for hole transporting layer are represented as general formula (H),

(H)

$Ar_1$~$Ar_3$ each independently represents substituted or unsubstituted aryl group having 5 to 50 carbon atoms or substituted or unsubstituted heterocyclic group having 5 to 50 cyclic atoms, preferably phenyl group, biphenyl group, terphenyl group, naphthyl group, phenanthryl group, triphenylenyl group, fluorenyl group, spirobifluorenyl group, indenofluorenyl group, carbazolyl group, dibenzofuranyl group, dibenzothiophenyl group, carbazole substituted aryl group, dibenzofuran substituted aryl group or dibenzothiophene substituted aryl group; two or more substituents selected among $Ar^1$~$Ar^3$ may be bonded to each other to form a ring structure, such as carbazole ring structure, acridane ring structure and so on.

According to one embodiment, it is preferable that at least one of $Ar_1$~$Ar_3$ have additional one aryl or heterocyclic amine substituent, more preferably $Ar_1$ have an additional aryl amino substituent, at the case of that it is preferable that $A_1$ represents substituted or unsubstituted biphenylene group, substituted or unsubstituted fluorenylene group.

A second hole transporting layer may be inserted between the first hole transporting layer and the emitting layer to enhance device performance by blocking excess electrons or excitons. Specific examples for second hole transporting layer is the same as the first hole transporting layer. It is preferably that second hole transporting layer have higher triplet energy to block triplet exciton especially for phosphorescent green device, such as bicarbazole derivatives, biphenylamine derivatives, triphenylenyl amine derivatives, fluorenyl amine derivatives, carbazole substituted arylamine derivatives, dibenzofuran substituted arylamine derivatives, dibenzothiophene substituted arylamine derivatives, and so on.

Spacing Layer

The spacing layer is a layer provided between the fluorescent emitting layer and the phosphorescent emitting layer when the fluorescent emitting layer and the phosphorescent emitting layer are stacked in order to prevent diffusion of excitons generated in the phosphorescent emitting layer to the fluorescent emitting layer or in order to adjust the carrier balance. Further, the spacing layer can be provided between the plural phosphorescent emitting layers.

Since the spacing layer is provided between the emitting layers, the material for the spacing layer is preferably a material having both electron-transporting properties and hole-transporting properties. In order to prevent diffusion of the triplet energy in adjacent phosphorescent emitting layers, it is preferred that the spacing layer have a triplet energy of 2.6 eV or more. As the material used for the spacing layer, the same material as those used in the above-mentioned hole-transporting layer can be given.

Barrier Layer

It is preferred that the organic EL device according to the invention have a barrier layer such as an electron-barrier layer, a hole-barrier layer and a triplet barrier layer in a part that is adjacent to the emitting layer. Here, the electron-barrier layer is a layer that serves to prevent leakage of electrons from the emitting layer to the hole-transporting layer, and the hole-barrier layer is a layer that serves to prevent leakage of holes from the emitting layer to the electron-transporting layer.

The triplet barrier layer prevents diffusion of triplet excitons generated in the emitting layer to the surrounding layers, and has a function of preventing energy deactivation of triplet excitons on molecules in the electron-transporting layer other than the emitting dopant by confining the triplet excitons within the emitting layer.

The organic EL device using the inventive compounds of formula (I) can be used as an emitting device in a panel module used in various displays.

The organic EL device using the inventive compounds of formula (I) can be used as a display element of a TV, a mobile phone and a PC; or an electronic apparatus such as lightings or the like.

The OLEDs (organic EL devices) can be used in all apparatus in which electroluminescence is useful. Suitable devices are preferably selected from stationary and mobile visual display units and illumination units. Stationary visual display units are, for example, visual display units of computers, televisions, visual display units in printers, kitchen appliances and advertising panels, illuminations and information panels. Mobile visual display units are, for example, visual display units in cellphones, tablet PCs, laptops, digital cameras, MP3 players, vehicles and destination displays on buses and trains. Further devices in which the inventive OLEDs can be used are, for example, keyboards; items of clothing; furniture; wallpaper. In addition, the present invention relates to a device selected from the group consisting of stationary visual display units such as visual display units of computers, televisions, visual display units in printers, kitchen appliances and advertising panels, illuminations, information panels, and mobile visual display units such as visual display units in cellphones, tablet PCs, laptops, digital cameras, MP3 players, vehicles and destination displays on buses and trains; illumination units; keyboards; items of clothing; furniture; wallpaper, comprising at least one inventive organic light-emitting diode or at least one inventive light-emitting layer.

The following examples are included for illustrative purposes only and do not limit the scope of the claims. Unless otherwise stated, all parts and percentages are by weight.

EXAMPLES

Compounds Synthesized

Compound 1

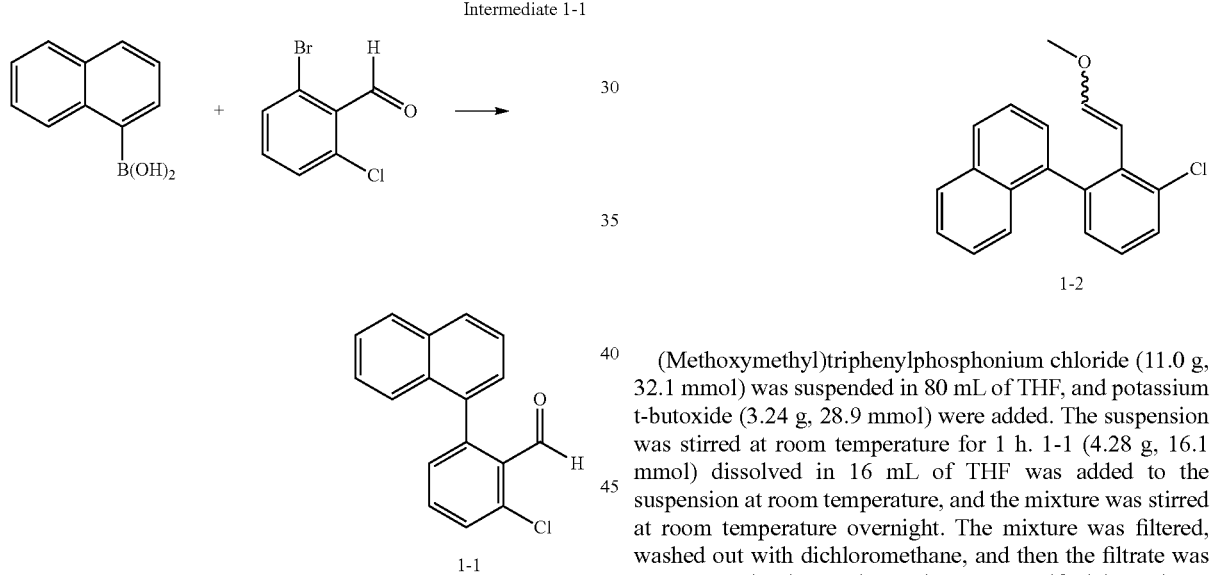

1-Naphthaleneboronic acid (15.48 g, 90 mmol) and 2-bromo-6-chlorobenzaldehyde (19.7 g, 90 mmol) were dissolved in 200 mL of THF. To the solution was added potassium fluoride (15.7 g, 270 mmol) dissolved in 50 mL of water, and the mixture was evacuated and purged with Argon gas. Then, $^t$Bu$_3$P—HBF$_4$ (2.09 g, 7.2 mmol) and Pd$_2$(dba)$_3$ (3.30 g, 3.6 mmol) were added to the mixture, and the mixture was stirred at 50° C. overnight. The reaction mixture was cooled at room temperature, and the solid was removed by filtration. The filtrate was extracted with ethyl acetate. The organic layer was collected, dried with MgSO4, and concentrated. The crude product was purified by column chromatography on silica gel eluting with a mixed solvent of heptane and dichloromethane to yield 16.4 g (68%) of 1-1 as a white powder.

LC-MS: 267 [M+H]

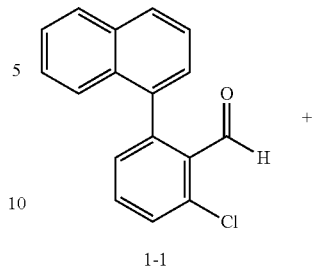

(Methoxymethyl)triphenylphosphonium chloride (11.0 g, 32.1 mmol) was suspended in 80 mL of THF, and potassium t-butoxide (3.24 g, 28.9 mmol) were added. The suspension was stirred at room temperature for 1 h. 1-1 (4.28 g, 16.1 mmol) dissolved in 16 mL of THF was added to the suspension at room temperature, and the mixture was stirred at room temperature overnight. The mixture was filtered, washed out with dichloromethane, and then the filtrate was concentrated. The crude product was purified by column chromatography eluting with heptane and dichloromethane to yield 7.68 g of 1-2 as a beige solid.

The product was used for the next reaction without further purification.

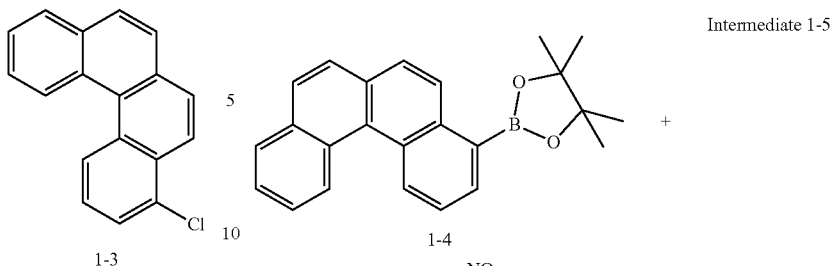

Intermediate 1-5

1-2 (11.8 g, 40 mmol) was dissolved in 200 mL of dichloromethane, and the solution was cooled at 0° C. To the solution was added dropwise methanesulfonic acid (2.28 g, 23.7 mmol) at 0° C., and the mixture was stirred at room temperature overnight. The reaction mixture was gradually poured into ice-water. The layers were separated, and the aqueous layer was extracted with dichloromethane. The organic layer was dried with MgSO₄. After removal of the solvent, the crude product was purified by column chromatography on silica gel eluting with a mixed solvent of heptane and dichloromethane to yield 6.76 g (64%) of 1-3 as a beige solid.

LC-MS: 264 [M+H]

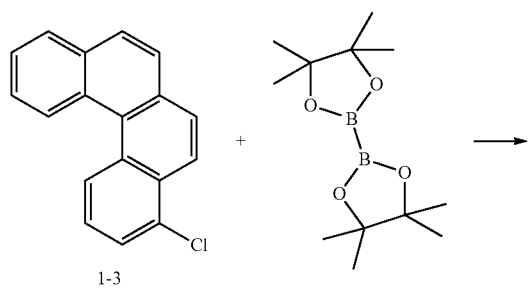

Intermediate 1-4

1-3 (4.89 g, 18.6 mmol), 4, 4, 4', 4', 5, 5, 5', 5'-Octamethyl-2, 2'-bi-1, 3, 2-dioxaborolane (5.67 g, 22.3 mmol), and potassium acetate (4.57 g, 46.5 mmol) were suspended in 25 mL of 1,4-dioxane. Then, Pd₂(dba)₃ (256 mg, 0.28 mmol) and s-Phos (229 mg, 0.56 mmol) were added, and the mixture was refluxed overnight under Argon atmosphere. The reaction mixture was cooled at room temperature, the solid was removed by filtration, and the filtrate was washed with water. The organic layer was dried with MgSO₄. After removal of the solvent, the crude product was purified by column chromatography on silica gel eluting with a mixed solvent of toluene and heptane to yield 4.88 g (74%) of 1-4 as a beige solid.

The product was used for the next reaction without further purification.

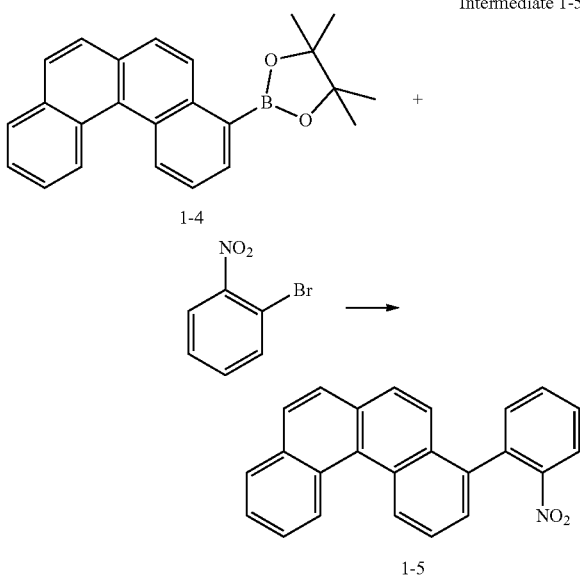

1-4 (4.78 g, 13.5 mmol) and 1-bromo-2-nitrobenzene (2.86 g, 14.2 mmol) were dissolved in 81 mL of toluene and 41 mL of ethanol, and potassium acetate (3.73 g, 27.0 mmol) dissolved in 14 mL of water was added there. Then, Pd(PPh₃)₄ (468 mg, 0.41 mmol) was added. After the mixture was evacuated and purged with Argon, the mixture was stirred at 80° C. for 3.5 h. The crude product was taken up in dichloromethane-heptane and partly evaporated. The precipitated solid was filtered off to yield 4.21 g (89%) of 1-5 as a yellow powder.

LC-MS: 349 [M+H]

Intermediate 1-6

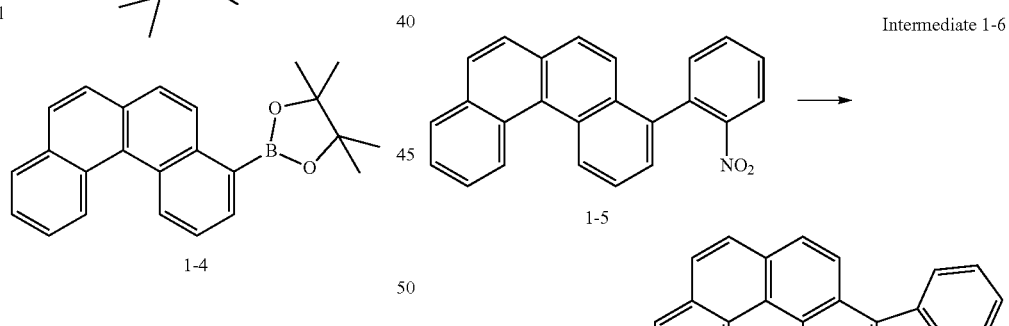

1-5 (3.46 g, 9.90 mmol) and triphenylphosphine (7.79 g, 29.7 mmol) were suspended into 10 mL of 1,2-dichlorobenzene, and the mixture was stirred at 200° C. for 25 h. The reaction mixture was cooled at room temperature, and the solvent was evaporated under vacuum. The crude product was purified by column chromatography on silica gel eluting with a mixed solvent of toluene and cyclohexane to yield 2.38 g (76%) of 1-6 as a yellow solid.

LC-MS: 317 [M+H]

Compound 1

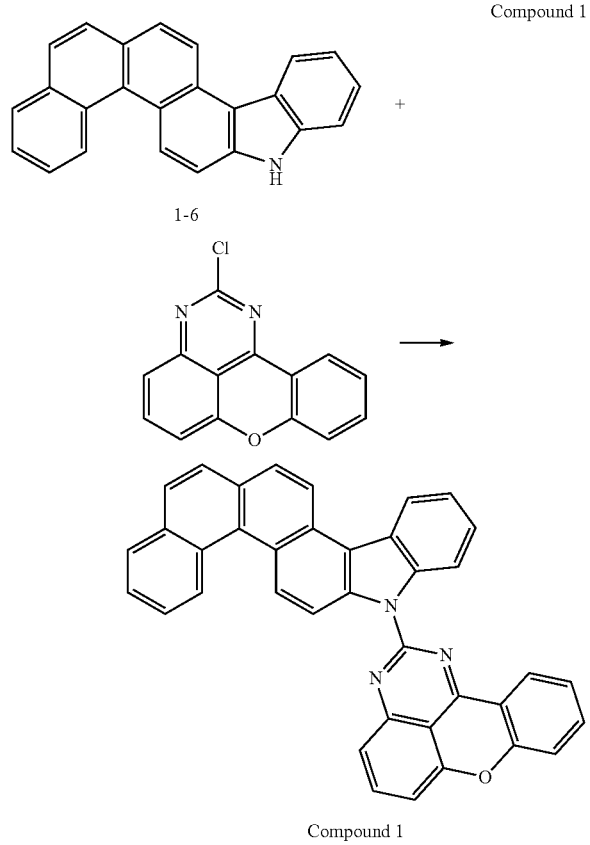

1-6 (1.06 g, 3.34 mmol), 2-chloro-[1]benzopyrano[4,3,2-de]quinazoline (851 mg, 3.34 mmol)(prepared according to the Scheme disclosed in WO2017109727), and potassium carbonate (923 mg, 6.68 mmol) were suspended in 17 mL of DMF. The mixture was stirred at 140° C. for 4 h. The reaction mixture was diluted with ethanol and water, and filtered off. The crude product was recrystallized with a mixed solvent of chlorobenzene and toluene to yield 1.56 g (87%) of Compound 1 as a yellow solid.

LC-MS: 536 [M+H]

Compound 2

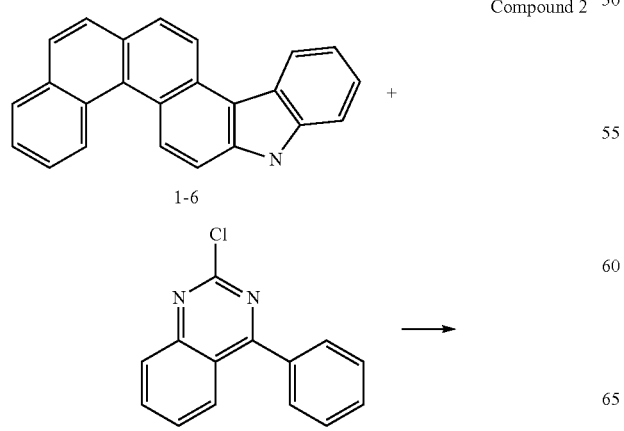

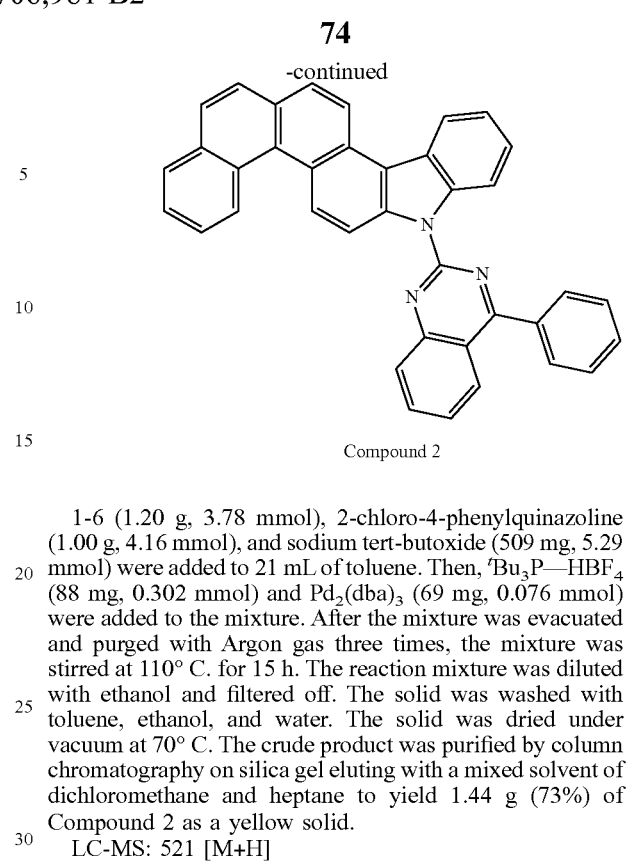

1-6 (1.20 g, 3.78 mmol), 2-chloro-4-phenylquinazoline (1.00 g, 4.16 mmol), and sodium tert-butoxide (509 mg, 5.29 mmol) were added to 21 mL of toluene. Then, $^{t}Bu_3P$—$HBF_4$ (88 mg, 0.302 mmol) and $Pd_2(dba)_3$ (69 mg, 0.076 mmol) were added to the mixture. After the mixture was evacuated and purged with Argon gas three times, the mixture was stirred at 110° C. for 15 h. The reaction mixture was diluted with ethanol and filtered off. The solid was washed with toluene, ethanol, and water. The solid was dried under vacuum at 70° C. The crude product was purified by column chromatography on silica gel eluting with a mixed solvent of dichloromethane and heptane to yield 1.44 g (73%) of Compound 2 as a yellow solid.

LC-MS: 521 [M+H]

Compound 3

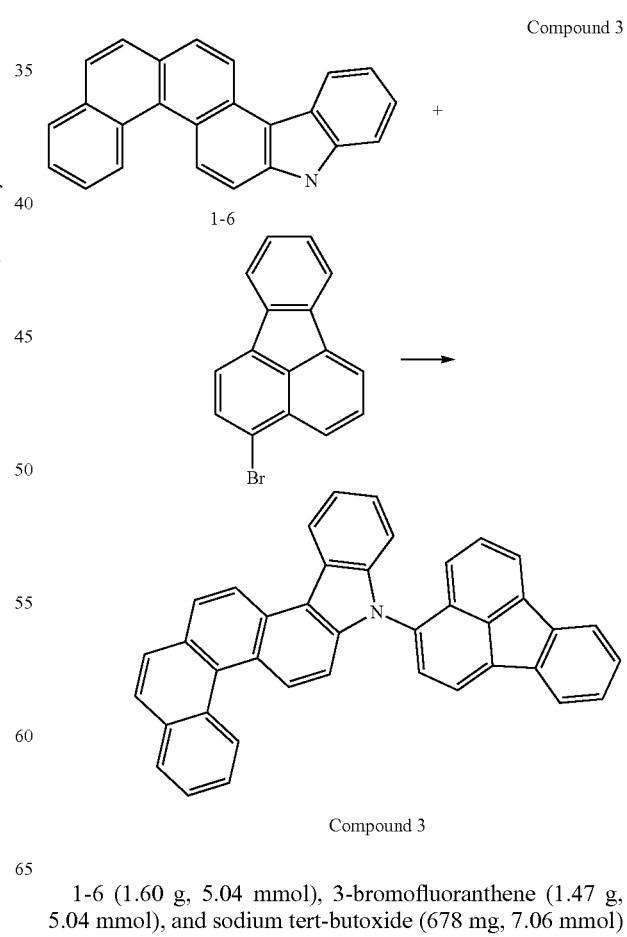

1-6 (1.60 g, 5.04 mmol), 3-bromofluoranthene (1.47 g, 5.04 mmol), and sodium tert-butoxide (678 mg, 7.06 mmol)

were added to 50 mL of xylene. Then, xantphos (146 mg, 0.252 mmol) and Pd₂(dba)₃ (115 mg, 0.126 mmol) were added to the mixture. After the mixture was evacuated and purged with Argon gas three times, the mixture was stirred at 145° C. for 15.5 h. The reaction mixture was diluted with ethanol and filtered off. The solid was washed with toluene, ethanol and water. The solid was dried in vacuum at 70° C. The crude product was purified by column chromatography on silica gel eluting with a mixed solvent of dichloromethane and heptane to yield 2.38 g (91%) of Compound 3 as a yellow solid.

LC-MS: 517 [M+H]

Compound 4

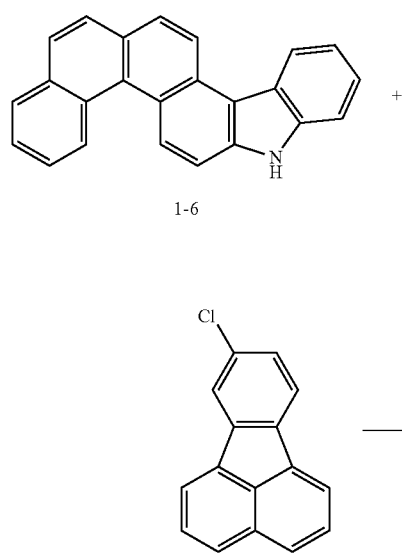

Compound 4

1-6 (1.07 g, 3.37 mmol), 8-chloro-fluoranthene (798 mg, 3.37 mmol), and sodium tert-butoxide (454 mg, 4.72 mmol) were added to 19 mL of xylene. Then, ᵗBu₃P—HBF₄ (78 mg, 0.270 mmol) and Pd₂(dba)₃ (62 mg, 0.067 mmol) were added to the mixture. After the mixture was evacuated and purged with Argon gas three times, the mixture was stirred at 135° C. for 40 h. The reaction mixture was filtered off. The solid was washed with toluene, ethanol and water. The solid was dried under vacuum at 70° C. The crude product was purified by column chromatography on silica gel eluting with a mixed solvent of dichloromethane and heptane to yield 1.60 g (92%) of Compound 4 as a yellow solid.

LC-MS: 517 [M+H]

Compound 5

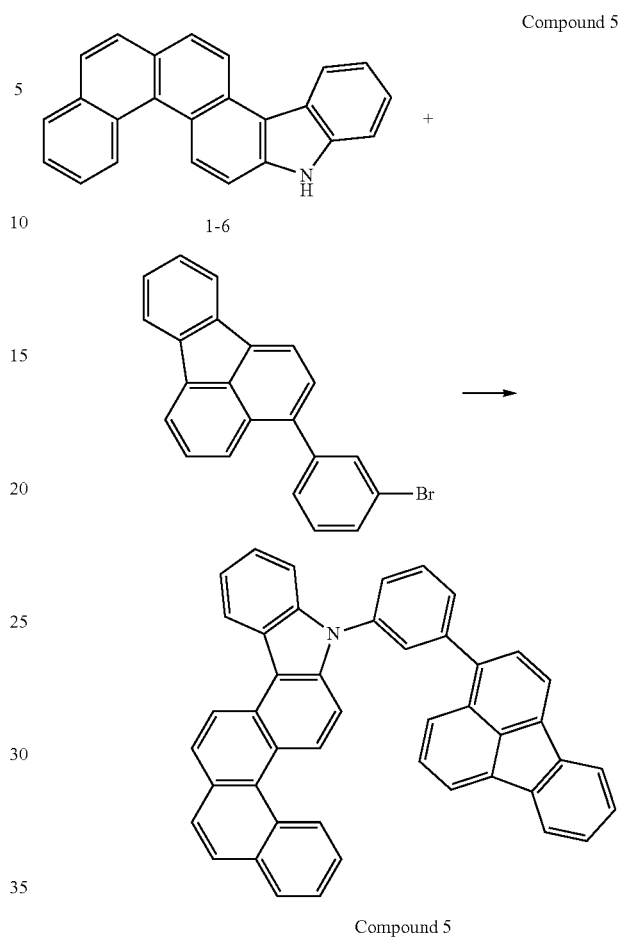

Compound 5

1-6 (1.06 g, 3.34 mmol), (3-bromophenyl)-3-fluoranthene (1.19 g, 3.34 mmol), and sodium tert-butoxide (449 mg, 4.68 mmol) were added to 19 mL of xylene. Then, ᵗBu₃P—HBF₄ (78 mg, 0.270 mmol) and Pd₂(dba)₃ (62 mg, 0.067 mmol) were added to the mixture. After the mixture was evacuated and purged with Argon gas three times, the mixture was stirred at 135° C. for 40 h. The reaction mixture was filtered off. The solid was washed with toluene, ethanol and water. The solid was dried in vacuum at 70° C. The crude product was purified by column chromatography on silica gel eluting with a mixed solvent of toluene and heptane to yield 1.83 g (92%) of Compound 5 as a yellow solid.

LC-MS: 593 [M+H]

Compound 6

Intermediate 6-1

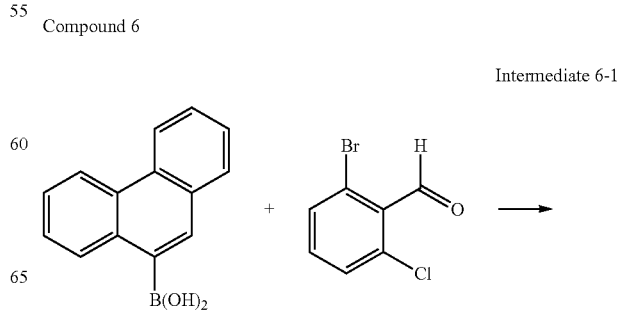

-continued

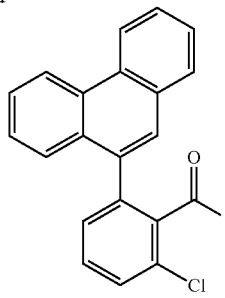

6-1

9-Phenanthreneboronic acid (11.10 g, 50.0 mmol) and 2-bromo-6-chlorobenzaldehyde (11.0 g, 50.0 mmol) were dissolved in 200 mL of THF. To the solution was added potassium fluoride (8.72 g, 150 mmol) dissolved in 50 mL of water, and the mixture was evacuated and purged with Argon gas. Then, $^t$Bu$_3$P—HBF$_4$ (1.60 g, 5.50 mmol) and Pd$_2$(dba)$_3$ (2.34 g, 2.55 mmol) were added to the mixture, and the mixture was stirred at 60° C. overnight. The reaction mixture was cooled at room temperature, and the solid was removed by filtration. The filtrate was extracted with ethyl acetate. The organic layer was collected, dried with MgSO4, and concentrated. The crude product was purified by column chromatography on silica gel eluting with a mixed solvent of heptane and toluene to yield 11.1 g (70%) of 6-1 as a white powder.

LC-MS: 316 [M+H]

Intermediate 6-2

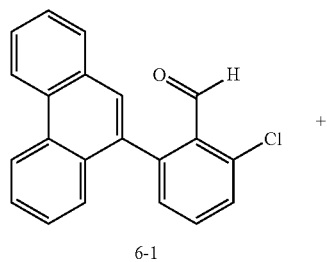

6-1

+

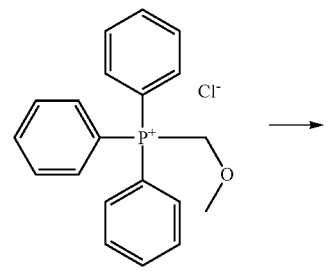

→

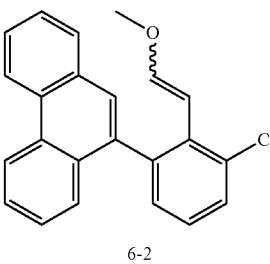

6-2

(Methoxymethyl)triphenylphosphonium chloride (4.83 g, 14.1 mmol) was suspended in 30 mL of THF, and sodium t-butoxide (1.22 g, 12.67 mmol) were added. The suspension was stirred at room temperature for 1 h. 6-1 (2.23 g, 7.04 mmol) dissolved in 15 mL of THF was added to the suspension at room temperature, and the mixture was stirred at room temperature overnight. The mixture was filtered, and washed out with dichloromethane, and then the filtrate was concentrated. The crude product was purified by column chromatography eluting with heptane and dichloromethane to yield 2.10 g of 6-2 as a beige solid.

The product was used for the next reaction without further purification.

Intermediate 6-3

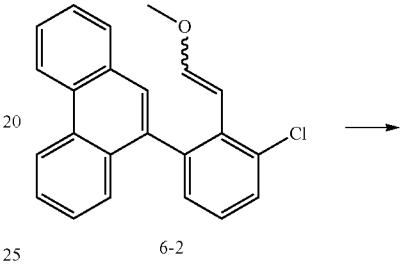

6-2

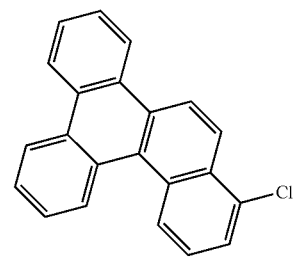

6-3

6-2 (8.75 g, 25.4 mmol) was dissolved in 127 mL of dichloromethane, and the solution was cooled at 0° C. To the solution was added dropwise methanesulfonic acid (2.28 g, 23.7 mmol) at 0° C., and the mixture was stirred at room temperature overnight. The reaction mixture was gradually poured into ice-water. The layers were separated, and the aqueous layer was extracted with dichloromethane. The organic layer was dried with MgSO$_4$. After removal of the solvent, the crude product was purified by column chromatography on silica gel eluting with a mixed solvent of heptane and dichloromethane to yield 6.68 g (84%) of 6-3 as a white solid.

LC-MS: 313 [M+H]

Intermediate 6-4

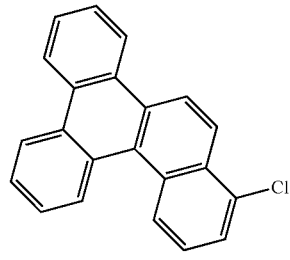

6-3

+

-continued

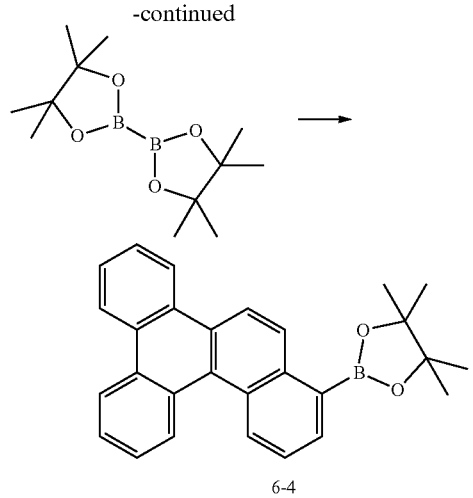

6-4

6-3 (6.65 g, 21.3 mmol), 4, 4, 4', 4', 5, 5, 5', 5'-octamethyl-2, 2'-bi-1, 3, 2-dioxaborolane (6.48 g, 25.5 mmol), and potassium acetate (5.22 g, 53.1 mmol) were suspended in 112 mL of 1,4-dioxane. Then, $Pd_2(dba)_3$ (389 mg, 0.43 mmol) and s-Phos (262 mg, 0.64 mmol) were added, and the mixture was refluxed overnight under Argon atmosphere. The reaction mixture was cooled at room temperature, the solid was removed by filtration, and the filtrate was washed with water. The organic layer was dried with $MgSO_4$. After removal of the solvent, the crude product was purified by column chromatography on silica gel eluting with a mixed solvent of toluene and heptane to yield 6.00 g (70%) of 6-4 as a beige solid.

The product was used for the next reaction without further purification.

Intermediate 6-5

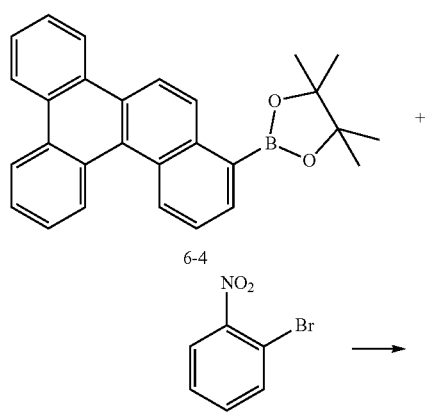

6-4 (6.00 g, 14.8 mmol) and 1-bromo-2-nitrobenzene (3.15 g, 15.6 mmol) were dissolved in 74 mL of toluene and 37 mL of ethanol, and potassium acetate (4.10 g, 29.7 mmol) dissolved in 12 mL of water was added there. Then, $Pd(PPh_3)_4$ (514 mg, 0.45 mmol) was added. The mixture was evacuated and backfilled with Argon, and then the mixture was stirred at 80° C. for 17 h. The reaction mixture was passed through celite, and washed out with toluene. The layers were separated, and the aqueous layer was extracted with toluene. The organic layer was washed with brine, and dried with MgSO4. The crude product was recrystallized with ethyl acetate and heptane to yield 5.24 g (88%) of 6-5 as a yellow powder.

LC-MS: 399 [M+H]

Intermediate 6-6

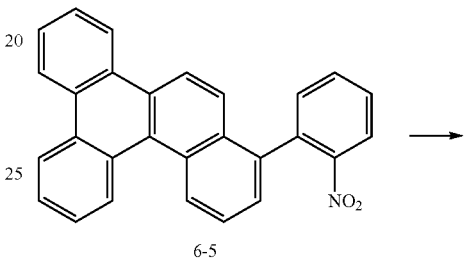

6-5

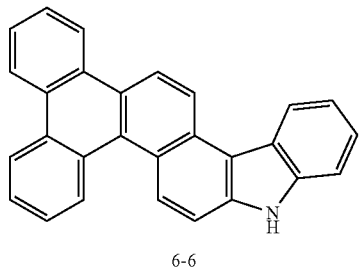

6-6

6-5 (5.24 g, 13.12 mmol) and triphenylphosphine (10.32 g, 39.4 mmol) were suspended into 1,2-dichlorobenzene (3 mL), and stirred at 180° C. overnight. The reaction mixture was cooled at room temperature, and the solvent was evaporated under vacuum. The crude product was purified by column chromatography on silica gel eluting with a mixed solvent of dichloromethane and heptane to yield 4.13 g (86%) of 6-6 as a yellow solid.

LC-MS: 367 [M+H]

Compound 6

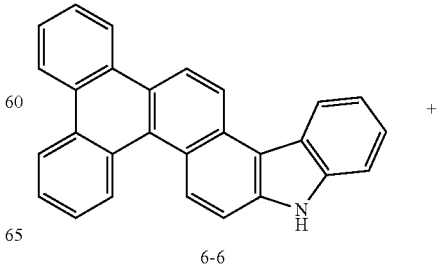

-continued

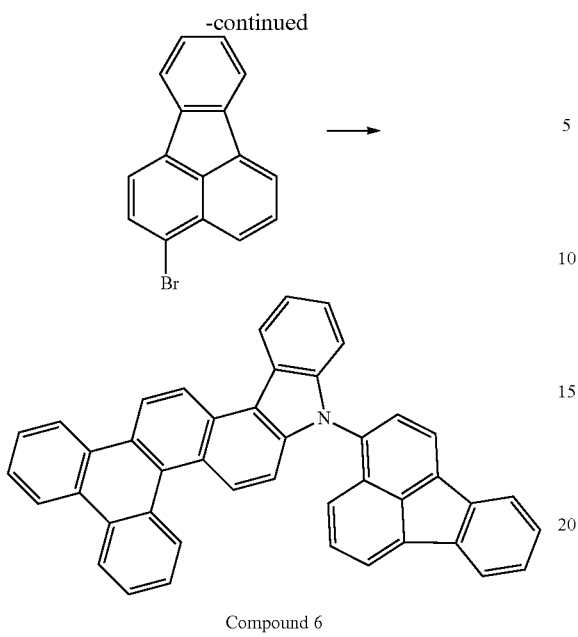

Compound 6

6-6 (517 mg, 1.41 mmol), 3-bromofluoranthene (515 mg, 1.83 mmol), and sodium tert-butoxide (190 mg, 1.98 mmol) were added to 8 mL of xylene. Then, xantphos (65 mg, 0.112 mmol) and $Pd_2(dba)_3$ (52 mg, 0.056 mmol) were added to the mixture. After the reaction mixture was evacuated and purged with Argon gas three times, the mixture was stirred at 145° C. for 17.5 h. The reaction mixture was filtered off. The solid was washed with toluene, ethanol, and water. The solid was dried under vacuum at 70° C. The crude product was purified by column chromatography on silica gel eluting with chloroform to yield 324 mg (41%) of Compound 6 as a yellow solid.

LC-MS: 567 [M+H]

APPLICATION EXAMPLES

Comparative Application Example 1

A glass substrate with 120 nm-thick indium-tin-oxide (ITO) transparent electrode (manufactured by Geomatec Co., Ltd.) used as an anode was first cleaned with isopropanol in an ultrasonic bath for 10 min. To eliminate any possible organic residues, the substrate was exposed to an ultraviolet light and ozone for further 30 min. This treatment also improved the hole injection properties of the ITO. The cleaned substrate was mounted on a substrate holder and loaded into a vacuum chamber. Thereafter, the organic materials specified below were applied by vapor deposition to the ITO substrate at a rate of approx. 0.2-1 Å/sec at about $10^{-6}$-$10^{-8}$ mbar. As a hole injection layer, 5 nm-thick of compound HI was applied. Then 220 nm-thick of compound HT1 was applied as hole transporting layer 1. Subsequently, a mixture of 2% by weight of an emitter compound (EM), 98% by weight of a host (Comparative compound 1) were applied to form a 40 nm-thick phosphorescent-emitting layer. On the emitting layer, 30 nm-thick layer of coevaporated compound ET and Liq at ratio 1:1 by weight was applied as an electron transport layer. Finally, 1 nm-thick Liq was deposited as an electron injection layer and 80 nm-thick Al was then deposited as a cathode to complete the device. The device was sealed with a glass lid and a getter in an inert nitrogen atmosphere with less than 1 ppm of water and oxygen. To characterize the OLED, the current-voltage characteristic was measured in combination with the luminance to determine current efficiency and driving voltage (V). Driving voltage (V) and current efficiency were given at current density of 10 $mA/cm^2$. Lifetime of devices was measured at constant current of 50 $mA/cm^2$. The device results are shown in Table 1.

Compound HI

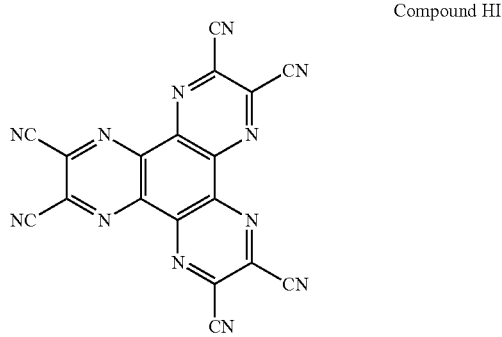

Comparative compound 1

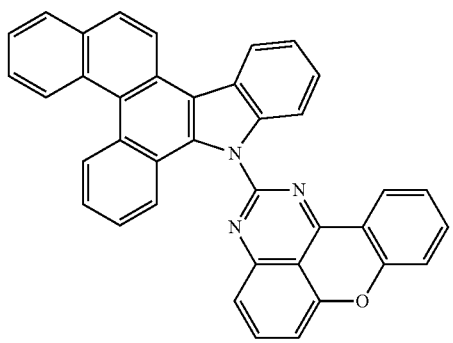

Compound ET

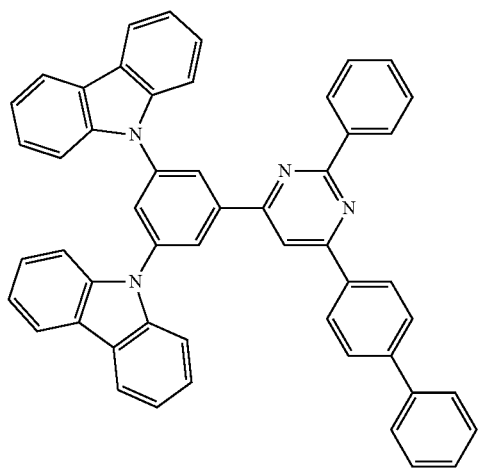

-continued

Compound HT1

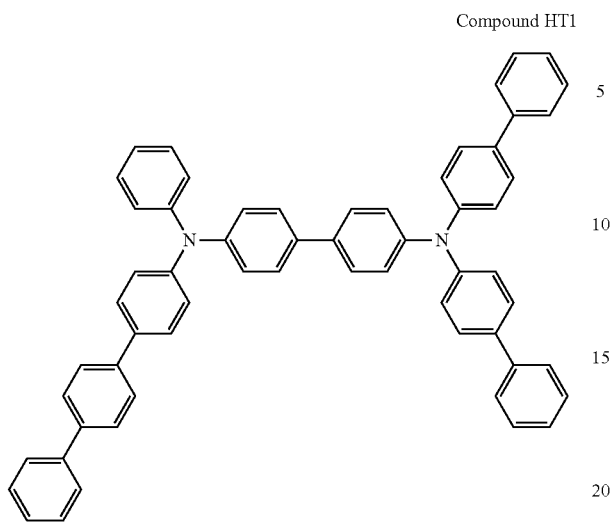

Compound EM

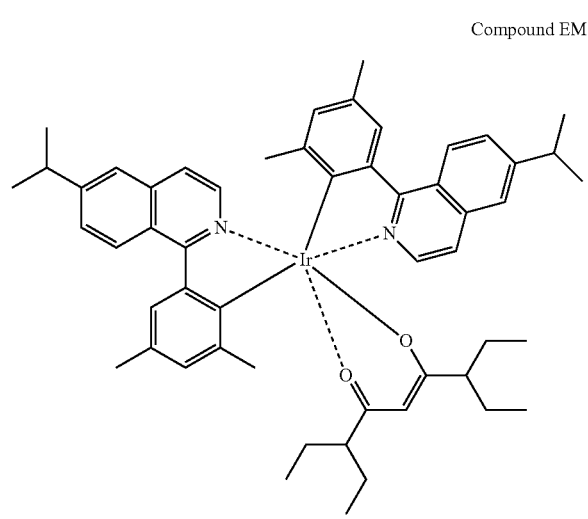

Comparative Application Examples 2 and 3

Comparative Application Example 1 was repeated except for using Comparative compound 2 and 3 in place of the host (Comparative compound 1). The device results are shown in Table 1.

Comparative compound 2

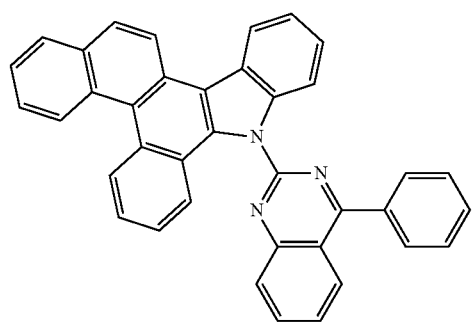

-continued

Comparative compound 3

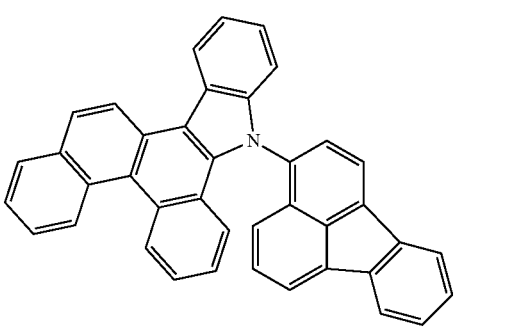

Application Example 1-3

Comparative Application Example 1 was repeated except for using each compound shown in Table 1 in place of the host (Comparative compound 1). The device results are shown in Table 1.

TABLE 1

| Appl. Ex. | Host | Voltage, V | Current Efficiency, cd/A | LT95, h |
|---|---|---|---|---|
| Comp. Appl. Ex. 1 | Comparative Compound 1 | 4.03 | 20.93 | 2.6 |
| Comp. Appl. Ex. 2 | Comparative Compound 2 | 4.13 | 18.04 | 8.2 |
| Comp. Appl. Ex. 3 | Comparative Compound 3 | 3.68 | 18.87 | 29 |
| Appl. Ex. 1 | Compound 1 | 4.14 | 21.03 | 288 |
| Appl. Ex. 2 | Compound 2 | 4.42 | 21.06 | 402 |
| Appl. Ex. 3 | Compound 3 | 3.58 | 23.54 | 114 |

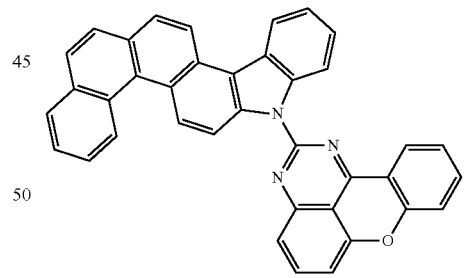

Compound 1

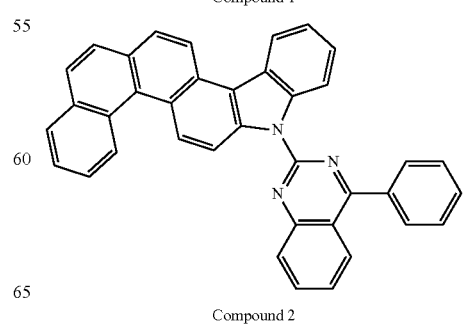

Compound 2

TABLE 1-continued

| Appl. Ex. | Host | Voltage, V | Current Efficiency, cd/A | LT95, h |
|---|---|---|---|---|

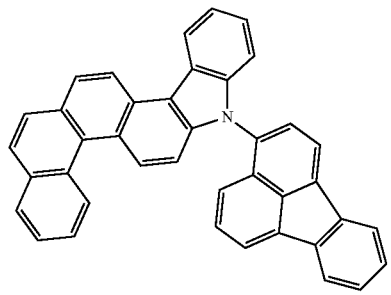

Compound 3

The results shown in Table 1 demonstrated that lifetime was much improved by keeping low driving voltage and high current efficiency in the case that an inventive compound 1, 2, or 3 was used as a host in an OLED.

The invention claimed is:

1. A polycyclic compound represented by formula (I):

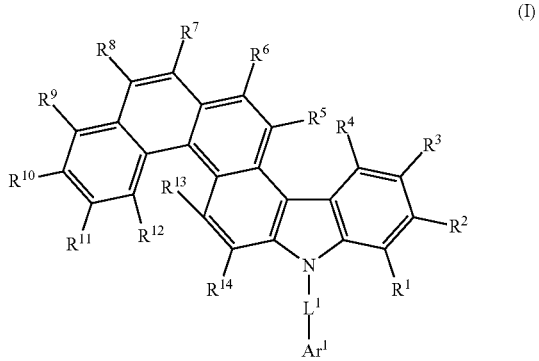

(I)

wherein,
$R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ are independently of each other hydrogen, an unsubstituted or substituted $C_6$-$C_{24}$aryl group, an unsubstituted or substituted $C_1$-$C_{30}$heteroaryl group, an unsubstituted or substituted $C_1$-$C_{25}$alkyl group, an unsubstituted or substituted $C_7$-$C_{25}$aralkyl group, an unsubstituted or substituted $C_5$-$C_{12}$cycloalkyl group, —$NR^{15}R^{16}$, —$OR^{17}$, —$SR^{18}$, —$SiR^{19}R^{20}R^{21}$, —CN or halogen,
wherein
two of $R^1$, $R^2$, $R^3$, $R^4$, $R^5$, $R^6$, $R^7$, $R^8$, $R^9$, $R^{10}$, $R^{11}$ and $R^{12}$, if present at adjacent carbon atoms, together may form an unsubstituted or substituted $C_6$-$C_{18}$aryl ring;
$L_1$ is a direct bond, an unsubstituted or substituted $C_6$-$C_{24}$arylene group, or an unsubstituted or substituted $C_1$-$C_{30}$heteroarylene group; and
$Ar^1$ is an unsubstituted or substituted $C_6$-$C_{24}$aryl group, or an unsubstituted or substituted $C_1$-$C_{30}$heteroaryl group;
$R^{15}$ and $R^{16}$ are independently of each other H, a $C_6$-$C_{18}$aryl group which is unsubstituted or substituted by at least one $C_1$-$C_{18}$alkyl group or at least one $C_1$-$C_{18}$alkoxy group, a $C_1$-$C_{18}$alkyl group or a $C_1$-$C_{18}$alkyl group, which is interrupted by at least one O, or $R^{15}$ and $R^{16}$ together form a five or six membered aliphatic, aromatic or heteroaromatic ring;
$R^{17}$ and $R^{18}$ are independently of each other H, a $C_6$-$C_{18}$aryl group which is unsubstituted or substituted by at least one $C_1$-$C_{18}$alkyl group or at least one $C_1$-$C_{18}$alkoxy group, a $C_1$-$C_{18}$alkyl group or a $C_1$-$C_{18}$alkyl group, which is interrupted by at least one O;
$R^{19}$, $R^{20}$ and $R^{21}$ are independently of each other a $C_1$-$C_{18}$alkyl group, a $C_6$-$C_{18}$aryl group which is unsubstituted or substituted by at least one $C_1$-$C_{18}$alkyl group.

2. The polycyclic compound according to claim 1, wherein $Ar^1$ is an unsubstituted or substituted $C_6$-$C_{16}$aryl group, or an unsubstituted or substituted $C_3$-$C_{15}$heteroaryl group.

3. The polycyclic compound according to claim 1, wherein $L_1$ is a direct bond, an unsubstituted or substituted $C_6$-$C_{13}$arylene group, or an unsubstituted or substituted $C_3$-$C_{12}$heteroarylene group.

4. The polycyclic compound according to claim 1, wherein $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ are independently of each other hydrogen, an unsubstituted or substituted $C_6$-$C_{10}$aryl group, an unsubstituted or substituted $C_3$-$C_{13}$heteroaryl group, an unsubstituted or substituted $C_1$-$C_8$alkyl group, —CN or halogen;
wherein
two of $R^1$, $R^2$, $R^3$, $R^4$, $R^5$, $R^6$, $R^7$, $R^8$, $R^9$, $R^{10}$, $R^{11}$ and $R^{12}$, if present at adjacent carbon atoms, together may form an unsubstituted or substituted $C_6$-$C_{18}$aryl ring.

5. The polycyclic compound according to claim 1, represented by one of the following formula (Ia) or (Ib)

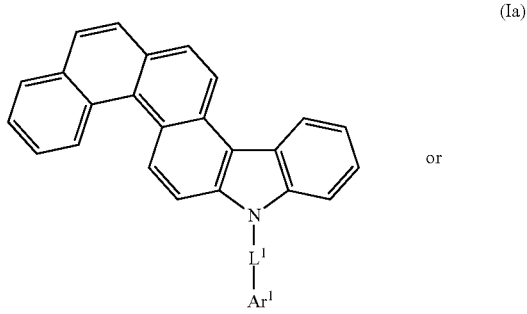

(Ia)

or

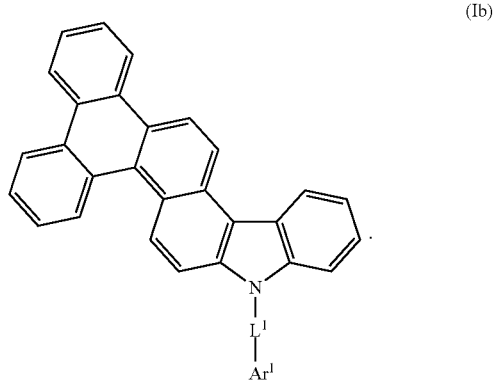

(Ib)

6. The polycyclic compound according to claim 1, wherein
$L^1$ is a direct bond, and
$Ar^1$ is an unsubstituted or substituted fluoranthene group, or an unsubstituted or substituted quinazoline group, an unsubstituted or substituted benzoquinazoline group, or a group of formula (A)

(A)

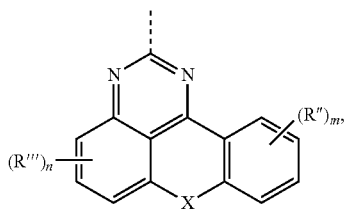

wherein X is O, NR, CR'$_2$ or S, R is an unsubstituted or substituted C$_6$-C$_{10}$ aryl group; R' is C$_1$-C$_4$-alkyl; m is 0, 1, 2, 3 or 4; n is 0, 1, 2 or 3; R" and R'" are independently of each other an unsubstituted or substituted C$_6$-C$_{24}$aryl group, an unsubstituted or substituted C$_1$-C$_{30}$heteroaryl group, an unsubstituted or substituted C$_1$-C$_{25}$alkyl group, an unsubstituted or substituted C$_7$-C$_{25}$aralkyl group, an unsubstituted or substituted C$_5$-C$_{12}$cycloalkyl group, —NR$^{15}$R$^{16}$, —OR$^{17}$, —SR$^{18}$, —SiR$^{19}$R$^{20}$R$^{21}$, —CN or halogen, and the dotted line is a bonding site.

7. A process for the preparation of a compound according to the general formula (I) as defined in claim 1, at least comprising step (A) or step (A*):

(A) Coupling a compound of formula (IIa)

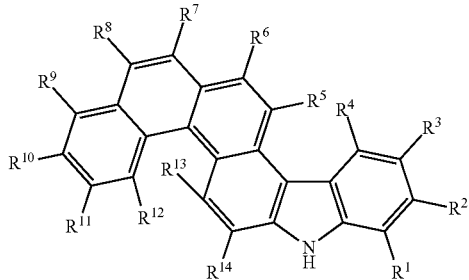

with a compound of formula

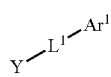

(IIIa)

wherein

Y is a halide selected from the group consisting of I, F, Cl and Br, or a pseudohalide selected from the group consisting of mesylate, triflate, tosylate and nonaflate, or (A*) In the case that L$^1$ is not a single bond—coupling a compound of formula (IIb)

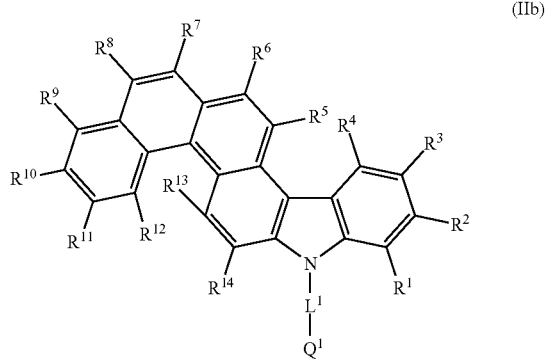

with a compound of formula

(IIIb)

wherein one of Q$^1$ and Q$^2$ is a halide selected from the group consisting of I, F, Cl and Br, or a pseudohalide selected from the group consisting of mesylate, triflate, tosylate and nonaflate; and the other of Q$^1$ and Q$^2$ is BZ$_2$, and Z is C$_1$-C$_8$alkyl, OH, or O—C$_1$-C$_8$alkyl, wherein the two alkyl groups in the group BZ$_2$ may form together with the B and the two oxygen atoms a cyclic group which may be unsubstituted or substituted and/or fused.

8. An electronic device comprising at least one compound as defined in claim 1.

9. The electronic device according to claim 8, comprising a cathode, an anode, and a plurality of organic thin film layers provided between the cathode and the anode, the organic thin film layers comprising an emitting layer comprising the at least one compound of general formula (I).

10. The electronic device according to claim 9, wherein the emitting layer comprises a phosphorescent material, which is an ortho-metallated complex comprising a metal atom selected from iridium (Ir), osmium (Os) and platinum (Pt).

11. An electronic equipment comprising the electronic device according to claim 8.

12. An emitting layer comprising at least one compound of general formula (I) as defined in claim 1.

* * * * *